(12) United States Patent
Nakamura et al.

(10) Patent No.: US 6,710,171 B1
(45) Date of Patent: Mar. 23, 2004

(54) PHYSIOLOGICALLY ACTIVE PROTEIN ORIGINATING IN MAMMALS

(75) Inventors: Yusuke Nakamura, Yokohama (JP); Toshihiro Tanaka, 4-8-401, Shiroganedai 4-chome, Minato-ku, Tokyo (JP); Shuichi Tsukuda, Yokohama (JP)

(73) Assignees: Yusuke Nakamaura, Kanagawa (JP); Toshihiro Tanaka, Tokyo (JP); Shuichi Tsukada, Kanagawa (JP)

( * ) Notice: Subject to any disclaimer, the term of this patent is extended or adjusted under 35 U.S.C. 154(b) by 0 days.

(21) Appl. No.: 09/380,287

(22) PCT Filed: Feb. 27, 1998

(86) PCT No.: PCT/JP98/00835

§ 371 (c)(1),
(2), (4) Date: Nov. 16, 1999

(87) PCT Pub. No.: WO98/38305

PCT Pub. Date: Sep. 3, 1998

(30) Foreign Application Priority Data

Feb. 28, 1997  (JP) .............................................. 9-062259
Feb. 25, 1998  (JP) ........................................... 10-062263

(51) Int. Cl.[7] .............................................. C07H 21/04
(52) U.S. Cl. ................ 536/23.5; 435/252.3; 435/320.1; 435/325
(58) Field of Search ............................ 536/23.5, 24.33; 800/18; 435/320.1, 252.3, 325

(56) References Cited

PUBLICATIONS

Libby et. al., A Cascade Model for Restenosis: A Special Case of Atherosclerosis Progression, 1992, Supplement III Circulaytion vol. 86 No. 6: 47–52.*
Ozeki et. al., Evidence That Implicates the Parathyroid Hormone–Related Peptide in Vascular Stenosis, 1996, Arteriosis, Thrombosis, and Vascular Biology vol. 16. No.4: 565–575.*
Skach et. al., Biogenesis and Transmembrane Topology of the CHIP28 Water Channel at the Endoplasmic Reticulum, 1994 the Journal of Cell Biology vol. 125No. 4.: 803–815.*
Autieri et. al., Isolation and Characterization of BART–1: A Novel Ballon Angioplasty REsponsive Transcript in Rat CArotid Arteries, 1996; DNA and Cell Biology vol. 15,No.4.: 297–304.*
Karim et. al., Histomorphometric and Biochemical Correlates of Arterial Procollagen Gene Expression During Vascular Repair After Experimenatal Angioplasty, 1995, Circulation vol. 91, No. 7.: 2049–2057.*
Crooke, Basic Principles of Antisense Therapeutics, 1998, Antisense Research and Application, 1–50.*
Branch, A good antisense molecule is hard to find, 1998, TIBS vol. 23: 45–50.*
Vannier et. al., The membrane Topology of Human Transient Receptor Potential 3 as Inferred from Glycosylation–scanning Mutagenesis and Epitope Immunocytochemistry, 1998, The Journal of Biological Chemistry, vol. 273: 8675–8679.*
Pourcher et. al., Membrane Topology of the Melibiose Permease of *Escherichia coli* Studied by melB–phoA Fusion Analysis, 1996, Biochemistry vol. 35. No. 13: 4161–4168.*
Houdebine, Production of pharmaceutical proteins from transgenic animals, 1994, Journal of Biotechnology vol. 34: 269–287.*
Wall, TRansgenicLivestock: Progress and Prospects for the Future, 1996, Theriogenology 45: 57–68.*
Theiler, The House Mouse, 1989.*
Makoto Itoh, et al., "Identification by Differential Display of Eight Known Genes Induced During in Vivo Intimal Hyperplasia", 1998, pp. 9–13.
Mark D. Adams et al., "Initial assessemtn of human gene diversity and expression patterns based upon 83 million nucleotides of cDNA sequence", Nature, vol. 377, No. 6547, Suppl., pp. 3–174, Sept. 28, 1995.
Norman H. Lee et al., "Comparative expressed–sequence–tag analysis of differential gene expression profiles in PC–12 cells before and after nerve growth factor treatment" Proc. Nat. Acad. Sci. USA, vol. 92, No. 18, pp. 8303–8307, Aug. 1995.
Michael V. Autieri et al., "Isolation and Characterization of BART–1: A Novel Balloon Angioplasty Responsive Transcript in Rat Carotid Arteries" DNA and Cell Biol., vol. 15, No. 4, pp. 297–304, Nov. 4, 1996.

* cited by examiner

*Primary Examiner*—James Ketter
*Assistant Examiner*—Richard Schnizer
(74) *Attorney, Agent, or Firm*—Banner & Witcoff, Ltd.

(57) ABSTRACT

The present invention provides novel physiologically active protein molecules originating in mammals, which are specifically expressed in arteriosclerosis and/or coronary restenosis, and are predicted to relate closely to the onset and progress of these diseases; DNAs encoding the protein molecules; antibodies reactive with the molecules; and pharmaceutical compositions comprising the above protein molecule or the antibody. The protein molecules, DNAs, and antibodies are useful for treating and preventing arteriosclerosis.

5 Claims, 12 Drawing Sheets

SEQUENCE LISTING

```
<160> NUMBER OF SEQ ID NOS:  42

<210> SEQ ID NO 1
<211> LENGTH: 1399
<212> TYPE: DNA
<213> ORGANISM: Oryctolagus cuniculus
<220> FEATURE:
<221> NAME/KEY: CDS
<222> LOCATION: (1)..(1158)

<400> SEQUENCE: 1 gtc aga atc aac aac ata gca gta gct gta gga aaa gaa gct aaa ctt      48
Val Arg Ile Asn Asn Ile Ala Val Ala Val Gly Lys Glu Ala Lys Leu
  1               5                  10                  15 tac ctg ttc caa gcc cag gaa tgg ctg aag ctg cag gaa agc agt cat      96
Tyr Leu Phe Gln Ala Gln Glu Trp Leu Lys Leu Gln Glu Ser Ser His
             20                  25                  30 gat tac agc tgt cat gaa aaa tta tcc aaa gcc caa ttg aca atg acc     144
Asp Tyr Ser Cys His Glu Lys Leu Ser Lys Ala Gln Leu Thr Met Thr
         35                  40                  45 atg aac cag agt gaa cat aat atg aca gtg tcc cag att cca tct cca     192
Met Asn Gln Ser Glu His Asn Met Thr Val Ser Gln Ile Pro Ser Pro
     50                  55                  60
```

-continued

```
caa acg tgg cac gtg ttt tat gca gac aag tat aca tgc cga gtt gac     240
Gln Thr Trp His Val Phe Tyr Ala Asp Lys Tyr Thr Cys Arg Val Asp
 65                  70                  75                  80 gag gag aat tgg caa gtg gaa gat atc cca ttt gaa atg gtg tta cta     288
Glu Glu Asn Trp Gln Val Glu Asp Ile Pro Phe Glu Met Val Leu Leu
                 85                  90                  95 aac cca gat gct gaa gga aat ccg ttt gat cat ttt ggt gct gga gaa     336
Asn Pro Asp Ala Glu Gly Asn Pro Phe Asp His Phe Gly Ala Gly Glu
            100                 105                 110 tct ggg tta cat gag ttc ttt ttc ctc cta gtc cta gtg tac ttt gtg     384
Ser Gly Leu His Glu Phe Phe Phe Leu Leu Val Leu Val Tyr Phe Val
        115                 120                 125 act gct tgc att tat gcg cag tca ttg tgg cag gct ctt aag aaa gga     432
Thr Ala Cys Ile Tyr Ala Gln Ser Leu Trp Gln Ala Leu Lys Lys Gly
    130                 135                 140 ggg ccc atg cac atg att cta aag gtg ctg aca act gca ctg ctg ttg     480
Gly Pro Met His Met Ile Leu Lys Val Leu Thr Thr Ala Leu Leu Leu
145                 150                 155                 160 caa gct ggt tca gct gta gct aat tac atc cat ttc tcc agt tac tcc     528
Gln Ala Gly Ser Ala Val Ala Asn Tyr Ile His Phe Ser Ser Tyr Ser
                165                 170                 175 aaa gat gga atc ggg gta cct ttt atg gga agc ttg gca gaa ttt ttt     576
Lys Asp Gly Ile Gly Val Pro Phe Met Gly Ser Leu Ala Glu Phe Phe
            180                 185                 190 gac atc gct tcc caa att cag atg tta tac ctg ctt ctg agt ctg tgc     624
Asp Ile Ala Ser Gln Ile Gln Met Leu Tyr Leu Leu Leu Ser Leu Cys
        195                 200                 205 atg ggc tgg acc ata gtc agg atg aag aag tct caa agc aga cct ctc     672
Met Gly Trp Thr Ile Val Arg Met Lys Lys Ser Gln Ser Arg Pro Leu
    210                 215                 220 cag tgg gat tcg acc cct gcc tcc act ggc att gcc gtg ttc att gtc     720
Gln Trp Asp Ser Thr Pro Ala Ser Thr Gly Ile Ala Val Phe Ile Val
225                 230                 235                 240 ctg aca cag agt gtt ttg ctg ctt tgg gaa cag ttt gaa gat acc ggt     768
Leu Thr Gln Ser Val Leu Leu Leu Trp Glu Gln Phe Glu Asp Thr Gly
                245                 250                 255 cat cat agc tcc cat tca cac cac aac tta gca ggg atc ctt ctg atc     816
His His Ser Ser His Ser His His Asn Leu Ala Gly Ile Leu Leu Ile
            260                 265                 270 gtt tta aga att tgc ctg gca ttg tca tta ggc tgt gga ctc tat cag     864
Val Leu Arg Ile Cys Leu Ala Leu Ser Leu Gly Cys Gly Leu Tyr Gln
        275                 280                 285 atc atc aca gtg gag agg agc aca ctc aaa agg gag ttc tac atc aca     912
Ile Ile Thr Val Glu Arg Ser Thr Leu Lys Arg Glu Phe Tyr Ile Thr
    290                 295                 300 ttt gcc aaa ggc tgt atc tta tgg ttt ttg tgc cat cca agt ctg gca     960
Phe Ala Lys Gly Cys Ile Leu Trp Phe Leu Cys His Pro Ser Leu Ala
305                 310                 315                 320 tgc att tct gtc att ttt aat gac tac caa aga gat aag gtt att aca    1008
Cys Ile Ser Val Ile Phe Asn Asp Tyr Gln Arg Asp Lys Val Ile Thr
                325                 330                 335 ata ggt gtt atc ctt ggc cag tct gtt gcc atg gtt atc ctc tac aga    1056
Ile Gly Val Ile Leu Gly Gln Ser Val Ala Met Val Ile Leu Tyr Arg
            340                 345                 350 ctc ttt ctc tcc cac agt cta tac tgg gaa gtt tct tcc ctt tcc tca    1104
Leu Phe Leu Ser His Ser Leu Tyr Trp Glu Val Ser Ser Leu Ser Ser
        355                 360                 365 gta aca cta cca ctg acc gta tcg tct gga cac aaa agc cgc cct cat    1152
Val Thr Leu Pro Leu Thr Val Ser Ser Gly His Lys Ser Arg Pro His
    370                 375                 380
```

-continued

```
ttc tga tacttgattt ctgtggaaaa gaaaagtgaa ggggttaaaa gagtgcaata      1208
Phe
385 aggacccaaa tacagtgact ttttttttcat acatttggta tgaaaaatcg aatagcaaaa  1268 gcagagcatg tttctgtgat aactgcattt aagcagtacc aaaactgaac aaaggtaata  1328 actgaaatgt tttaaaatac atgtaaacaa taaactttca ggaaattctg ttgttaaaaa  1388 aaaaaaaaaa c                                                        1399
```

<210> SEQ ID NO 2
<211> LENGTH: 385
<212> TYPE: PRT
<213> ORGANISM: Oryctolagus cuniculus

<400> SEQUENCE: 2

```
Val Arg Ile Asn Asn Ile Ala Val Ala Val Gly Lys Glu Ala Lys Leu
  1               5                  10                  15

Tyr Leu Phe Gln Ala Gln Glu Trp Leu Lys Leu Gln Glu Ser Ser His
             20                  25                  30

Asp Tyr Ser Cys His Glu Lys Leu Ser Lys Ala Gln Leu Thr Met Thr
         35                  40                  45

Met Asn Gln Ser Glu His Asn Met Thr Val Ser Gln Ile Pro Ser Pro
     50                  55                  60

Gln Thr Trp His Val Phe Tyr Ala Asp Lys Tyr Thr Cys Arg Val Asp
 65                  70                  75                  80

Glu Glu Asn Trp Gln Val Glu Asp Ile Pro Phe Glu Met Val Leu Leu
                 85                  90                  95

Asn Pro Asp Ala Glu Gly Asn Pro Phe Asp His Phe Gly Ala Gly Glu
            100                 105                 110

Ser Gly Leu His Glu Phe Phe Leu Leu Val Leu Val Tyr Phe Val
        115                 120                 125

Thr Ala Cys Ile Tyr Ala Gln Ser Leu Trp Gln Ala Leu Lys Lys Gly
    130                 135                 140

Gly Pro Met His Met Ile Leu Lys Val Leu Thr Thr Ala Leu Leu Leu
145                 150                 155                 160

Gln Ala Gly Ser Ala Val Ala Asn Tyr Ile His Phe Ser Ser Tyr Ser
                165                 170                 175

Lys Asp Gly Ile Gly Val Pro Phe Met Gly Ser Leu Ala Glu Phe Phe
            180                 185                 190

Asp Ile Ala Ser Gln Ile Gln Met Leu Tyr Leu Leu Ser Leu Cys
        195                 200                 205

Met Gly Trp Thr Ile Val Arg Met Lys Lys Ser Gln Ser Arg Pro Leu
    210                 215                 220

Gln Trp Asp Ser Thr Pro Ala Ser Thr Gly Ile Ala Val Phe Ile Val
225                 230                 235                 240

Leu Thr Gln Ser Val Leu Leu Trp Glu Gln Phe Glu Asp Thr Gly
                245                 250                 255

His His Ser Ser His Ser His His Asn Leu Ala Gly Ile Leu Leu Ile
            260                 265                 270

Val Leu Arg Ile Cys Leu Ala Ser Leu Gly Cys Gly Leu Tyr Gln
        275                 280                 285

Ile Ile Thr Val Glu Arg Ser Thr Leu Lys Arg Glu Phe Tyr Ile Thr
    290                 295                 300

Phe Ala Lys Gly Cys Ile Leu Trp Phe Leu Cys His Pro Ser Leu Ala
```

```
                305                 310                 315                 320
Cys Ile Ser Val Ile Phe Asn Asp Tyr Gln Arg Asp Lys Val Ile Thr
                325                 330                 335
Ile Gly Val Ile Leu Gly Gln Ser Val Ala Met Val Ile Leu Tyr Arg
                340                 345                 350
Leu Phe Leu Ser His Ser Leu Tyr Trp Glu Val Ser Ser Leu Ser Ser
                355                 360                 365
Val Thr Leu Pro Leu Thr Val Ser Ser Gly His Lys Ser Arg Pro His
                370                 375                 380
Phe
385

<210> SEQ ID NO 3
<211> LENGTH: 2130
<212> TYPE: DNA
<213> ORGANISM: Homo sapiens
<220> FEATURE:
<221> NAME/KEY: CDS
<222> LOCATION: (97)..(1419)
<221> NAME/KEY: misc_feature
<222> LOCATION: 2001, 2003, 2019, 2033, 2035, 2053, 2079, 2114, 2116,
       2119, 2129
<223> OTHER INFORMATION: n is a or g or c or t

<400> SEQUENCE: 3
ctccggcgcc cacccgcct ccccagctg ccgacgtggg gcgggcagcc gccggcggct         60
gggagccgag gcgtcggtgc agacctggag acgggc atg ggg ggg ctg cgg ctg       114
                                       Met Gly Gly Leu Arg Leu
                                        1               5 ctg gct gtg gcc ctc acg tgc tgc tgg tgg ccg cag ggc agc cag ggt       162
Leu Ala Val Ala Leu Thr Cys Cys Trp Trp Pro Gln Gly Ser Gln Gly
         10                  15                  20 aag acc ctg cgg ggc agc ttc agc agc acc gcg gcc cag gac gcc cag       210
Lys Thr Leu Arg Gly Ser Phe Ser Ser Thr Ala Ala Gln Asp Ala Gln
     25                  30                  35 ggc cag cgc atc ggc cac ttc gag ttc cat ggt gac cat gct ctt ctg       258
Gly Gln Arg Ile Gly His Phe Glu Phe His Gly Asp His Ala Leu Leu
 40                  45                  50 tgt gtc aga atc aac aac ata gca gta gct gtt gga aaa gaa gct aaa       306
Cys Val Arg Ile Asn Asn Ile Ala Val Ala Val Gly Lys Glu Ala Lys
 55                  60                  65                  70 ctc tac ctg ttc caa gcc cag gaa tgg cta aag cta cag caa agc agt       354
Leu Tyr Leu Phe Gln Ala Gln Glu Trp Leu Lys Leu Gln Gln Ser Ser
             75                  80                  85 cat ggt tat agc tgt agt gaa aaa tta tcc aaa gct cag ttg aca atg       402
His Gly Tyr Ser Cys Ser Glu Lys Leu Ser Lys Ala Gln Leu Thr Met
         90                  95                 100 acc atg aac cag acc gaa cat aat ctg aca gtg tcc cag att ccg tct       450
Thr Met Asn Gln Thr Glu His Asn Leu Thr Val Ser Gln Ile Pro Ser
     105                 110                 115 cca caa acg tgg cat gtg ttt tat gca gac aag tat aca tgc caa gat       498
Pro Gln Thr Trp His Val Phe Tyr Ala Asp Lys Tyr Thr Cys Gln Asp
 120                 125                 130 gac aag gag aat tct cag gtg gaa gat atc cca ttt gaa atg gtg tta       546
Asp Lys Glu Asn Ser Gln Val Glu Asp Ile Pro Phe Glu Met Val Leu
135                 140                 145                 150 cta aac cca gat gcc gaa ggg aat cca ttt gat cat ttt agt gct gga       594
Leu Asn Pro Asp Ala Glu Gly Asn Pro Phe Asp His Phe Ser Ala Gly
             155                 160                 165 gaa tct ggg tta cat gag ttc ttt ttc ctc cta gtc cta gtg tac ttt       642
```

```
                                             -continued

Glu Ser Gly Leu His Glu Phe Phe Leu Leu Val Val Tyr Phe
            170                 175                 180 gtg att gct tgc att tat gct caa tca ttg tgg cag gct att aag aaa       690
Val Ile Ala Cys Ile Tyr Ala Gln Ser Leu Trp Gln Ala Ile Lys Lys
                185                 190                 195 ggc gga ccc atg cac atg att tta aag gtt ctg aca act gca ttg ctg       738
Gly Gly Pro Met His Met Ile Leu Lys Val Leu Thr Thr Ala Leu Leu
        200                 205                 210 tta caa gct ggt tca gct tta gct aat tac att cat ttc tcc agt tac       786
Leu Gln Ala Gly Ser Ala Leu Ala Asn Tyr Ile His Phe Ser Ser Tyr
215                 220                 225                 230 tcc aaa gat gga ata ggg gta cca ttt atg gga agt ttg gca gaa ttt       834
Ser Lys Asp Gly Ile Gly Val Pro Phe Met Gly Ser Leu Ala Glu Phe
                235                 240                 245 ttt gac atc gct tcc caa att cag atg tta tac tta ctt ttg agt cta       882
Phe Asp Ile Ala Ser Gln Ile Gln Met Leu Tyr Leu Leu Leu Ser Leu
        250                 255                 260 tgc atg ggt tgg aca ata gtc aga atg aag aag tct caa agc aga cct       930
Cys Met Gly Trp Thr Ile Val Arg Met Lys Lys Ser Gln Ser Arg Pro
265                 270                 275 ctc cag tgg gat tct acg cct gca tcc act ggc att gca gta ttc att       978
Leu Gln Trp Asp Ser Thr Pro Ala Ser Thr Gly Ile Ala Val Phe Ile
        280                 285                 290 gtc atg aca cag agt gtt ttg cta ctt tgg gaa cag ttt gaa gat atc      1026
Val Met Thr Gln Ser Val Leu Leu Leu Trp Glu Gln Phe Glu Asp Ile
295                 300                 305                 310 agt cat cat agc tac cat tca cac cac aac tta gca ggg atc ctc cta      1074
Ser His His Ser Tyr His Ser His His Asn Leu Ala Gly Ile Leu Leu
                315                 320                 325 att gtt cta aga att tgc cta gca ttg tca tta ggc tgt gga ctc tat      1122
Ile Val Leu Arg Ile Cys Leu Ala Leu Ser Leu Gly Cys Gly Leu Tyr
        330                 335                 340 cag atc atc aca gtg gag aga agt aca ctc aaa agg gag ttc tac atc      1170
Gln Ile Ile Thr Val Glu Arg Ser Thr Leu Lys Arg Glu Phe Tyr Ile
                345                 350                 355 aca ttt gcc aaa ggc tgt atc ttg tgg ttt tta tgc cat cca gtt ctt      1218
Thr Phe Ala Lys Gly Cys Ile Leu Trp Phe Leu Cys His Pro Val Leu
        360                 365                 370 gca tgc att tct gtc att ttt agc gac tac caa aga gac aag gtt att      1266
Ala Cys Ile Ser Val Ile Phe Ser Asp Tyr Gln Arg Asp Lys Val Ile
375                 380                 385                 390 aca ata ggt gtt atc ctt tgc cag tct gtt tcc atg gtt att ctc tac      1314
Thr Ile Gly Val Ile Leu Cys Gln Ser Val Ser Met Val Ile Leu Tyr
                395                 400                 405 aga ctc ttt ctg tct cac agt cta tac tgg gaa gtt tct tca ctt tct      1362
Arg Leu Phe Leu Ser His Ser Leu Tyr Trp Glu Val Ser Ser Leu Ser
        410                 415                 420 tca gta aca cta cca ctg acc ata tca tct gga cac aaa agt cgc cct      1410
Ser Val Thr Leu Pro Leu Thr Ile Ser Ser Gly His Lys Ser Arg Pro
425                 430                 435 cat ttc tga tacttgattt ttgttgagag gaaaagtgaa ttggttaaaa              1459
His Phe
    440 gagtgcaata aggatccaaa tacagtgact ttttttttcat acatttagta tgaaaacttg   1519 aacagcgaaa gcagagcatg ttatttatat aactgcattt aagcagtacc aagactgaaa   1579 aaaaaggtaa taaatgaaat gttttgaaat atacttaaac aacaaacttt gaagaaagtg   1639 ttgttataaa attattgaag cgatttctat gtggaaataa atgtgaaaaa taaaactatg   1699
```

-continued

```
atattttggt aaaatattca ccacttataa tgcctcatct taatagctaa ctcasgttta    1759
atartcttat aaaaagtaat cagttaaatg aatacttgct tataaatatc taaactaatc    1819
cactttatga aatcagtgtt atacattgaa ttttaaaact gctgcctttt atgcctttaa    1879
ggaaaatgtt tttccctatt ttgaatttta aaggaattga aattcctccc ggaaattaat    1939
ataaataggg ttccccgtta aatgaaataa accctggttt aattggtggg gtggaattaa    1999
tncncccaat ttttcccgn cccttttttg gggncncatt ttccgggttt taanccttga    2059
ataaaccaaa gggtttttgn aaaaacccct ttttgaaaa aaaattaaaa ccttnanttn     2119
cctttacccn g                                                        2130
```

<210> SEQ ID NO 4
<211> LENGTH: 440
<212> TYPE: PRT
<213> ORGANISM: Homo sapiens

<400> SEQUENCE: 4

```
Met Gly Gly Leu Arg Leu Leu Ala Val Ala Leu Thr Cys Cys Trp Trp
 1               5                  10                  15

Pro Gln Gly Ser Gln Gly Lys Thr Leu Arg Gly Ser Phe Ser Ser Thr
                20                  25                  30

Ala Ala Gln Asp Ala Gln Gly Gln Arg Ile Gly His Phe Glu Phe His
            35                  40                  45

Gly Asp His Ala Leu Leu Cys Val Arg Ile Asn Asn Ile Ala Val Ala
        50                  55                  60

Val Gly Lys Glu Ala Lys Leu Tyr Leu Phe Gln Ala Gln Glu Trp Leu
    65                  70                  75                  80

Lys Leu Gln Gln Ser Ser His Gly Tyr Ser Cys Ser Glu Lys Leu Ser
                85                  90                  95

Lys Ala Gln Leu Thr Met Thr Met Asn Gln Thr Glu His Asn Leu Thr
            100                 105                 110

Val Ser Gln Ile Pro Ser Pro Gln Thr Trp His Val Phe Tyr Ala Asp
        115                 120                 125

Lys Tyr Thr Cys Gln Asp Asp Lys Glu Asn Ser Gln Val Glu Asp Ile
    130                 135                 140

Pro Phe Glu Met Val Leu Leu Asn Pro Asp Ala Glu Gly Asn Pro Phe
145                 150                 155                 160

Asp His Phe Ser Ala Gly Glu Ser Gly Leu His Glu Phe Phe Phe Leu
                165                 170                 175

Leu Val Leu Val Tyr Phe Val Ile Ala Cys Ile Tyr Ala Gln Ser Leu
            180                 185                 190

Trp Gln Ala Ile Lys Lys Gly Gly Pro Met His Met Ile Leu Lys Val
        195                 200                 205

Leu Thr Thr Ala Leu Leu Gln Ala Gly Ser Ala Leu Ala Asn Tyr
    210                 215                 220

Ile His Phe Ser Tyr Ser Lys Asp Gly Ile Gly Val Pro Phe Met
225                 230                 235                 240

Gly Ser Leu Ala Glu Phe Phe Asp Ile Ala Ser Gln Ile Gln Met Leu
                245                 250                 255

Tyr Leu Leu Ser Leu Cys Met Gly Trp Thr Ile Val Arg Met Lys
            260                 265                 270

Lys Ser Gln Ser Arg Pro Leu Gln Trp Asp Ser Thr Pro Ala Ser Thr
        275                 280                 285

Gly Ile Ala Val Phe Ile Val Met Thr Gln Ser Val Leu Leu Leu Trp
```

-continued

```
                    290                 295                 300
Glu Gln Phe Glu Asp Ile Ser His His Ser Tyr His Ser His Asn
305                 310                 315                 320

Leu Ala Gly Ile Leu Leu Ile Val Leu Arg Ile Cys Leu Ala Leu Ser
                325                 330                 335

Leu Gly Cys Gly Leu Tyr Gln Ile Ile Thr Val Glu Arg Ser Thr Leu
                340                 345                 350

Lys Arg Glu Phe Tyr Ile Thr Phe Ala Lys Gly Cys Ile Leu Trp Phe
                355                 360                 365

Leu Cys His Pro Val Leu Ala Cys Ile Ser Val Ile Phe Ser Asp Tyr
370                 375                 380

Gln Arg Asp Lys Val Ile Thr Ile Gly Val Ile Leu Cys Gln Ser Val
385                 390                 395                 400

Ser Met Val Ile Leu Tyr Arg Leu Phe Leu Ser His Ser Leu Tyr Trp
                405                 410                 415

Glu Val Ser Ser Leu Ser Ser Val Thr Leu Pro Leu Thr Ile Ser Ser
                420                 425                 430

Gly His Lys Ser Arg Pro His Phe
                435                 440
```

<210> SEQ ID NO 5
<211> LENGTH: 1918
<212> TYPE: DNA
<213> ORGANISM: Mus musculus
<220> FEATURE:
<221> NAME/KEY: CDS
<222> LOCATION: (82)..(1383)
<221> NAME/KEY: misc_feature
<222> LOCATION: (469)..(471)
<223> OTHER INFORMATION: n is a or g or c or t
      Xaa is Tyr or His or Gln or Asn or Lys or Asp or Glu

<400> SEQUENCE: 5

```
ggcacgagcc gccctctgct gccgacgtgg gctgcaggcc gcaggcggtt gccgggcgag     60
caaacggagc gggcggcggg c atg ggc ggc ctg cgg ctg ctg gcg gta gcc    111
                        Met Gly Gly Leu Arg Leu Leu Ala Val Ala
                         1               5                  10 ctc acg tgc agc tgc tgg tgg ccg cag ggc ggc cag ggc aag acc ctg    159
Leu Thr Cys Ser Cys Trp Trp Pro Gln Gly Gly Gln Gly Lys Thr Leu
             15                  20                  25 cgt ggc agc ttc agc agc gcc gcg gcc cgc gac gcc cag ggc cag agc    207
Arg Gly Ser Phe Ser Ser Ala Ala Ala Arg Asp Ala Gln Gly Gln Ser
         30                  35                  40 atc ggc cat ttc gag ttc cac cga atc aac aac gta gca gtg gct gtt    255
Ile Gly His Phe Glu Phe His Arg Ile Asn Asn Val Ala Val Ala Val
     45                  50                  55 gga aaa gaa gct aaa ctc tac ctg ttc caa gcc cag gaa tgg ctg aag    303
Gly Lys Glu Ala Lys Leu Tyr Leu Phe Gln Ala Gln Glu Trp Leu Lys
 60                  65                  70 ctg ctg gag agc agc ccc ggc tac agc tgc agt gag cgg cta gcc cga    351
Leu Leu Glu Ser Ser Pro Gly Tyr Ser Cys Ser Glu Arg Leu Ala Arg
 75                  80                  85                  90 gct cag ctg aca gtg aca gtg acc cag acg gag cac aac ctc aca gtg    399
Ala Gln Leu Thr Val Thr Val Thr Gln Thr Glu His Asn Leu Thr Val
                 95                 100                 105 tcc cag ctg ccc gct ccc cag aca tgg cga gtg ttc tat gcc gac aag    447
Ser Gln Leu Pro Ala Pro Gln Thr Trp Arg Val Phe Tyr Ala Asp Lys
            110                 115                 120 ttc acc tgc agg gat gac tca nas agc ccc cag ggg gag gag atc ccc    495
```

```
Phe Thr Cys Arg Asp Asp Ser Xaa Ser Pro Gln Gly Glu Glu Ile Pro
            125                 130                 135 ttt gaa atg gtg ctc ctc aac ccg gac gcc gag gga aac ccg ctg gat     543
Phe Glu Met Val Leu Leu Asn Pro Asp Ala Glu Gly Asn Pro Leu Asp
    140                 145                 150 cat ttt agc gcc aga gag tcc ggg ctc cac gag ttc ttt ttc ctc ctc     591
His Phe Ser Ala Arg Glu Ser Gly Leu His Glu Phe Phe Phe Leu Leu
155                 160                 165                 170 gtc cta gtg tac ttt gtg act gcg tgc atc tat gcg cag tct ctg tgg     639
Val Leu Val Tyr Phe Val Thr Ala Cys Ile Tyr Ala Gln Ser Leu Trp
                175                 180                 185 cag gct atg aag aag gga gga ccc atg cac acc atc tta aag gtc ctc     687
Gln Ala Met Lys Lys Gly Gly Pro Met His Thr Ile Leu Lys Val Leu
            190                 195                 200 acc act gca ctg ctg ctt caa gct gct tca gcc tta gct aat tac atc     735
Thr Thr Ala Leu Leu Leu Gln Ala Ala Ser Ala Leu Ala Asn Tyr Ile
        205                 210                 215 cac ttg tcc agg tac tcc aga gat ggg cta gga gtg cct ctc ata gga     783
His Leu Ser Arg Tyr Ser Arg Asp Gly Leu Gly Val Pro Leu Ile Gly
    220                 225                 230 agc ctg gca gaa gtt ttt gac att gcc tcc caa att cag atg ctg tac     831
Ser Leu Ala Glu Val Phe Asp Ile Ala Ser Gln Ile Gln Met Leu Tyr
235                 240                 245                 250 ctg ctt ctg agc ctg tgt atg ggc tgg aca ata gtg cgg atg aag aag     879
Leu Leu Leu Ser Leu Cys Met Gly Trp Thr Ile Val Arg Met Lys Lys
                255                 260                 265 tcg cag agc aga ccg ctc cag tgg gac tcg aca ccc gcg tcc acg ggc     927
Ser Gln Ser Arg Pro Leu Gln Trp Asp Ser Thr Pro Ala Ser Thr Gly
            270                 275                 280 atc gca gtt ttc aty gtc atc aca cag agc att ttg cta cty tgg gag     975
Ile Ala Val Phe Ile Val Ile Thr Gln Ser Ile Leu Leu Leu Trp Glu
        285                 290                 295 cag ttt gaa gac acc agt cac cac agc gca cat tca cac cgc agc tta    1023
Gln Phe Glu Asp Thr Ser His His Ser Ala His Ser His Arg Ser Leu
    300                 305                 310 gcc ggg ctc ttg ctg att gtc tta cgg atc tgc ctg gcg ctg tcg ctg    1071
Ala Gly Leu Leu Leu Ile Val Leu Arg Ile Cys Leu Ala Leu Ser Leu
315                 320                 325                 330 ggc tgc gga ctt tac cag gtc atc aca gtg gag agg agc gcg ctc aag    1119
Gly Cys Gly Leu Tyr Gln Val Ile Thr Val Glu Arg Ser Ala Leu Lys
                335                 340                 345 aga gag ttc tac atc acg ttt gcc aag ggc tgc atc ctg tgg ttc ttg    1167
Arg Glu Phe Tyr Ile Thr Phe Ala Lys Gly Cys Ile Leu Trp Phe Leu
            350                 355                 360 tgc cag cca gcg ctc gca tgc att gct gtc gct ttt aat gac tac caa    1215
Cys Gln Pro Ala Leu Ala Cys Ile Ala Val Ala Phe Asn Asp Tyr Gln
        365                 370                 375 aga gat aag ctt atc aca gta ggt gtc atc ctg tgt cag gcc gtg gcc    1263
Arg Asp Lys Leu Ile Thr Val Gly Val Ile Leu Cys Gln Ala Val Ala
    380                 385                 390 atg gtc att ctg tac aga ctt ttc ctg tcc cac agt ctt tac tgg gag    1311
Met Val Ile Leu Tyr Arg Leu Phe Leu Ser His Ser Leu Tyr Trp Glu
395                 400                 405                 410 gtc tcc tcg ctc tcc tca gta acg cta cca ctg acc atc tcg tct gca    1359
Val Ser Ser Leu Ser Ser Val Thr Leu Pro Leu Thr Ile Ser Ser Ala
                415                 420                 425 cac aga ggg cgc cct cat ttc tga tgcttgagtt ttgtggagag aaccagtgaa   1413
His Arg Gly Arg Pro His Phe
            430
```

-continued

```
tggagaagtg caataggatc caacgcagca ccgtcttgct gtgcctttgc gtgacagctg    1473
agcggtggaa gcaggcgtc ttatttatag aactgaacgt cagcgggctc agcagaaagg     1533
aatagaagct ccggagtgaa ctcaaacagt gaacttccca gaaagaatgt tgtttcaagg    1593
tgactgaaac agtttccacg tggaaataaa tgtgaaaagg actgcttaga gtacacgtgg    1653
gccaggtggt cacacctgcg atgcctcgtc actagcaaac tcaggcctga tagtcctaca    1713
gtattcacct agacaatact tgcctgtgcg tgcccagctc gcccagttat gaaatcagcg    1773
ggatgtgctg atttttaaaac tacttctttt tatcctttaa agaacgtgca tttcaaatta   1833
taatttaaag gacttgaaag tgaaattact taggaaataa atagaaaata tgttaacagt    1893
taaacgaaaa aaaaaaaaaa aaaaa                                          1918
```

<210> SEQ ID NO 6
<211> LENGTH: 433
<212> TYPE: PRT
<213> ORGANISM: Mus musculus
<220> FEATURE:
<221> NAME/KEY: misc_feature
<222> LOCATION: 130
<223> OTHER INFORMATION: Xaa is Tyr or His or Gln or Asn or Lys or
      Asp or Glu

<400> SEQUENCE: 6

```
Met Gly Gly Leu Arg Leu Leu Ala Val Ala Leu Thr Cys Ser Cys Trp
 1               5                  10                  15

Trp Pro Gln Gly Gly Gln Gly Lys Thr Leu Arg Gly Ser Phe Ser Ser
            20                  25                  30

Ala Ala Ala Arg Asp Ala Gln Gly Gln Ser Ile Gly His Phe Glu Phe
        35                  40                  45

His Arg Ile Asn Asn Val Ala Val Ala Val Gly Lys Glu Ala Lys Leu
    50                  55                  60

Tyr Leu Phe Gln Ala Gln Glu Trp Leu Lys Leu Glu Ser Ser Pro
65                  70                  75                  80

Gly Tyr Ser Cys Ser Glu Arg Leu Ala Arg Ala Gln Leu Thr Val Thr
                85                  90                  95

Val Thr Gln Thr Glu His Asn Leu Thr Val Ser Gln Leu Pro Ala Pro
            100                 105                 110

Gln Thr Trp Arg Val Phe Tyr Ala Asp Lys Phe Thr Cys Arg Asp Asp
        115                 120                 125

Ser Xaa Ser Pro Gln Gly Glu Glu Ile Pro Phe Glu Met Val Leu Leu
    130                 135                 140

Asn Pro Asp Ala Glu Gly Asn Pro Leu Asp His Phe Ser Ala Arg Glu
145                 150                 155                 160

Ser Gly Leu His Glu Phe Phe Leu Leu Val Leu Tyr Phe Val
                165                 170                 175

Thr Ala Cys Ile Tyr Ala Gln Ser Leu Trp Gln Ala Met Lys Lys Gly
            180                 185                 190

Gly Pro Met His Thr Ile Leu Lys Val Leu Thr Thr Ala Leu Leu Leu
        195                 200                 205

Gln Ala Ala Ser Ala Leu Ala Asn Tyr Ile His Leu Ser Arg Tyr Ser
    210                 215                 220

Arg Asp Gly Leu Gly Val Pro Leu Ile Gly Ser Leu Ala Glu Val Phe
225                 230                 235                 240

Asp Ile Ala Ser Gln Ile Gln Met Leu Tyr Leu Leu Ser Leu Cys
                245                 250                 255
```

```
Met Gly Trp Thr Ile Val Arg Met Lys Lys Ser Gln Ser Arg Pro Leu
            260                 265                 270
Gln Trp Asp Ser Thr Pro Ala Ser Thr Gly Ile Ala Val Phe Ile Val
        275                 280                 285
Ile Thr Gln Ser Ile Leu Leu Leu Trp Glu Gln Phe Glu Asp Thr Ser
    290                 295                 300
His His Ser Ala His Ser His Arg Ser Leu Ala Gly Leu Leu Leu Ile
305                 310                 315                 320
Val Leu Arg Ile Cys Leu Ala Leu Ser Leu Gly Cys Gly Leu Tyr Gln
                325                 330                 335
Val Ile Thr Val Glu Arg Ser Ala Leu Lys Arg Glu Phe Tyr Ile Thr
            340                 345                 350
Phe Ala Lys Gly Cys Ile Leu Trp Phe Leu Cys Gln Pro Ala Leu Ala
        355                 360                 365
Cys Ile Ala Val Ala Phe Asn Asp Tyr Gln Arg Asp Lys Leu Ile Thr
    370                 375                 380
Val Gly Val Ile Leu Cys Gln Ala Val Ala Met Val Ile Leu Tyr Arg
385                 390                 395                 400
Leu Phe Leu Ser His Ser Leu Tyr Trp Glu Val Ser Ser Leu Ser Ser
                405                 410                 415
Val Thr Leu Pro Leu Thr Ile Ser Ser Ala His Arg Gly Arg Pro His
            420                 425                 430
Phe
```

<210> SEQ ID NO 7
<211> LENGTH: 2857
<212> TYPE: DNA
<213> ORGANISM: Oryctolagus cuniculus
<220> FEATURE:
<221> NAME/KEY: CDS
<222> LOCATION: (415)..(2199)
<221> NAME/KEY: misc_feature
<222> LOCATION: (745)..(747)
<223> OTHER INFORMATION: Xaa is Met or Leu

<400> SEQUENCE: 7

```
gtgttactgt gtttcactaa atgtttgaag gctgtcggac ttttttgaatc atatgatctc      60 ctgaaagtag ttcacattgt tcagttcgtt tttatattaa aacttgggac tgcatttttt     120
atggttttgt ttcaaaagcc attttcttct gggaaaacta ttaccaaaca ccagtggatc     180
acaatattta aacatgcagt tgccgggtgt atcatttcac tcttgtggtt ttttggcctt     240 acccttttgtg gaccactaag gactttgctg ctgtttgaac acagtgaaat tgttgtcatc     300
tcgctcctca gtgttttgtt caccagttct ggaggaggac cagcaaagac aagaggggct     360
gcttttttca tcattgctgt gatctgttta ttgcttttttg acaatgatga ctctc atg     417
                                                                 Met
                                                                  1 gct aaa atg gca gaa cac cct gaa gga cat cat gac agt gct cta act      465
Ala Lys Met Ala Glu His Pro Glu Gly His His Asp Ser Ala Leu Thr
        5                  10                  15 cac atg ctt tac aca gcc att gcc ttc tta ggt gtg gca gat cac aag      513
His Met Leu Tyr Thr Ala Ile Ala Phe Leu Gly Val Ala Asp His Lys
     20                  25                  30 ggt gga gta ttg ttg cta gta ctg gct ttg tgt tgt aaa gtt ggt ttt      561
Gly Gly Val Leu Leu Leu Val Leu Ala Leu Cys Cys Lys Val Gly Phe
 35                  40                  45 cac aca gct tcc aga aaa ctc tct ata gat gtt ggg gga gcc aaa cgt      609
His Thr Ala Ser Arg Lys Leu Ser Ile Asp Val Gly Gly Ala Lys Arg
```

-continued

| | | | | | | | | | | | | | | | | |
|---|---|---|---|---|---|---|---|---|---|---|---|---|---|---|---|---|
| | 50 | | | | 55 | | | | 60 | | | | 65 | | | |
| ctt | caa | gct | tta | tcc | cat | ctt | gtt | tct | gtg | ctt | ctc | ttg | tgc | cca | tgg | 657 |
| Leu | Gln | Ala | Leu | Ser | His | Leu | Val | Ser | Val | Leu | Leu | Leu | Cys | Pro | Trp | |
| | | | | 70 | | | | | 75 | | | | | 80 | | |
| gtc | att | gtt | ctt | tct | atg | aca | act | gag | agt | aaa | gtt | gag | tct | tgg | ttt | 705 |
| Val | Ile | Val | Leu | Ser | Met | Thr | Thr | Glu | Ser | Lys | Val | Glu | Ser | Trp | Phe | |
| | | | | 85 | | | | | 90 | | | | | 95 | | |
| tct | ctc | att | atg | cct | ttc | acg | atg | gtt | att | ttt | ttt | gtc | wtg | atc | ctg | 753 |
| Ser | Leu | Ile | Met | Pro | Phe | Thr | Met | Val | Ile | Phe | Phe | Val | Xaa | Ile | Leu | |
| | | | 100 | | | | | 105 | | | | | 110 | | | |
| gat | ttc | tac | gtg | gat | tcc | att | tgt | tca | gtc | aaa | atg | gaa | gtt | tcc | aaa | 801 |
| Asp | Phe | Tyr | Val | Asp | Ser | Ile | Cys | Ser | Val | Lys | Met | Glu | Val | Ser | Lys | |
| | | 115 | | | | | 120 | | | | | 125 | | | | |
| tgt | gcc | cgc | tat | gga | tcc | ttg | ccc | att | ttt | att | agt | gct | ctc | ctt | ttt | 849 |
| Cys | Ala | Arg | Tyr | Gly | Ser | Leu | Pro | Ile | Phe | Ile | Ser | Ala | Leu | Leu | Phe | |
| 130 | | | | | 135 | | | | | 140 | | | | | 145 | |
| gga | aat | ttc | tgg | acc | cac | ccc | ata | act | gac | cag | ctt | cgg | gca | atg | agc | 897 |
| Gly | Asn | Phe | Trp | Thr | His | Pro | Ile | Thr | Asp | Gln | Leu | Arg | Ala | Met | Ser | |
| | | | | 150 | | | | | 155 | | | | | 160 | | |
| aga | gca | gca | cac | cag | ggg | agc | acg | gaa | cac | gtt | ctg | tct | gga | gga | gtg | 945 |
| Arg | Ala | Ala | His | Gln | Gly | Ser | Thr | Glu | His | Val | Leu | Ser | Gly | Gly | Val | |
| | | | 165 | | | | | 170 | | | | | 175 | | | |
| gtc | gtg | agc | gca | gtg | ttc | ttc | atc | ttg | tct | gcc | aac | atc | ctg | tca | tct | 993 |
| Val | Val | Ser | Ala | Val | Phe | Phe | Ile | Leu | Ser | Ala | Asn | Ile | Leu | Ser | Ser | |
| | | 180 | | | | | 185 | | | | | 190 | | | | |
| cct | tcg | aag | agg | ggg | cag | aag | ggc | acc | ctg | att | gga | tac | tct | cct | gaa | 1041 |
| Pro | Ser | Lys | Arg | Gly | Gln | Lys | Gly | Thr | Leu | Ile | Gly | Tyr | Ser | Pro | Glu | |
| | 195 | | | | | 200 | | | | | 205 | | | | | |
| gga | gca | cct | ctt | tac | aac | ttc | atg | ggg | gat | gct | ttt | cag | cac | agc | tca | 1089 |
| Gly | Ala | Pro | Leu | Tyr | Asn | Phe | Met | Gly | Asp | Ala | Phe | Gln | His | Ser | Ser | |
| 210 | | | | | 215 | | | | | 220 | | | | | 225 | |
| cag | tcc | gtg | cct | cgg | ttt | att | aag | gaa | tcg | ctg | aaa | cag | att | ctt | gag | 1137 |
| Gln | Ser | Val | Pro | Arg | Phe | Ile | Lys | Glu | Ser | Leu | Lys | Gln | Ile | Leu | Glu | |
| | | | | 230 | | | | | 235 | | | | | 240 | | |
| gag | agt | gac | tct | agg | cag | atc | ttt | tac | ttc | ttg | tgc | ttg | aat | ctg | ctt | 1185 |
| Glu | Ser | Asp | Ser | Arg | Gln | Ile | Phe | Tyr | Phe | Leu | Cys | Leu | Asn | Leu | Leu | |
| | | | 245 | | | | | 250 | | | | | 255 | | | |
| ttt | acc | ttt | gtg | gaa | tta | ttc | tat | gga | gtg | ctg | acg | aat | agt | ctg | ggt | 1233 |
| Phe | Thr | Phe | Val | Glu | Leu | Phe | Tyr | Gly | Val | Leu | Thr | Asn | Ser | Leu | Gly | |
| | | 260 | | | | | 265 | | | | | 270 | | | | |
| ctg | atc | tca | gat | ggc | ttt | cac | atg | ctc | ttt | gac | tgc | tct | gcc | ttg | gtc | 1281 |
| Leu | Ile | Ser | Asp | Gly | Phe | His | Met | Leu | Phe | Asp | Cys | Ser | Ala | Leu | Val | |
| | 275 | | | | | 280 | | | | | 285 | | | | | |
| atg | gga | ctt | ttt | gct | gcc | ctg | atg | agt | aga | tgg | aaa | gca | act | cgg | att | 1329 |
| Met | Gly | Leu | Phe | Ala | Ala | Leu | Met | Ser | Arg | Trp | Lys | Ala | Thr | Arg | Ile | |
| 290 | | | | | 295 | | | | | 300 | | | | | 305 | |
| ttc | tcc | tac | ggg | tat | ggc | cga | ata | gaa | att | ctt | tct | gga | ttt | att | aat | 1377 |
| Phe | Ser | Tyr | Gly | Tyr | Gly | Arg | Ile | Glu | Ile | Leu | Ser | Gly | Phe | Ile | Asn | |
| | | | | 310 | | | | | 315 | | | | | 320 | | |
| gga | ctt | ttt | cta | ata | gta | ata | gct | ttt | ttt | gtg | ttt | atg | gag | tca | gtt | 1425 |
| Gly | Leu | Phe | Leu | Ile | Val | Ile | Ala | Phe | Phe | Val | Phe | Met | Glu | Ser | Val | |
| | | | 325 | | | | | 330 | | | | | 335 | | | |
| gcc | aga | ttg | att | gat | cct | ccg | gaa | tta | gac | aca | aac | atg | cta | aca | cca | 1473 |
| Ala | Arg | Leu | Ile | Asp | Pro | Pro | Glu | Leu | Asp | Thr | Asn | Met | Leu | Thr | Pro | |
| | | 340 | | | | | 345 | | | | | 350 | | | | |
| gtg | tca | gtt | gga | ggg | ctg | ata | gta | aac | ctt | att | ggt | atc | tgt | gcc | ttt | 1521 |
| Val | Ser | Val | Gly | Gly | Leu | Ile | Val | Asn | Leu | Ile | Gly | Ile | Cys | Ala | Phe | |
| | 355 | | | | | 360 | | | | | 365 | | | | | |
| agc | cac | gcc | cat | aat | cac | acc | cat | gga | tct | tcc | caa | gga | agc | tgt | cac | 1569 |

```
Ser His Ala His Asn His Thr His Gly Ser Ser Gln Gly Ser Cys His
370                 375                 380                 385 tca tcc gat cac agc cat tca cac cac atg cat gga cac agt gac cat    1617
Ser Ser Asp His Ser His Ser His His Met His Gly His Ser Asp His
            390                 395                 400 gga cat ggt cac agc cat gga tcc cca ggc ggc ggc atg aat gct aac    1665
Gly His Gly His Ser His Gly Ser Pro Gly Gly Gly Met Asn Ala Asn
        405                 410                 415 atg agg ggt gtg ttt ttc cat gtt ttg gca gac acg ctt ggc agt att    1713
Met Arg Gly Val Phe Phe His Val Leu Ala Asp Thr Leu Gly Ser Ile
    420                 425                 430 ggt gtg att gta ttt aca gtt ttt ata gag cag ttt ggg tgg ttc att    1761
Gly Val Ile Val Phe Thr Val Phe Ile Glu Gln Phe Gly Trp Phe Ile
435                 440                 445 gcg gat ccc ctc tgt tct ctc ttt att gct gta tta ata ttt ctc agt    1809
Ala Asp Pro Leu Cys Ser Leu Phe Ile Ala Val Leu Ile Phe Leu Ser
450                 455                 460                 465 gtt gtc cca ctg atc aaa gat gcc tgt cag gtt cta ctt ttg aga ctg    1857
Val Val Pro Leu Ile Lys Asp Ala Cys Gln Val Leu Leu Leu Arg Leu
            470                 475                 480 cca cca gag tat gaa aaa gaa cta cat att gct tta gaa aag ata caa    1905
Pro Pro Glu Tyr Glu Lys Glu Leu His Ile Ala Leu Glu Lys Ile Gln
        485                 490                 495 aaa att gar gga tta ata tca tac cga gat cct cat ttc tgg cgc cat    1953
Lys Ile Glu Gly Leu Ile Ser Tyr Arg Asp Pro His Phe Trp Arg His
    500                 505                 510 tct gcc agt att gtg gca gga aca att cat ata caa gtg aca tct gat    2001
Ser Ala Ser Ile Val Ala Gly Thr Ile His Ile Gln Val Thr Ser Asp
515                 520                 525 gtg cta gaa caa aga ata gta cag cag gtt aca gga ata ctt aaa gat    2049
Val Leu Glu Gln Arg Ile Val Gln Gln Val Thr Gly Ile Leu Lys Asp
530                 535                 540                 545 gca gga gta aac aat tta aca att caa gta gaa aaa gaa gca tac ttt    2097
Ala Gly Val Asn Asn Leu Thr Ile Gln Val Glu Lys Glu Ala Tyr Phe
            550                 555                 560 caa cat atg tct ggc cta agt act gga ttt cat gat gtt ctg gct atg    2145
Gln His Met Ser Gly Leu Ser Thr Gly Phe His Asp Val Leu Ala Met
        565                 570                 575 aca aaa caa atg gag tcc atg aaa tac tgc aag gat ggc act tac att    2193
Thr Lys Gln Met Glu Ser Met Lys Tyr Cys Lys Asp Gly Thr Tyr Ile
    580                 585                 590 atg tga gagaactcac agattacccc cgatgtgagc agtgaagatt cagtgactca    2249
Met
595 gtgttgtaac attgccagca ggacagaaac tgcgtgtaat tgtacagaga ttttaaagct    2309 ccctattctt ggatcaagga ctctttccta aaggaaattt aaatattgat tgaaacattg    2369 atcacacagt aaaatagtga tttgagttat gtattttaaa tgactcttac aatttgaaca    2429 taatgtgtct catcatcttc agaaatggac acaatgatgg attctaatga agaccaaaag    2489 tacttctgtg tttcctttct gtcagaaagc atctccattg taaatatgta tttacatgtt    2549 tattacaaag atccaaatga aaaatttta gtccattttt tgcatagcct aaagataaaa    2609 taggaataaa agttctatat ttatgaattt tctgtacata aaactggttt ctaattataa    2669 ctgaagtcca ctgggtaaaa tctgtattgc caccttaaat gtaaactaaa ttatttgaga    2729 gaaacttcaa ccactgatat gacataagca gtgagaacag ggagtctata acattacagt    2789 tttggatgtt accaaaacca accactctgt aaaataaatt ttttactttt gtcaaaaaaa    2849
```

-continued aaaaaaaa                                                                 2857

<210> SEQ ID NO 8
<211> LENGTH: 594
<212> TYPE: PRT
<213> ORGANISM: Oryctolagus cuniculus
<220> FEATURE:
<221> NAME/KEY: misc_feature
<222> LOCATION: 111
<223> OTHER INFORMATION: Xaa is Met or Leu

<400> SEQUENCE: 8

```
Met Ala Lys Met Ala Glu His Pro Glu Gly His His Asp Ser Ala Leu
  1               5                  10                  15

Thr His Met Leu Tyr Thr Ala Ile Ala Phe Leu Gly Val Ala Asp His
             20                  25                  30

Lys Gly Gly Val Leu Leu Leu Val Leu Ala Leu Cys Cys Lys Val Gly
         35                  40                  45

Phe His Thr Ala Ser Arg Lys Leu Ser Ile Asp Val Gly Gly Ala Lys
     50                  55                  60

Arg Leu Gln Ala Leu Ser His Leu Val Ser Val Leu Leu Leu Cys Pro
 65                  70                  75                  80

Trp Val Ile Val Leu Ser Met Thr Thr Glu Ser Lys Val Glu Ser Trp
                 85                  90                  95

Phe Ser Leu Ile Met Pro Phe Thr Met Val Ile Phe Val Xaa Ile
            100                 105                 110

Leu Asp Phe Tyr Val Asp Ser Ile Cys Ser Val Lys Met Glu Val Ser
        115                 120                 125

Lys Cys Ala Arg Tyr Gly Ser Leu Pro Ile Phe Ile Ser Ala Leu Leu
    130                 135                 140

Phe Gly Asn Phe Trp Thr His Pro Ile Thr Asp Gln Leu Arg Ala Met
145                 150                 155                 160

Ser Arg Ala Ala His Gln Gly Ser Thr Glu His Val Leu Ser Gly Gly
                165                 170                 175

Val Val Val Ser Ala Val Phe Phe Ile Leu Ser Ala Asn Ile Leu Ser
            180                 185                 190

Ser Pro Ser Lys Arg Gly Gln Lys Gly Thr Leu Ile Gly Tyr Ser Pro
        195                 200                 205

Glu Gly Ala Pro Leu Tyr Asn Phe Met Gly Asp Ala Phe Gln His Ser
    210                 215                 220

Ser Gln Ser Val Pro Arg Phe Ile Lys Glu Ser Leu Lys Gln Ile Leu
225                 230                 235                 240

Glu Glu Ser Asp Ser Arg Gln Ile Phe Tyr Phe Leu Cys Leu Asn Leu
                245                 250                 255

Leu Phe Thr Phe Val Glu Leu Phe Tyr Gly Val Leu Thr Asn Ser Leu
            260                 265                 270

Gly Leu Ile Ser Asp Gly Phe His Met Leu Phe Asp Cys Ser Ala Leu
        275                 280                 285

Val Met Gly Leu Phe Ala Ala Leu Met Ser Arg Trp Lys Ala Thr Arg
    290                 295                 300

Ile Phe Ser Tyr Gly Tyr Gly Arg Ile Glu Ile Leu Ser Gly Phe Ile
305                 310                 315                 320

Asn Gly Leu Phe Leu Ile Val Ile Ala Phe Phe Val Phe Met Glu Ser
                325                 330                 335

Val Ala Arg Leu Ile Asp Pro Pro Glu Leu Asp Thr Asn Met Leu Thr
            340                 345                 350
```

Pro Val Ser Val Gly Gly Leu Ile Val Asn Leu Ile Gly Ile Cys Ala
            355                 360                 365

Phe Ser His Ala His Asn His Thr His Gly Ser Ser Gln Gly Ser Cys
        370                 375                 380

His Ser Ser Asp His Ser His Ser His Met His Gly His Ser Asp
385                 390                 395                 400

His Gly His Gly His Ser His Gly Ser Pro Gly Gly Gly Met Asn Ala
                405                 410                 415

Asn Met Arg Gly Val Phe Phe His Val Leu Ala Asp Thr Leu Gly Ser
            420                 425                 430

Ile Gly Val Ile Val Phe Thr Val Phe Ile Glu Gln Phe Gly Trp Phe
        435                 440                 445

Ile Ala Asp Pro Leu Cys Ser Leu Phe Ile Ala Val Leu Ile Phe Leu
    450                 455                 460

Ser Val Val Pro Leu Ile Lys Asp Ala Cys Gln Val Leu Leu Leu Arg
465                 470                 475                 480

Leu Pro Pro Glu Tyr Glu Lys Glu Leu His Ile Ala Leu Glu Lys Ile
                485                 490                 495

Gln Lys Ile Glu Gly Leu Ile Ser Tyr Arg Asp Pro His Phe Trp Arg
            500                 505                 510

His Ser Ala Ser Ile Val Ala Gly Thr Ile His Ile Gln Val Thr Ser
        515                 520                 525

Asp Val Leu Glu Gln Arg Ile Val Gln Val Thr Gly Ile Leu Lys
    530                 535                 540

Asp Ala Gly Val Asn Asn Leu Thr Ile Gln Val Glu Lys Glu Ala Tyr
545                 550                 555                 560

Phe Gln His Met Ser Gly Leu Ser Thr Gly Phe His Asp Val Leu Ala
                565                 570                 575

Met Thr Lys Gln Met Glu Ser Met Lys Tyr Cys Lys Asp Gly Thr Tyr
            580                 585                 590

Ile Met

<210> SEQ ID NO 9
<211> LENGTH: 2519
<212> TYPE: DNA
<213> ORGANISM: Homo sapiens
<220> FEATURE:
<221> NAME/KEY: CDS
<222> LOCATION: (1)..(1785)
<221> NAME/KEY: misc_feature
<222> LOCATION: (289)..(291)
<223> OTHER INFORMATION: Xaa is Phe or Leu
<221> NAME/KEY: misc_feature
<222> LOCATION: (1015)..(1017)
<223> OTHER INFORMATION: Xaa is Lys or Arg
<221> NAME/KEY: misc_feature
<222> LOCATION: (1492)..(1494)
<223> OTHER INFORMATION: n is a or g or c or t
    Xaa is Gln or Lys or Glu
<221> NAME/KEY: misc_feature
<222> LOCATION: (1540)..(1542), (1582)..(1584), (1693)..(1695)
<223> OTHER INFORMATION: Xaa is Phe or Ser
<221> NAME/KEY: misc_feature
<222> LOCATION: (1609)..(1611)
<223> OTHER INFORMATION: Xaa is Gln or Arg
<221> NAME/KEY: misc_feature
<222> LOCATION: 2493, 2516
<223> OTHER INFORMATION: n is a or g or c or t

<400> SEQUENCE: 9 atg gct aaa atg gct gaa cac cct gaa gga cat cat gac agt gct cta        48

```
Met Ala Lys Met Ala Glu His Pro Glu Gly His His Asp Ser Ala Leu
 1               5                  10                  15 act cat atg ctt tac aca gcc att gcc ttc tta ggt gtg gca gat cac    96
Thr His Met Leu Tyr Thr Ala Ile Ala Phe Leu Gly Val Ala Asp His
             20                  25                  30 aag ggt gga gta tta ttg cta gta ctg gct ttg tgt tgt aaa gtt ggt   144
Lys Gly Gly Val Leu Leu Leu Val Leu Ala Leu Cys Cys Lys Val Gly
         35                  40                  45 ttt cat aca gct tcc aga aag ctc tct gtc gac gtt ggt gga gct aaa   192
Phe His Thr Ala Ser Arg Lys Leu Ser Val Asp Val Gly Gly Ala Lys
     50                  55                  60 cgt ctt caa gct tta tct cat ctt gtt tct gtg ctt ctc ttg tgc cca   240
Arg Leu Gln Ala Leu Ser His Leu Val Ser Val Leu Leu Leu Cys Pro
 65                  70                  75                  80 tgg gtc att gtt ctt tct gtg aca act gag agt aaa gtg gag tct tgg   288
Trp Val Ile Val Leu Ser Val Thr Thr Glu Ser Lys Val Glu Ser Trp
                 85                  90                  95 ytt tct ctc att atg cct ttt gca acg gtt atc ttt ttt gtc atg atc   336
Xaa Ser Leu Ile Met Pro Phe Ala Thr Val Ile Phe Phe Val Met Ile
             100                 105                 110 ctg gat ttc tac gtg gat tcc att tgt tca gtc aaa atg gaa gtt tcc   384
Leu Asp Phe Tyr Val Asp Ser Ile Cys Ser Val Lys Met Glu Val Ser
         115                 120                 125 aaa tgt gct cgt tat gga tcc ttt ccc att ttt att agt gct ctc ctt   432
Lys Cys Ala Arg Tyr Gly Ser Phe Pro Ile Phe Ile Ser Ala Leu Leu
     130                 135                 140 ttt gga aat ttt tgg aca cat cca ata aca gac cag ctt cgg gct atg   480
Phe Gly Asn Phe Trp Thr His Pro Ile Thr Asp Gln Leu Arg Ala Met
145                 150                 155                 160 aac aaa gca gca cac cag gag agc act gaa cac gtc ctg tct gga gga   528
Asn Lys Ala Ala His Gln Glu Ser Thr Glu His Val Leu Ser Gly Gly
                 165                 170                 175 gtg gta gtg agt gct ata ttc ttc att ttg tct gcc aat atc tta tca   576
Val Val Val Ser Ala Ile Phe Phe Ile Leu Ser Ala Asn Ile Leu Ser
             180                 185                 190 tct ccc tct aag aga gga caa aaa ggt acc ctt att gga tat tct cct   624
Ser Pro Ser Lys Arg Gly Gln Lys Gly Thr Leu Ile Gly Tyr Ser Pro
         195                 200                 205 gaa gga aca cct ctt tat aac ttc atg ggt gat gct ttt cag cat agc   672
Glu Gly Thr Pro Leu Tyr Asn Phe Met Gly Asp Ala Phe Gln His Ser
     210                 215                 220 tct caa tcg atc cct agg ttt att aag gaa tca cta aaa caa att ctt   720
Ser Gln Ser Ile Pro Arg Phe Ile Lys Glu Ser Leu Lys Gln Ile Leu
225                 230                 235                 240 gag gag agt gac tct agg cag atc ttt tac ttc ttg tgc ttg aat ctg   768
Glu Glu Ser Asp Ser Arg Gln Ile Phe Tyr Phe Leu Cys Leu Asn Leu
                 245                 250                 255 ctt ttt acc ttt gtg gaa tta ttc tat ggc gtg ctg acc aat agt ctg   816
Leu Phe Thr Phe Val Glu Leu Phe Tyr Gly Val Leu Thr Asn Ser Leu
             260                 265                 270 ggc ctg atc tcg gat gga ttc cac atg ctt ttt gac tgc tct gct tta   864
Gly Leu Ile Ser Asp Gly Phe His Met Leu Phe Asp Cys Ser Ala Leu
         275                 280                 285 gtc atg gga ctt ttt gct gcc ctg atg agt agg tgg aaa gcc act cgg   912
Val Met Gly Leu Phe Ala Ala Leu Met Ser Arg Trp Lys Ala Thr Arg
     290                 295                 300 att ttc tcc tat ggg tac ggc cga ata gaa att ctg tct gga ttt att   960
Ile Phe Ser Tyr Gly Tyr Gly Arg Ile Glu Ile Leu Ser Gly Phe Ile
305                 310                 315                 320
```

-continued

```
aat gga ctt ttt cta ata gta ata gcg ttt ttt gtg ttt atg gag tca    1008
Asn Gly Leu Phe Leu Ile Val Ile Ala Phe Phe Val Phe Met Glu Ser
            325                 330                 335 gtg gct ara ttg att gat cct cca gaa tta gac act cac atg tta aca    1056
Val Ala Xaa Leu Ile Asp Pro Pro Glu Leu Asp Thr His Met Leu Thr
        340                 345                 350 cca gty tca gtt gga ggg ctg ata gta aac ctt att ggt atc tgt gcc    1104
Pro Val Ser Val Gly Gly Leu Ile Val Asn Leu Ile Gly Ile Cys Ala
    355                 360                 365 ttt agc cat gcc cat agc cat gcc cat gga gct tct caa gga agc tgt    1152
Phe Ser His Ala His Ser His Ala His Gly Ala Ser Gln Gly Ser Cys
370                 375                 380 cac tca tct gat cac agc cat tca cay cat atg cat gga cac agt gac    1200
His Ser Ser Asp His Ser His Ser His His Met His Gly His Ser Asp
385                 390                 395                 400 cat ggg cat ggt cac agc cac gga tct gcg ggt gga ggc atg aat gct    1248
His Gly His Gly His Ser His Gly Ser Ala Gly Gly Gly Met Asn Ala
                405                 410                 415 aac atg agg ggt gta ttt yta cat gtt ttg gca gat acw ctt ggc agc    1296
Asn Met Arg Gly Val Phe Leu His Val Leu Ala Asp Thr Leu Gly Ser
            420                 425                 430 att ggt gtg att gta tcc aca gtt ttt ata gag cag ttt gga tgg ttc    1344
Ile Gly Val Ile Val Ser Thr Val Phe Ile Glu Gln Phe Gly Trp Phe
        435                 440                 445 atc gct gac cca ctc tgt tct ctt ttt att gct ata tta ata ttt ctc    1392
Ile Ala Asp Pro Leu Cys Ser Leu Phe Ile Ala Ile Leu Ile Phe Leu
    450                 455                 460 agt gtt gtt cca ctg att aaa gat gcc tgc cag gtt tta ctc ctg aga    1440
Ser Val Val Pro Leu Ile Lys Asp Ala Cys Gln Val Leu Leu Leu Arg
465                 470                 475                 480 ttg cca cca gaa tat gga aaa gaa cta cat att gct tta gaa aag ata    1488
Leu Pro Pro Glu Tyr Gly Lys Glu Leu His Ile Ala Leu Glu Lys Ile
                485                 490                 495 cag naa att gaa gga tta ata tca tac cga gac cct cat ttt tgg cgt    1536
Gln Xaa Ile Glu Gly Leu Ile Ser Tyr Arg Asp Pro His Phe Trp Arg
            500                 505                 510 cat tyt gct agt att gtg gca gga aca att cat ata cag gtg aca tyt    1584
His Xaa Ala Ser Ile Val Ala Gly Thr Ile His Ile Gln Val Thr Xaa
        515                 520                 525 gat gtg cta gaa caa aga ata gta crg cag gtt aca gga ata ctt aaa    1632
Asp Val Leu Glu Gln Arg Ile Val Xaa Gln Val Thr Gly Ile Leu Lys
    530                 535                 540 gat gct gga gta aac aat tta aca att caa gtg gaa aag gag gca tac    1680
Asp Ala Gly Val Asn Asn Leu Thr Ile Gln Val Glu Lys Glu Ala Tyr
545                 550                 555                 560 ttt caa cat atg tyt ggc cta agt act gga ttt cat gat gtt ctg gct    1728
Phe Gln His Met Xaa Gly Leu Ser Thr Gly Phe His Asp Val Leu Ala
                565                 570                 575 atg aca aaa caa atg gaa tcc atg aaa tac tgc aaa gat ggt act tac    1776
Met Thr Lys Gln Met Glu Ser Met Lys Tyr Cys Lys Asp Gly Thr Tyr
            580                 585                 590 atc atg tga gataactcaa gaattacccc tggagaataa acaatgaaga            1825
Ile Met
    595 ttaaatgact cagtatttgt aatattgcca gaaggataaa aattacacat taactgtaca   1885 gaaacagagt tccctactac tggatcaagg aatctttctt gaaggaaatt taaatacaga   1945 atgaaacatt aatggtaaaa gtggagtaat tatttaaatt atgtgtataa aaggaatcaa   2005 attttgagta acatgatgt attacatcat cttcaaaaat agatatgatg gattctagtg    2065
```

-continued

```
aagaccaaaa ttacttctgt ttactttcta tcaggaagca tctccattgt aaatatgtat    2125
ttacatgttt attacaaaga cccaaatgaa aaatttttag tccatttttt gcatagccta    2185
aagataaaat aggaataaaa gttctatatt tatgggattt tctgtatata aaactggttt    2245
ctaattataa cttaagtcca ttaagtaaaa tctgtattgc cactttaaat gtaaactaaa    2305
ttatttggga gaaacttcaa ccactgatat gagataagca atgagaatag ggaagtgtat    2365
aacatcacag tttttgatgt attacaaaaa tcaaccactt tataaaataa attttttta    2425 cttttggtaa aaaaaaaaaa aaaaaaaaaa aaaaaaaaaa aaaaaaaaag cggccgctga    2485
attctagnta gaattcagcg gccgctgaat ncta                                2519
```

<210> SEQ ID NO 10
<211> LENGTH: 594
<212> TYPE: PRT
<213> ORGANISM: Homo sapiens
<220> FEATURE:
<221> NAME/KEY: misc_feature
<222> LOCATION: 97
<223> OTHER INFORMATION: Xaa is Phe or Leu
<221> NAME/KEY: misc_feature
<222> LOCATION: 339
<223> OTHER INFORMATION: Xaa is Lys or Arg
<221> NAME/KEY: misc_feature
<222> LOCATION: 498
<223> OTHER INFORMATION: Xaa is Gln or Lys or Glu
<221> NAME/KEY: misc_feature
<222> LOCATION: 514, 528, 565
<223> OTHER INFORMATION: Xaa is Phe or Ser
<221> NAME/KEY: misc_feature
<222> LOCATION: 537
<223> OTHER INFORMATION: Xaa is Gln or Arg

<400> SEQUENCE: 10

```
Met Ala Lys Met Ala Glu His Pro Glu Gly His His Asp Ser Ala Leu
  1               5                  10                  15

Thr His Met Leu Tyr Thr Ala Ile Ala Phe Leu Gly Val Ala Asp His
                 20                  25                  30

Lys Gly Gly Val Leu Leu Leu Val Leu Ala Leu Cys Cys Lys Val Gly
             35                  40                  45

Phe His Thr Ala Ser Arg Lys Leu Ser Val Asp Val Gly Gly Ala Lys
         50                  55                  60

Arg Leu Gln Ala Leu Ser His Leu Val Ser Val Leu Leu Leu Cys Pro
 65                  70                  75                  80

Trp Val Ile Val Leu Ser Val Thr Thr Glu Ser Lys Val Glu Ser Trp
                 85                  90                  95

Xaa Ser Leu Ile Met Pro Phe Ala Thr Val Ile Phe Phe Val Met Ile
                100                 105                 110

Leu Asp Phe Tyr Val Asp Ser Ile Cys Ser Val Lys Met Glu Val Ser
            115                 120                 125

Lys Cys Ala Arg Tyr Gly Ser Phe Pro Ile Phe Ile Ser Ala Leu Leu
        130                 135                 140

Phe Gly Asn Phe Trp Thr His Pro Ile Thr Asp Gln Leu Arg Ala Met
145                 150                 155                 160

Asn Lys Ala Ala His Gln Glu Ser Thr Glu His Val Leu Ser Gly Gly
                165                 170                 175

Val Val Val Ser Ala Ile Phe Phe Ile Leu Ser Ala Asn Ile Leu Ser
            180                 185                 190

Ser Pro Ser Lys Arg Gly Gln Lys Gly Thr Leu Ile Gly Tyr Ser Pro
        195                 200                 205
```

-continued

```
Glu Gly Thr Pro Leu Tyr Asn Phe Met Gly Asp Ala Phe Gln His Ser
    210                 215                 220
Ser Gln Ser Ile Pro Arg Phe Ile Lys Glu Ser Leu Lys Gln Ile Leu
225                 230                 235                 240
Glu Glu Ser Asp Ser Arg Gln Ile Phe Tyr Phe Leu Cys Leu Asn Leu
                245                 250                 255
Leu Phe Thr Phe Val Glu Leu Phe Tyr Gly Val Leu Thr Asn Ser Leu
                260                 265                 270
Gly Leu Ile Ser Asp Gly Phe His Met Leu Phe Asp Cys Ser Ala Leu
            275                 280                 285
Val Met Gly Leu Phe Ala Ala Leu Met Ser Arg Trp Lys Ala Thr Arg
    290                 295                 300
Ile Phe Ser Tyr Gly Tyr Gly Arg Ile Glu Ile Leu Ser Gly Phe Ile
305                 310                 315                 320
Asn Gly Leu Phe Leu Ile Val Ile Ala Phe Phe Val Phe Met Glu Ser
                325                 330                 335
Val Ala Xaa Leu Ile Asp Pro Pro Glu Leu Asp Thr His Met Leu Thr
                340                 345                 350
Pro Val Ser Val Gly Gly Leu Ile Val Asn Leu Ile Gly Ile Cys Ala
            355                 360                 365
Phe Ser His Ala His Ser His Ala His Gly Ala Ser Gln Gly Ser Cys
    370                 375                 380
His Ser Ser Asp His Ser His Ser His His Met His Gly His Ser Asp
385                 390                 395                 400
His Gly His Gly His Ser His Gly Ser Ala Gly Gly Met Asn Ala
                405                 410                 415
Asn Met Arg Gly Val Phe Leu His Val Leu Ala Asp Thr Leu Gly Ser
                420                 425                 430
Ile Gly Val Ile Val Ser Thr Val Phe Ile Glu Gln Phe Gly Trp Phe
            435                 440                 445
Ile Ala Asp Pro Leu Cys Ser Leu Phe Ile Ala Ile Leu Ile Phe Leu
    450                 455                 460
Ser Val Val Pro Leu Ile Lys Asp Ala Cys Gln Val Leu Leu Leu Arg
465                 470                 475                 480
Leu Pro Pro Glu Tyr Gly Lys Glu Leu His Ile Ala Leu Glu Lys Ile
                485                 490                 495
Gln Xaa Ile Glu Gly Leu Ile Ser Tyr Arg Asp Pro His Phe Trp Arg
            500                 505                 510
His Xaa Ala Ser Ile Val Ala Gly Thr Ile His Ile Gln Val Thr Xaa
    515                 520                 525
Asp Val Leu Glu Gln Arg Ile Val Xaa Gln Val Thr Gly Ile Leu Lys
    530                 535                 540
Asp Ala Gly Val Asn Asn Leu Thr Ile Gln Val Glu Lys Glu Ala Tyr
545                 550                 555                 560
Phe Gln His Met Xaa Gly Leu Ser Thr Gly Phe His Asp Val Leu Ala
                565                 570                 575
Met Thr Lys Gln Met Glu Ser Met Lys Tyr Cys Lys Asp Gly Thr Tyr
                580                 585                 590
Ile Met
```

<210> SEQ ID NO 11
<211> LENGTH: 178
<212> TYPE: DNA

```
<213> ORGANISM: Oryctolagus cuniculus
<220> FEATURE:
<221> NAME/KEY: misc_feature
<222> LOCATION: 54, 68, 97
<223> OTHER INFORMATION: n is a or g or c or t

<400> SEQUENCE: 11
gttttttttt tttttcatac atttggtatg aaacatcgaa tagcaaaagc agancatgtt      60
tctgtatnac tgcatttaag cagtaccaaa actgaanaaa ggtaataact gaaatgtttt    120
aaaatacatg taaacaataa actttcagga aattctgttg ttaaaaaaaa aaaaaaac      178

<210> SEQ ID NO 12
<211> LENGTH: 167
<212> TYPE: DNA
<213> ORGANISM: Oryctolagus cuniculus

<400> SEQUENCE: 12
cttgattgcc accttaaatg taaactaaat tatttgagag aaacttcaac cactgatatg     60
acataagcag tgagaacagg gagtctataa cattacagtt ttggatgtta ccaaaaccaa   120
ccactctgta aaataaattt tttacttttg taaaaaaaaa aaaaaac                  167

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(24)

<400> SEQUENCE: 13
tcatacattt ggtatgaaac atcg                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(24)

<400> SEQUENCE: 14
tttttttaac aacagaattt cctg                                            24

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(27)

<400> SEQUENCE: 15
aatttcctga agtttattg tttacat                                          27

<210> SEQ ID NO 16
<211> LENGTH: 25
<212> TYPE: DNA
<213> ORGANISM: Artificial Sequence
<220> FEATURE:
```

```
<223> OTHER INFORMATION: Description of Artificial Sequence:an
      artificially synthesized primer sequence
<221> NAME/KEY: primer_bind
<222> LOCATION: (1)..(25)

<400> SEQUENCE: 16
gaaacatgct ctgcttttgc tattc                                          25

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(27)

<400> SEQUENCE: 17
atccctgcta agttgtggtg tgaatgg                                        27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(27)

<400> SEQUENCE: 18
tctgctttga gacttcttca tcctgac                                        27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(27)

<400> SEQUENCE: 19
ccatcctaat acgactcact atagggc                                        27

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(23)

<400> SEQUENCE: 20
actcactata gggctcgagc ggc                                            23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(22)
```

<400> SEQUENCE: 21
ttgattgcca ccttaaatgt aa                22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(22)

<400> SEQUENCE: 22
gtggttggtt ttggtaacat cc                22

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(25)

<400> SEQUENCE: 23
gttatagact ccctgttctc actgc             25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(25)

<400> SEQUENCE: 24
agactccctg ttctcactgc ttatg             25

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(27)

<400> SEQUENCE: 25
atcttcactg ctcacatcgg gggtaat           27

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(23)

<400> SEQUENCE: 26
tcactgctca catcggggt aat                23

<210> SEQ ID NO 27
<211> LENGTH: 1703
<212> TYPE: DNA
<213> ORGANISM: Mus musculus
<220> FEATURE:
<221> NAME/KEY: CDS
<222> LOCATION: (10)..(1701)

<400> SEQUENCE: 27

| | | | | | | | | | | | | | | |
|---|---|---|---|---|---|---|---|---|---|---|---|---|---|---|
| gatgatctc | atg | gca | aag | atg | gct | gaa | cac | ccg | gaa | gga | cat | cat | gat | agt | 51 |
| | Met | Ala | Lys | Met | Ala | Glu | His | Pro | Glu | Gly | His | His | Asp | Ser | |
| | 1 | | | 5 | | | | | 10 | | | | | | | gct cta act cac atg ctc tat aca gcc att gcc ttt tta ggg gtg gca    99
Ala Leu Thr His Met Leu Tyr Thr Ala Ile Ala Phe Leu Gly Val Ala
 15              20                  25                  30 gat cac aag ggt gga gta ctc ttg ctg gtg ctg gct tta tgt tgt aaa    147
Asp His Lys Gly Gly Val Leu Leu Leu Val Leu Ala Leu Cys Cys Lys
             35                  40                  45 gtt ggt ttt cat acg gct tcc aga aag ctc tct ata gat gtt ggt gga   195
Val Gly Phe His Thr Ala Ser Arg Lys Leu Ser Ile Asp Val Gly Gly
         50                  55                  60 gct aag cgc ctt cag gcc tta tct cag ctt gtt tct gtg ttt ctc ctg   243
Ala Lys Arg Leu Gln Ala Leu Ser Gln Leu Val Ser Val Phe Leu Leu
 65                  70                  75 tgc cca tgg gtg att gtc ctt tct gtg aca act gaa agt aag gtt gag   291
Cys Pro Trp Val Ile Val Leu Ser Val Thr Thr Glu Ser Lys Val Glu
         80                  85                  90 tct tgg ttc tct ctc atc atg cct ttc acc aca gtc atc ttt ttt gtc   339
Ser Trp Phe Ser Leu Ile Met Pro Phe Thr Thr Val Ile Phe Phe Val
 95                  100                 105                 110 atg atc ctg gat ttc tat atg gat tct gtt tgt tca gtc aaa atg gac   387
Met Ile Leu Asp Phe Tyr Met Asp Ser Val Cys Ser Val Lys Met Asp
             115                 120                 125 gtg tcc aaa tgt gcc cgc tat ggg tcc ttt ccc att ttt att agt gcc   435
Val Ser Lys Cys Ala Arg Tyr Gly Ser Phe Pro Ile Phe Ile Ser Ala
         130                 135                 140 ctc ctg ttt cga aat ttc tgg aca cac cca ata aca gac caa ctc cgg   483
Leu Leu Phe Arg Asn Phe Trp Thr His Pro Ile Thr Asp Gln Leu Arg
 145                 150                 155 gct atg aac aga gca gca cac cag gag agc aca gaa cac gtc ctg tct   531
Ala Met Asn Arg Ala Ala His Gln Glu Ser Thr Glu His Val Leu Ser
         160                 165                 170 gga gga gtg gta gtg agc gct gtg ttc ttc att ttg tcg gcc aac att   579
Gly Gly Val Val Val Ser Ala Val Phe Phe Ile Leu Ser Ala Asn Ile
 175                 180                 185                 190 cta tca tct ccc tct aag aga gga cag aaa ggt acc ctt att gga tat   627
Leu Ser Ser Pro Ser Lys Arg Gly Gln Lys Gly Thr Leu Ile Gly Tyr
             195                 200                 205 tct cct gaa gga aca cca ctc tat cac ttc atg ggg gac gct ttt cag   675
Ser Pro Glu Gly Thr Pro Leu Tyr His Phe Met Gly Asp Ala Phe Gln
         210                 215                 220 cac agc tct cag tcg gtg cct agg ttc att aag gac tca cta aag cag   723
His Ser Ser Gln Ser Val Pro Arg Phe Ile Lys Asp Ser Leu Lys Gln
         225                 230                 235 gtt ctc gag gag agc gac tct agg cag atc ttt tac ttc ttg tgc ttg   771
Val Leu Glu Glu Ser Asp Ser Arg Gln Ile Phe Tyr Phe Leu Cys Leu
     240                 245                 250 aat ctg ctt ttt acc ttt gtg gag ttg ttc tat ggc gtg cta acc aac   819
Asn Leu Leu Phe Thr Phe Val Glu Leu Phe Tyr Gly Val Leu Thr Asn
 255                 260                 265                 270

```
agt cta ggc ctg atc tca gat gga ttt cac atg ctc ttt gac tgc tcg      867
Ser Leu Gly Leu Ile Ser Asp Gly Phe His Met Leu Phe Asp Cys Ser
                275                 280                 285 gct ttg gtc atg gga ctg ttt gct gcc ctg atg agc cgc tgg aaa gcc      915
Ala Leu Val Met Gly Leu Phe Ala Ala Leu Met Ser Arg Trp Lys Ala
            290                 295                 300 acc cgg att ttc tcc tat ggg tat ggc cga ata gag att ctc tct ggc      963
Thr Arg Ile Phe Ser Tyr Gly Tyr Gly Arg Ile Glu Ile Leu Ser Gly
        305                 310                 315 ttt att aat ggg ctt ttt ctg atc gtg ata gca ttt ttt gtg ttt atg     1011
Phe Ile Asn Gly Leu Phe Leu Ile Val Ile Ala Phe Phe Val Phe Met
    320                 325                 330 gaa tca gtg gct aga ctg atc gat cct ccg gaa cta gac aca aac atg     1059
Glu Ser Val Ala Arg Leu Ile Asp Pro Pro Glu Leu Asp Thr Asn Met
335                 340                 345                 350 ctg aca cca gtt tcc gtc gca ggg ctg ata gta aac ctt att ggt atc     1107
Leu Thr Pro Val Ser Val Ala Gly Leu Ile Val Asn Leu Ile Gly Ile
                355                 360                 365 tgt gcc ttc agc cac gcc cac agc cat ggc cat ggc gct tct caa gga     1155
Cys Ala Phe Ser His Ala His Ser His Gly His Gly Ala Ser Gln Gly
            370                 375                 380 aac tgc cac tct gat cac ggc cat tca cac cat gca cat gga cac ggc     1203
Asn Cys His Ser Asp His Gly His Ser His His Ala His Gly His Gly
        385                 390                 395 cat gat cac ggt cac agc cac ggc ttc acg ggt gga ggc atg aat gcg     1251
His Asp His Gly His Ser His Gly Phe Thr Gly Gly Gly Met Asn Ala
    400                 405                 410 aac atg agg ggt gta ttt ctc cat gtg ttg gca gac aca ctg ggc agc     1299
Asn Met Arg Gly Val Phe Leu His Val Leu Ala Asp Thr Leu Gly Ser
415                 420                 425                 430 atc ggc gtg att gtg tcc aca gtt ctc ata gag cag ttt gga tgg ttc     1347
Ile Gly Val Ile Val Ser Thr Val Leu Ile Glu Gln Phe Gly Trp Phe
                435                 440                 445 att gct gat ccc ctg tgt tct ctt ttt att gcc gtg ttg ata ttt ctc     1395
Ile Ala Asp Pro Leu Cys Ser Leu Phe Ile Ala Val Leu Ile Phe Leu
            450                 455                 460 agt gtg atc cca ctg att aaa gat gcc tgt caa gtt cta ctt ctg aga     1443
Ser Val Ile Pro Leu Ile Lys Asp Ala Cys Gln Val Leu Leu Leu Arg
        465                 470                 475 cta cca cct gac cat gaa aaa gaa ctg cat att gct tta gaa aag ata     1491
Leu Pro Pro Asp His Glu Lys Glu Leu His Ile Ala Leu Glu Lys Ile
    480                 485                 490 cag aaa att gag gga tta ata tca tac cga gac cct cat ttt tgg cgc     1539
Gln Lys Ile Glu Gly Leu Ile Ser Tyr Arg Asp Pro His Phe Trp Arg
495                 500                 505                 510 cat tct gcc agt att gta gcg gga aca att cat ata caa gtg aca tct     1587
His Ser Ala Ser Ile Val Ala Gly Thr Ile His Ile Gln Val Thr Ser
                515                 520                 525 gag gtg ctg gag cag aga att gta cag cag gtt aca ggg ata ctt aaa     1635
Glu Val Leu Glu Gln Arg Ile Val Gln Gln Val Thr Gly Ile Leu Lys
            530                 535                 540 gat gca gga gta aac aac cta acc ata caa gtg gaa aag gag gca tac     1683
Asp Ala Gly Val Asn Asn Leu Thr Ile Gln Val Glu Lys Glu Ala Tyr
        545                 550                 555 ttt cag cat atg tcc ggc ct                                          1703
Phe Gln His Met Ser Gly
    560
```

<210> SEQ ID NO 28

```
<211> LENGTH: 564
<212> TYPE: PRT
<213> ORGANISM: Mus musculus

<400> SEQUENCE: 28

Met Ala Lys Met Ala Glu His Pro Glu Gly His His Asp Ser Ala Leu
  1               5                  10                  15

Thr His Met Leu Tyr Thr Ala Ile Ala Phe Leu Gly Val Ala Asp His
             20                  25                  30

Lys Gly Gly Val Leu Leu Val Leu Ala Leu Cys Cys Lys Val Gly
         35                  40                  45

Phe His Thr Ala Ser Arg Lys Leu Ser Ile Asp Val Gly Gly Ala Lys
     50                  55                  60

Arg Leu Gln Ala Leu Ser Gln Leu Val Ser Val Phe Leu Leu Cys Pro
 65                  70                  75                  80

Trp Val Ile Val Leu Ser Val Thr Thr Glu Ser Lys Val Glu Ser Trp
                 85                  90                  95

Phe Ser Leu Ile Met Pro Phe Thr Thr Val Ile Phe Val Met Ile
                100                 105                 110

Leu Asp Phe Tyr Met Asp Ser Val Cys Ser Val Lys Met Asp Val Ser
            115                 120                 125

Lys Cys Ala Arg Tyr Gly Ser Phe Pro Ile Phe Ile Ser Ala Leu Leu
        130                 135                 140

Phe Arg Asn Phe Trp Thr His Pro Ile Thr Asp Gln Leu Arg Ala Met
145                 150                 155                 160

Asn Arg Ala Ala His Gln Glu Ser Thr Glu His Val Leu Ser Gly Gly
                165                 170                 175

Val Val Val Ser Ala Val Phe Phe Ile Leu Ser Ala Asn Ile Leu Ser
            180                 185                 190

Ser Pro Ser Lys Arg Gly Gln Lys Gly Thr Leu Ile Gly Tyr Ser Pro
        195                 200                 205

Glu Gly Thr Pro Leu Tyr His Phe Met Gly Asp Ala Phe Gln His Ser
    210                 215                 220

Ser Gln Ser Val Pro Arg Phe Ile Lys Asp Ser Leu Lys Gln Val Leu
225                 230                 235                 240

Glu Glu Ser Asp Ser Arg Gln Ile Phe Tyr Phe Leu Cys Leu Asn Leu
                245                 250                 255

Leu Phe Thr Phe Val Glu Leu Phe Tyr Gly Val Leu Thr Asn Ser Leu
            260                 265                 270

Gly Leu Ile Ser Asp Gly Phe His Met Leu Phe Asp Cys Ser Ala Leu
        275                 280                 285

Val Met Gly Leu Phe Ala Ala Leu Met Ser Arg Trp Lys Ala Thr Arg
    290                 295                 300

Ile Phe Ser Tyr Gly Tyr Gly Arg Ile Glu Ile Leu Ser Gly Phe Ile
305                 310                 315                 320

Asn Gly Leu Phe Leu Ile Val Ile Ala Phe Phe Val Phe Met Glu Ser
                325                 330                 335

Val Ala Arg Leu Ile Asp Pro Pro Glu Leu Asp Thr Asn Met Leu Thr
            340                 345                 350

Pro Val Ser Val Ala Gly Leu Ile Val Asn Leu Ile Gly Ile Cys Ala
        355                 360                 365

Phe Ser His Ala His Ser His Gly His Gly Ala Ser Gln Gly Asn Cys
    370                 375                 380

His Ser Asp His Gly His Ser His His Ala His Gly His Gly His Asp
```

```
385                 390                 395                 400
His Gly His Ser His Gly Phe Thr Gly Gly Gly Met Asn Ala Asn Met
            405                 410                 415

Arg Gly Val Phe Leu His Val Leu Ala Asp Thr Leu Gly Ser Ile Gly
            420                 425                 430

Val Ile Val Ser Thr Val Leu Ile Glu Gln Phe Gly Trp Phe Ile Ala
            435                 440                 445

Asp Pro Leu Cys Ser Leu Phe Ile Ala Val Leu Ile Phe Leu Ser Val
            450                 455                 460

Ile Pro Leu Ile Lys Asp Ala Cys Gln Val Leu Leu Arg Leu Pro
465             470                 475                 480

Pro Asp His Glu Lys Glu Leu His Ile Ala Leu Glu Lys Ile Gln Lys
            485                 490                 495

Ile Glu Gly Leu Ile Ser Tyr Arg Asp Pro His Phe Trp Arg His Ser
            500                 505                 510

Ala Ser Ile Val Ala Gly Thr Ile His Ile Gln Val Thr Ser Glu Val
            515                 520                 525

Leu Glu Gln Arg Ile Val Gln Gln Val Thr Gly Ile Leu Lys Asp Ala
            530                 535                 540

Gly Val Asn Asn Leu Thr Ile Gln Val Glu Lys Glu Ala Tyr Phe Gln
545                 550                 555                 560

His Met Ser Gly

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(29)

<400> SEQUENCE: 29
gggaattcat gggtaagacc ctgcggggc                                    29

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(35)

<400> SEQUENCE: 30
ggaagctttc actcatgtaa cccagattct ccagc                             35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(35)

<400> SEQUENCE: 31
ggttttctag agctcgtgca gacctggaga cgggc                             35
```

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(39)

<400> SEQUENCE: 32
gggttttcta gatcttcaga aatgagggcg acttttgtg                    39

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(29)

<400> SEQUENCE: 33
gggatccgca tagtacagca ggttacagg                               29

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(29)

<400> SEQUENCE: 34
ggtcgaccct ttaaaataca taactcaaa                               29

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(30)

<400> SEQUENCE: 35
aatgtatgca gtatggaaat ggaaagttgc                              30

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(28)

<400> SEQUENCE: 36
cgaatgggct gaccgcttcc tcgtgctt                                28

<210> SEQ ID NO 37
<211> LENGTH: 30
<212> TYPE: DNA

```
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(30)

<400> SEQUENCE: 37
cggcaggagc aaggtgagat gacaggagat                                      30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(30)

<400> SEQUENCE: 38
ttacagtgtc aggaataaag gctatgcttc                                      30

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(20)

<400> SEQUENCE: 39
gactcgatct catggcaaag                                                 20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(21)

<400> SEQUENCE: 40
tagagcatgt gagttagagc a                                               21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence
<221> NAME/KEY: primer_bind
<222> LOCATION: (1)..(21)

<400> SEQUENCE: 41
ccaacattct atcatctccc t                                               21

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence:an
      artificially synthesized primer sequence
```

```
<221> NAME/KEY: primer_bind
<222> LOCATION: (1)..(19)

<400> SEQUENCE: 42
agcggctcat cagggcagc                                                    19
```

PHYSIOLOGICALLY ACTIVE PROTEIN ORIGINATING IN MAMMALS

TECHNICAL FIELD

The present invention relates to a novel physiologically active protein originating in mammals, a DNA encoding said protein, and an antibody reactive with said protein.

BACKGROUND ART

A so-called geriatric disease, which is regarded as a current disease in high living standard society, includes arteriosclerosis as well as hypertension and diabetes. Important measures for preventing these diseases are not only development of therapeutic methods but also daily life control.

Arteriosclerosis begins with pathological changes (for example, (1) invasive growth of smooth muscle cells into inner membrane, (2) qualitative and quantitative changes of collagen, elastin, and acidic mucopolysaccharides, and (3) cell foaming by lipid accumulation in the cytoplasm of grown smooth muscle cells and macrophages implanting tissues) occurring in inner membrane of artery. As the result of such pathological changes, (1) foam cells found in the inner membrane produces fat spots on the surface of the inner membrane, (2) lipid accumulates between tissues (deep part of midmembrane) and the inner membrane surface is covered with thick glass-like membrane, accompanied by fibrous growth and calcification, and (3) bleeding and necrosis occur in tissues to cause combined pathological changes involving thrombogenesis, calcification, and deposition of lipid crystals. Such pathological changes, in time, distribute in artery of a whole body and narrow the cavity of the artery. In addition, the site of pathological changes becomes bursal and the vascular wall loses elasticity, thereby hardening blood vessels. The vessels then wind, and normal blood flow is inhibited.

Epidemiological studies so far have illustrated age (about thirties or more), hypercholesterolemia, hypo-HDL-cholesterolemia, systolic hypertension, obesity, hemoglobin high value, and diabetes as risk factors of the onset of arteriosclerosis. Dynamics of in vivo factors inducing the onset include secretion of adrenalin, increase of thromboxane A2, decrease of prostacyclin, increase of serum peroxylipid, increase of free fatty acid, increase of platelet, increase of fibrinogen, increase of blood coagulation factors (XII and XIII), decrease of tissue plasmin, increase of prostaglandin, decrease of antithrombin III, increase of serum LDL, decrease of serum HDL, increase of insulin, and increase of renin.

Studies so far have revealed only that multiple conditions, for example, physical conditions such as age and obesity, complication with other diseases, and abnormalities of the dynamics of many in vivo factors complicatedly are related to each other to cause arteriosclerosis.

Treatments of arteriosclerosis are divided with their purpose into (1) preventive treatments to retract arteriosclerosis and to prevent the onset of arteriosclerosis by correcting lifestyle and physical abnormalities such as obesity (for example, diet therapy and therapeutic exercise) and (2) chemotherapy or surgical therapy to remove vessel occlusion symptoms occurring with the progress of arteriosclerosis or to prevent the onset of vessel cavity occlusion symptoms by thrombus or embolus,.

Since particular decisive causes of arteriosclerosis are unclear, only symptomatic treatment by chemotherapy is currently possible. For example, β blocker is applied when the enhancement of a catecholamine derivative such as adrenalin is suspected as the cause, eicosapentaenoic acid is applied for a prostaglandin derivative, vitamin E is applied for peroxylipid, and urokinase is applied for thrombus. No effective pharmaceuticals for treating the arteriosclerosis have been provided yet.

In the surgical therapy for arterial occlusion, percutaneous transluminal coronary angioplasty (PTCA) based on the observation by angiography prevails clinically as an effective means to enlarge vessel cavity. PTCA has remarkably progressed and prevailed since it was clinically applied by Gruntzig for the first time in 1977, and the number of the operation has rapidly increased in Japan.

PTCA is the method in which the occlusion (constriction) site is enlarged by inserting a thin catheter with a balloon at the tip in a thick catheter into the coronary artery occlusion site and by expanding the balloon.

However, in cavity enlargement by PTCA, restenosis occurs at the operation site of the artery in about 30 to 50% of the cases within a few months after the operation, and this restenosis is a major drawback of PTCA.

The restenosis has been thought to occur by the amplification of neonatal inner membrane proliferation based on the repair reaction of the injury site of the vascular wall, which has been inevitably caused by the enlargement of the occlusion site by PTCA. Although chemotherapy has been tried for preventing this restenosis, almost no effective drugs have been reported so far.

As mentioned above, at present, a method for the complete treatment and prevention of arteriosclerosis comprising the prevention of the recurrence of arteriosclerosis and the occurrence of restenosis has not established. It is thus desired to clarify the cause of the onset and progress of arteriosclerosis and to develop a method for the effective treatment and prevention thereof, and therapeutic and preventive drugs.

Coronary artery restenosis occurring after PTCA is regarded as a clinical model of arteriosclerosis from pathological viewpoints such as neonatal inner membrane proliferation or intimal thickening. Therefore, to diagnose the tissue characteristics of the vascular wall at the restenosis site after PTCA and to elucidate the difference between the characteristics and those of normal vascular wall by comparing them pathologically and at the gene level are effective to identify the cause and factors of restenosis, and further, arteriosclerosis.

In such comparative studies, a useful method for comparison and examination at the gene level using the genetic engineering technique is called differential display method (Nucleic Acids Research, Vol.21, No.18, pp.4272–4280 (1993); and Science, Vol.257, pp.967–971 (1992)).

Specifically, PCTA is applied to the coronary artery of a large mammal such as a rabbit, the expression patterns of genes in the inner membrane tissue at the PTCA site are examined by differential display method, and they are compared with the gene expression patterns in the inner membrane tissue without PCTA, to thereby identify genes specifically or increasingly expressed after PTCA.

DISCLOSURE OF THE INVENTION

Genes that express specifically or increasingly after PTCA and proteins derived from said genes may be closely related to arteriosclerosis and restenosis. The present invention provides pharmaceuticals and methods for preventing and treating arteriosclerosis and restenosis by identifying genes and proteins expressing specifically in arteriosclerosis and coronary artery restenosis.

As the result of studies on the analyses of genes specific to arteriosclerosis and/or coronary artery restenosis, the present inventors have discovered genes encoding two novel proteins (clone BA0306 and BA2303) that express increasingly at the comparatively early stage (day 1 to 7) after PTCA and completed the present invention.

The two novel protein-encoding genes of the present invention, whose characteristics are mentioned below, are expressed specifically after PTCA, and are thought to be genes involved in onset and progress of arteriosclerosis and/or coronary artery restenosis.

Clone BA0306 has the following characteristics.

(1) Its increased expression is observed on day 1 to 7 after PTCA of coronary artery (the peak is observed on day 4).

(2) Northern blotting reveals the expression of the mRNA as about 3.5 k and about 4.4 k bands in various human tissues.

(3) It has ten putative transmembrane regions.

(4) It has amino acid sequence homology with *S. cerevisiae* oxidative stress resistance protein, *S. cerevisiae* zinc/cadmium resistance protein, heavy metal ion resistance protein, and so on.

(5) The molecules derived from humans and rabbits have the amino acid sequences of SEQ ID NO: 10 and 8, respectively. The molecule derived from mice has the amino acid sequence of SEQ ID NO: 28.

Judging from these characteristics, clone BA0306 is thought to inhibit active oxygen such as nitrogen monoxide (NO), which is involved in the progress of arteriosclerosis and/or restenosis.

Clone BA2303 has the following characteristics.

(1) Its increased expression is observed from day 1 after PTCA of coronary artery, and the expression continues until day 7 with the maximum expression on day 2 to 4.

(2) Northern blotting reveals the expression of the mRNA as about 3.9 k and about 2.1 k bands in various human tissues.

(3) It has seven putative transmembrane regions.

(4) The molecules derived from humans and mice have the amino acid sequences of SEQ ID NO: 4 and 6, respectively. The molecule derived from rabbits has the amino acid sequence of SEQ ID NO: 2.

Judging from these characteristics, clone BA2303 is thought to be a GTP binding protein (G protein)-coupled receptor that transmits a specific signal through intracellular G protein to an effector on the plasma membrane or the surface of the cytoplasm by binding to an in vivo ligand involved in the onset or progress of arteriosclerosis and/or restenosis.

Therefore, the genes (DNAs), proteins, or their fragments of the present invention and antibodies or a portion of them reactive with the proteins of the present invention are extremely useful for developing drugs for treatment and prevention of arteriosclerosis and for treatment and prevention of restenosis after PTCA for artery occlusion symptom and so on, targeting said genes or protein molecules. In addition, the DNAs of the present invention themselves are useful as antisense pharmaceuticals, extracellular region fragments of said proteins, for example, as soluble receptor pharmaceuticals, and said antibodies and a portion of them as antibody pharmaceuticals.

Genes (DNAs), proteins, and antibodies of the present invention are useful as reagents for searching proteins (ligands) interacting with the proteins of the present invention, thereby elucidating the function of said ligands, and developing therapeutic drugs targeting said ligands.

Based on the genetic information of the rabbit- or mouse-derived DNA, one embodiment of DNAs of the present invention, model animals (knockout animals) can be produced by disrupting (inactivating) the endogenous gene corresponding to the DNA. Similarly, transgenic animals can be produced as model animals by introducing the human-derived DNA, one embodiment of DNAs of the present invention, into nonhuman mammals such as mice. Function of genes and proteins of the present invention can be elucidated by analyzing the physical, biological, pathologic, and genetic characteristics of these model animals.

Moreover, by mating the model animals whose endogenous gene is thus disrupted with the transgenic animals, model animals that have only the human-derived gene of the present invention can be produced. By administering drugs (compounds, antibodies, and so on) targeting the introduced human gene to these model animals, the therapeutic effect of the drug can be estimated.

Namely, the present invention provides the DNAs, proteins, expression vectors, transformants, antibodies, pharmaceutical compositions, transgenic mice, and knockout, mentioned below.

(1) A DNA encoding a protein having the amino acid sequence of SEQ ID NO: 4.

(2) A DNA encoding a protein fragment comprising the extracellular region of a protein having the amino acid sequence of SEQ ID NO: 4.

(3) A DNA comprising a nucleotide sequence corresponding to nucleotide residues 97 to 1419 of the nucleotide sequence of SEQ ID NO: 3.

(4) A DNA hybridizing with a DNA having the nucleotide sequence of SEQ ID NO: 3 under stringent conditions.

(5) A protein having the amino acid sequence of SEQ ID NO: 4 or an amino acid sequence substantially the same as said amino acid sequence.

(6) A protein fragment comprising the extracellular region of a protein having the amino acid sequence of SEQ ID NO: 4 or an amino acid sequence substantially the same as said amino acid sequence.

(7) A fusion protein between the extracellular region of the protein of (5) and the constant region of the heavy chain of human immunoglobulin (Ig) or a portion of the constant region.

(8) An expression vector comprising the DNA of any one of (1) to (4).

(9) A transformant carrying the expression vector of (8).

(10) An antibody or its portion reactive with the protein of (5) or the protein fragment of (6).

(11) The antibody or its portion of (10), wherein the antibody is a monoclonal antibody.

(12) A pharmaceutical composition comprising the protein fragment of (6) or the fusion protein of (7) and a pharmaceutically acceptable carrier.

(13) A pharmaceutical composition comprising the antibody or its portion of (10) or (11) and a pharmaceutically acceptable carrier.

(14) A DNA encoding a protein having the amino acid sequence of SEQ ID NO: 10.

(15) A DNA encoding a protein fragment comprising the extracellular region of a protein having the amino acid sequence of SEQ ID NO: 10.

(16) A DNA having a nucleotide sequence corresponding to nucleotide residues 1 to 1785 of the nucleotide sequence of SEQ ID NO: 9.

(17) A DNA hybridizing with a DNA having the nucleotide sequence of SEQ ID NO: 9 under stringent conditions.

(18) A protein having the amino acid sequence of SEQ ID NO: 10 or an amino acid sequence substantially the same as said amino acid sequence.

(19) A protein fragment comprising the extracellular region of a protein having the amino acid sequence of SEQ ID NO: 10 or an amino acid sequence substantially the same as said amino acid sequence.

(20) A fusion protein comprising the extracellular region of the protein of (18) and the constant region of the heavy chain of human immunoglobulin (Ig) or a portion of the constant region.

(21) An expression vector comprising the DNA of any one of (14) to (17).

(22) A transformant carrying the expression vector of (21).

(23) An antibody or its portion reactive with the protein of (18) or the protein fragment of (19).

(24) The antibody or its portion of (23), wherein the antibody is a monoclonal antibody.

(25) A pharmaceutical composition comprising the protein fragment of (19) or the fusion protein of (20) and a pharmaceutically acceptable carrier.

(26) A pharmaceutical composition comprising the antibody or its portion of (23) or (24) and a pharmaceutically acceptable carrier.

(27) A transgenic mouse in which the human-derived DNA comprising a DNA having a nucleotide sequence corresponding to nucleotide residues 97 to 1419 of the nucleotide sequence of SEQ ID NO: 3 is integrated into an endogenous gene of said mouse.

(28) A transgenic mouse in which the human-derived DNA comprising a DNA having a nucleotide sequence corresponding to nucleotide residues 1 to 1785 of the nucleotide sequence of SEQ ID NO: 9 is integrated into an endogenous gene of said mouse.

(29) A knockout mouse whose endogenous gene encoding a mouse-derived protein having the amino acid sequence of SEQ ID NO: 6 is inactivated so that said protein is not produced.

(30) A knockout mouse whose endogenous gene encoding a mouse-derived protein comprising the amino acid sequence of SEQ ID NO: 28 is inactivated so that said protein is not produced.

In the following, the present invention is explained in detail by clarifying the meanings of terms used in the present application and the general production methods of proteins, protein fragments, fusion proteins, DNAS, antibodies, transgenic mice, and knockout mice of the present invention.

A "protein" of the present invention means a protein and its fragment derived from mammals such as humans, rabbits, and mice, and preferably, a human-derived protein and its fragment. Particularly preferable examples are (1) a protein having the amino acid sequence of SEQ ID NO: 4 or an amino acid sequence substantially the same as said amino acid sequence, (2) a protein fragment comprising the extracellular region of a protein having the amino acid sequence of SEQ ID NO: 4 or an amino acid sequence substantially the same as said amino acid sequence, (3) a protein having the amino acid sequence of SEQ ID NO: 10 or an amino acid sequence substantially the same as said amino acid sequence, and (4) a protein fragment comprising the extracellular region of a protein having the amino acid sequence of SEQ ID NO: 10 or an amino acid sequence substantially the same as said amino acid sequence.

The term "extracellular region" used herein is explained below. A transmembrane protein such as a G protein-coupled receptors or cell surface molecule connects with the membrane through the hydrophobic peptide region penetrating the lipid bilayer of the membrane once or several times and has structure composed of three main regions, that is, extracellular region, transmembrane region, and cytoplasmic region. Such a transmembrane protein exists as a-monomer, homodimer, heterodimer, or oligomer with another chain(s) having the same or different amino acid sequence.

The term "extracellular region" used herein means the partial structure (partial sequence) existing outside of the membrane that holds the transmembrane protein as mentioned above among the whole structure of said membrane protein. In other words, it corresponds to the region excluding the region incorporated into the membrane (transmembrane region) and the region existing in the cytoplasm following the transmembrane region (cytoplasmic region). If desired, one to five amino acids derived from the amino acids constituting the transmembrane and/or cytoplasmic region can be added to the N- terminus and/or C-terminus of the extracellular region in the present invention.

Here, "having substantially the same amino acid sequence" means to include a protein having an amino acid sequence where multiple amino acids, preferably 1 to 10 amino acids, particularly preferably 1 to 5 amino acids, in the amino acid sequence shown in SEQ ID NO: 4 or 10, are substituted, deleted, and/or modified, and a protein having an amino acid sequence where multiple amino acids, preferably 1 to 10 amino acids, particularly preferably 1 to 5 amino acids, are added to said amino acid sequence, as far as the protein has substantially the same biological properties as the protein having said amino acid sequence.

Alphabetical triplet or single letter codes used to represent amino acids in the present specification or figures mean amino acids as follows. (Gly/G) glycine, (Ala/A) alanine, (Val/V) valine, (Leu/L) leucine, (Ile/I) isoleucine, (Ser/S) serine, (Thr/T) threonine, (Asp/D) aspartic acid, (Glu/E) glutamic acid, (Asn/N) asparagine, (Gln/Q) glutamine, (Lys/K) lysine, (Arg/R) arginine, (Cys/C) cysteine, (Met/M) methionine, (Phe/F) phenylalanine, (Tyr/Y) tyrosine, (Trp/W) tryptophane, (His/H) histidine, (Pro/P) proline.

"The constant region or a portion of the constant region of human immunoglobulin (Ig) heavy chain" used herein means the constant region or the Fc region of human-derived immunoglobulin heavy chain (H chain) as described, or a portion of them. The immunoglobulin can be any immunoglobulin belonging to any class and any subclass. Specifically, examples of the immunoglobulin are IgG (IgG1, IgG2, IgG3, and IgG4), IgM, IgA (IgA1 and IgA2), IgD, and IgE. Preferably, the immunoglobulin is IgG (IgG1, IgG2, IgG3, or IgG4), or IgM. Examples of particularly preferable immunoglobulin of the present invention are those belonging to human-derived IgG (IgG1, IgG2, IgG3, or IgG4).

Immunoglobulin has a Y-shaped structural unit in which four chains composed of two homologous light chains (L chains) and two homologous heavy chains (H chains) are connected through disulfide bonds (S—S bonds). The light chain is composed of the light chain variable region (VL)

and the light chain constant region (CL). The heavy chain is composed of the heavy chain variable region (VH) and the heavy chain constant region (CH).

The heavy chain constant region is composed of some domains having the amino acid sequences inherent in each class (IgG, IgM, IgA, IgD, and IgE) and each subclass (IgG1, IgG2, IgG3, and IgG4, IgA1, and IgA2).

The heavy chain of IgG (IgG1, IgG2, IgG3, and IgG4) is composed of VH, CH1 domain, hinge region, CH2 domain, and CH3 domain in this order from N terminus.

Similarly, the heavy chain of IgG1 is composed of VH, $C\gamma_1 1$ domain, hinge region, $C\gamma_1 2$ domain, and $C\gamma_1 3$ domain in this order from N terminus. The heavy chain of IgG2 is composed of VH, $C\gamma_2 1$ domain, hinge region, $C\gamma_2 2$ domain, and $C\gamma_2 3$ domain in this order from N terminus. The heavy chain of IgG3 is composed of VH, $C\gamma_3 1$ domain, hinge region, $C\gamma_3 2$ domain, and $C\gamma_3 3$ domain in this order from N terminus. The heavy chain of IgG4 is composed of VH, $C\gamma_4 1$ domain, hinge region, $C\gamma_4 2$ domain, and $C\gamma_4 3$ domain in this order from N terminus.

The heavy chain of IgA is composed of VH, $C\alpha 1$ domain, hinge region, $C\alpha 2$ domain, and $C\alpha 3$ domain in this order from N terminus.

Similarly, the heavy chain of IgA1 is composed of VH, $C\alpha_1 1$ domain, hinge region, $C\alpha_1 2$ domain, and $C\alpha_1 3$ domain in this order from N terminus. The heavy chain of IgA2 is composed of VH, $C\alpha_2 1$ domain, hinge region, $C\alpha_2 2$ domain, and $C\alpha_2 3$ domain in this order from N terminus.

The heavy chain of IgD is composed of VH, $C\delta 1$ domain, hinge region, $C\delta 2$ domain, and $C\delta 3$ domain in this order from N terminus.

The heavy chain of IgM is composed of VH, $C\mu 1$ domain, $C\mu 2$ domain, $C\mu 3$ domain, and $C\mu 4$ domain in this order from N terminus and have no hinge region as seen in IgG, IgA, and IgD.

The heavy chain of IgE is composed of VH, $C\epsilon 1$ domain, $C\epsilon 2$ domain, $C\epsilon 3$ domain, and $C\epsilon 4$ domain in this order from N terminus and have no hinge region as seen in IgG, IgA, and IgD.

If, for example, IgG is treated with papain, it is cleaved at the slightly N terminal side beyond the disulfide bonds existing in the hinge region where the disulfide bonds connect the two heavy chains to generate two homologous Fab, in which a heavy chain fragment composed of VH and CH1 is connected with one light chain through a disulfide bond, and one Fc, in which two homologous heavy chain fragments composed of the hinge region, CH2 domain, and CH3 domain are connected through disulfide bonds (See "Immunology Illustrated", original 2nd ed., Nankodo, pp.65–75 (1992); and "Focus of Newest Medical Science 'Recognition Mechanism of Immune System'", Nankodo, pp.4–7 (1991); and so on).

Namely, "a portion of a constant region of immunoglobulin heavy chain" of the present invention means a portion of a constant region of an immunoglobulin heavy chain having the structural characteristics as mentioned above, and preferably, is the constant region without C1 domain, or the Fc region. Specifically, examples thereof are the region composed of hinge region, C2 domain, and C3 domain from each of IgG, IgA, and IgD, and are the region composed of C2 domain, C3 domain, and C4 domain from each of IgM and IgE. A particularly preferable example thereof is the Fc region of human-derived IgG1.

The "fusion protein" of the present invention is that composed of the above-described extracellular region of the protein of the present invention and a constant region or a portion of a constant region of human immunoglobulin (Ig) heavy chain. Preferably, it is a fusion polypeptide composed of an extracellular region of a protein of the present invention and a portion of a constant region of human IgG heavy chain, and particularly preferably, it is a fusion polypeptide composed of an extracellular region of a protein of the present invention and the region (Fc) composed of a hinge region, CH2 domain, and CH3 domain of human IgG heavy chain. Moreover, IgG1 is preferable among IgG. In addition, a protein derived from human, mouse, or rat (preferably, human) is preferable as the protein of the present invention.

The fusion protein of the present invention has the advantage that the fusion polypeptide can be purified extremely easily by using affinity column chromatography using the property of protein A, which binds specifically to the immunoglobulin fragment because the fusion polypeptide of the present invention has a portion of a constant region (for example Fc) of an immunoglobulin such as IgG as mentioned above as a fusion partner. Moreover, since various antibodies against the Fc of various immunoglobulin are available, an immunoassay for the fusion polypeptides can be easily performed with antibodies against the Fc.

The protein, protein fragment, and fusion protein of the present invention can be produced not only by recombinant DNA technology as mentioned below but also by a method well known in the art such as a chemical synthetic method and a cell culture method, or a modified method thereof.

The DNA of the present invention encodes the above-mentioned protein of the present invention, and includes any nucleotide sequence that can encode the protein of the present invention. The DNA preferably encodes a human-derived protein of the present invention. Specific examples of the DNA are described below.

(1) A DNA encoding a protein having the amino acid sequence of SEQ ID NO: 4, a protein fragment composed of the extracellular region of said protein, or a biological analog obtained by substituting, deleting, and/or modifying multiple amino acids, preferably 1 to 10 amino acids, particularly preferably 1 to 5 amino acids in the amino acid sequence of said protein or fragment, or by inserting multiple amino acids, preferably 1 to 10 amino acids, particularly preferably 1 to 5 amino acids, in said amino acid sequence.

(2) A DNA encoding a protein having the amino acid sequence of SEQ ID NO: 10, a protein fragment composed of the extracellular region of said protein, or a biological analog obtained by substituting, deleting, and/or modifying multiple amino acids, preferably 1 to 10 amino acids, particularly preferably 1 to 5 amino acids, in the amino acid sequence of said protein or fragment, or by inserting multiple amino acids, preferably 1 to 10 amino acids, particularly preferably 1 to 5 amino acids, in said amino acid sequence.

(3) A DNA hybridizing with a DNA having the nucleotide sequence of SEQ ID NO: 3 under stringent conditions.

(4) A DNA hybridizing with a DNA having the nucleotide sequence of SEQ ID NO: 9 under stringent conditions.

Specific examples thereof are (1) a DNA having a nucleotide sequence corresponding to nucleotide residues 97 to 1419 of the nucleotide sequence of SEQ ID NO: 3, (2) a DNA comprising a nucleotide sequence corresponding to nucleotide residues 1 to 1419 of the nucleotide sequence of SEQ ID NO: 3, (3) a DNA having a nucleotide sequence corresponding to nucleotide residues 1 to 1785 of the nucleotide sequence of SEQ ID NO: 9, and (4) a DNA comprising a nucleotide sequence corresponding to nucleotide residues 1 to 1785 of the nucleotide sequence of SEQ ID NO: 9.

The DNA of the present invention comprises either a genomic DNA or cDNA. In addition, the DNA includes any DNA composed of any codons encoding the same amino acids.

Examples of "stringent conditions" are as follows. When a probe with 50 or more nucleotides is used and hybridization is performed in 0.9% NaCl, the standard of temperature where 50% dissociation occurs (Tm) is calculated using the following formula and the temperature for hybridization can be determined according to the following formula.

$$Tm = 82.3° C. + 0.41 \times (G+C)\% - 500/n - 0.61 \times (\text{formamide})\%$$

(n means the number of the nucleotide of probe).
Temperature=Tm −25° C.

In addition, when a probe with 100 or more nucleotides (G+C=40 to 50%) is used, it should be considered that Tm varies as (1) and (2) mentioned below.

(1) Tm descends by about 1° C. per 1% mismatch.
(2) Tm descends by 0.6 to 0.7° C. per 1% formamide.

Accordingly, the temperature conditions for the combination of completely complementary strands can be set as follows.

(A) 65 to 75° C. (formamide not added)
(B) 35 to 45° C. (in the presence of 50% formamide)

The temperature conditions for the combination of incompletely complementary strands can be set as follows.

(A) 45 to 55° C. (formamide not added)
(B) 35 to 42° C. (in the presence of 30% formamide)

The temperature conditions when a probe with 23 or less nucleotides is used can be 37cC or can be calculated using the following formula.

$$\text{Temperature} = 2° C. \times (\text{the number of } A+T) + 4° C. \times (\text{the number of } C+G) - 5° C.$$

The DNA of the present invention can be a DNA obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

The DNA encoding the protein of the present invention can be obtained by the usual method such as a method to clone cDNA from mRNA encoding the protein of the present invention, a method to isolate genomic DNA and then splice them, chemical synthesis and so on.

(1) cDNA can be cloned from the mRNA encoding the protein of the present invention by, for example, the method described below.

First, the mRNA encoding the protein of the present invention is prepared from the above-described tissues or cells expressing and producing a cell surface molecule (polypeptide) of the present invention. mRNA can be prepared isolating total RNA by a known method such as quanidine-thiocyanate method (Chirgwin et al., Biochemistry, Vol.18, p5294, 1979), hot phenol method, or AGPC method, and subjecting it to affinity chromatography using oligo-dT cellulose or poly-U Sepharose.

Then, with the mRNA obtained as a template, cDNA is synthesized, for example, by a well-known method using reverse transcriptase such as the method of Okayama et al. (Mol. Cell. Biol. Vol.2, p.161 (1982); ibid. Vol.3, p.280 (1983)) or the method of Hoffman et al. (Gene Vol.25, p.263 (1983)), and converted into double-stranded cDNA. A cDNA library is prepared by transforming E. coli with plasmid vectors, phage vectors, or cosmid vectors having this cDNA or by transfecting E. coli after in vitro packaging.

The plasmid vectors used in this invention are not limited as long as they are replicated and maintained in hosts. Any phage vectors that can be replicated in hosts can also be used. Examples of usually used cloning vectors are pUC19, λgt10, λgt11, and so on. When the vector is applied to immunological screening as mentioned below, the vector having a promoter that can express a gene encoding the polypeptide of the present invention in a host is preferably used.

cDNA can be inserted into a plasmid by, for example, the method of Maniatis et al. (Molecular Cloning, A Laboratory Manual, second edition, Cold Spring Harbor Laboratory, p.1.53, 1989). cDNA can be inserted into a phage vector by, for example, the method of Hyunh et al. (DNA cloning, a practical approach, Vol.1, p.49 (1985)). These methods can be simply performed by using a commercially available cloning kit (for example, a product from Takara Shuzo). The recombinant plasmid or phage vector thus obtained is introduced into appropriate host cells such as a prokaryote (for example, E. coli: HB101, DH5α, MC1061/P3, etc.).

Examples of a method for introducing a plasmid into a host are calcium chloride method, calcium chloride/rubidium chloride method described in Molecular Cloning, A Laboratory Manual (second edition, Cold Spring Harbor Laboratory, p.1.74 (1989)), and electroporation method. Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

The cDNA encoding the protein of the present invention can be isolated from the cDNA library so prepared according to the method mentioned above by combining general cDNA screening methods.

For example, a clone comprising the desired cDNA can be screened by a known colony hybridization method (Crunstein et al. Proc. Natl. Acad. Sci. USA, Vol.72, p.3961 (1975)) or plaque hybridization method (Molecular Cloning, A Laboratory Manual, second edition, Cold Spring Harbor Laboratory, p.2.108 (1989)) using $^{32}$P-labeled chemically synthesized oligonucleotides as probes, which are corresponding to the amino acid sequence of the polypeptide of the present invention. Alternatively, a clone having a DNA fragment encoding a specific region within the polypeptide of the present invention can be screened by amplifying the region by PCR with synthetic PCR primers.

When a cDNA library prepared using a cDNA expression vector (for example, λZAPII phage vector) is used, the desired clone can be screened by the antigen-antibody reaction using an antibody against the polypeptide of the present invention. A screening method using PCR method is preferably used when many clones are subjected to screening.

The nucleotide sequence of the DNA thus obtained can be determined by Maxam-Gilbert method (Maxam et al. Proc. Natl. Acad. Sci. USA, Vol.74, p.560 (1977)) or the dideoxynucleotide synthetic chain termination method using phage M13 (Sanger et al. Proc. Natl. Acad. Sci. USA, Vol.74, pp.5463–5467 (1977)). The whole or a portion of the gene encoding the polypeptide of the present invention can be obtained by excising the clone obtained as mentioned above with restriction enzymes and so on.

(2) The DNA encoding the polypeptide of the present invention can be isolated from the genomic DNA derived from the cells expressing the polypeptide of the present invention as mentioned above by the following methods. Such cells are solubilized preferably by SDS or proteinase K, and the DNAs are deproteinized by repeating phenol extraction. RNAs are digested preferably with ribonuclease. The DNAs obtained are partially digested with appropriate restriction enzymes, and the DNA fragments obtained are amplified with appropriate phage or cosmid to generate a library. Then, clones having the desired sequence are detected, for example, by using radioactively labeled DNA probes, and the whole or a portion of the gene encoding the protein of the present invention is obtained from the clones by excision with restriction enzyme and so on.

(3) The DNA of the present invention can also be chemically synthesized by the usual method, based on the nucleotide sequence of SEQ ID NO: 1, 3, 5, 7, 9, or 27.

The present invention also relates to a recombinant vector comprising the DNA encoding the protein of the present invention. The recombinant vector of the present invention is not limited as long as it can be replicated and maintained or can autonomously replicate in various prokaryotic and/or eukaryotic hosts. The vector of the present invention includes plasmid vectors and phage vectors.

The recombinant vector can easily be prepared by ligating the DNA encoding the protein of the present invention with a vector for recombination available in the art (plasmid DNA and bacteriophage DNA) by the usual method. Specific examples of the vectors for recombination used are E. coli-derived plasmids such as pBR322, pBR325, pUC12, pUC13, and pUC19, yeast-derived plasmids such as pSH19 and pSH15, and Bacillus subtilis-derived plasmids such as pUB110, pTP5, and pC194. Examples of phages are a bacteriophage such as λ phage, and an animal or insect virus (pVL1393, Invitrogen) such as a retrovirus, vaccinia virus, and nuclear polyhedrosis virus.

An expression vector is useful for expressing the DNA encoding the protein of the present invention and for producing the polypeptide of the present invention. The expression vector is not limited as long as it expresses the gene encoding the polypeptide of the present invention in various prokaryotic and/or eukaryotic host cells and produces this protein. Examples thereof are pMAL C2, pEF-BOS (Nucleic Acids Res. Vol.18, p.5322 (1990)), pME18S (Experimental Medicine: SUPPLEMENT, "Handbook of Genetic Engineering" (1992)), and so on.

When bacteria, particularly E. coli are used as host cells, an expression vector is generally comprised of, at least, a promoter/operator region, an initiation codon, the DNA encoding the protein of the present invention, termination codon, terminator region, and replicon.

When yeast, animal cells, or insect cells are used as hosts, an expression vector is preferably comprised of, at least, a promoter, an initiation codon, the DNA encoding the protein of the present invention, and a termination codon. It may also comprise the DNA encoding a signal peptide, enhancer sequence, 5'- and 3'-untranslated region of the gene encoding the protein of the present invention, splicing junctions, polyadenylation site, selectable marker region, and replicon. The expression vector may also contain, if required, a gene for gene amplification (marker) that is usually used.

A promoter/operator region to express the polypeptide of the present invention in bacteria comprises a promoter, an operator, and a Shine-Dalgarno (SD) sequence (for example, AAGG). For example, when the host is Escherichia, it preferably comprises Trp promoter, lac promoter, recA promoter, λPL promoter, lpp promoter, tac promoter, or the like. Examples of a promoter to express the polypeptide of the present invention in yeast are PH05 promoter, PGK promoter, GAP promoter, ADH promoter, and so on. When the host is Bacillus, examples thereof are SL01 promoter, SP02 promoter, penP promoter and so on. When the host is a eukaryotic cell such as a mammalian cell, examples thereof are SV40-derived promoter, retrovirus promoter, heat shock promoter, and so on, and preferably SV-40 and retrovirus-derived one. As a matter of course, the promoter is not limited to the above examples. In addition, to use an enhancer is effective for expression.

A preferable initiation codon is, for example, a methionine codon (ATG).

The commonly used termination codon (for example, TAG, TGA, TAA, and so on) is illustrated as a termination codon.

Usually used natural or synthetic terminators are used as a terminator region.

A replicon means a DNA capable of replicating the whole DNA sequence in host cells, and includes a natural plasmid, an artificially modified plasmid (DNA fragment prepared from a natural plasmid), a synthetic plasmid, and so on. Examples of a preferable plasmids are pBR322 or its artificial derivatives (DNA fragment obtained by treating pBR322 with appropriate restriction enzymes) for E. coli, yeast 2μ plasmid or yeast chromosomal DNA for yeast, and pRSVneo ATCC 37198, pSV2dhfr ATCC 37145, pdBPV-MMTneo ATCC 37224, pSV2neo ATCC 37149, etc. for mammalian cells.

An enhancer sequence, polyadenylation site, and splicing junction that are usually used in the art, such as those derived from SV40 can be also used.

A selectable marker usually used can be used according to the usual method. Examples thereof are resistance genes for antibiotics, such as tetracycline, neomycin, ampicillin, or kanamycin, and thymidine kinase gene.

Examples of a gene for gene amplification are dihydrofolate reductase (DHFR) gene, thymidine kinase gene, neomycin resistance gene, glutamate synthase gene, adenosine deaminase gene, ornithine decarboxylase gene, hygromycin-B-phophotransferase gene, aspartate transcarbamylase gene, etc.

The expression vector of the present invention can be prepared by continuously and circularly linking at least the above-mentioned promoter, initiation codon, DNA (gene) encoding the polypeptide of the present invention, termination codon, and terminator region, to an appropriate replicon. If desired, appropriate DNA fragments (for example, linkers, restriction sites generated with other restriction enzyme), can be used by the usual method such as digestion with a restriction enzyme or ligation using T4 DNA ligase.

Transformants of the present invention can be prepared by introducing the expression vector mentioned above into host cells.

Host cells used in the present invention are not limited as long as they are compatible with an expression vector mentioned above and can be transformed. Examples thereof are various cells such as natural cells or artificially established recombinant cells usually used in technical field of the present invention (for example, bacteria (Escherichia and Bacillus), yeast (Saccharomyces, Pichia, etc.), animal cells, or insect cells.

E. coli or animal cells are preferably used. Specific examples are E. coli (DH5α, TB1, HB101, etc.), mouse-derived cells (COP, L, C127, Sp2/0, NS-1, NIH 3T3, etc.), rat-derived cells, hamster-derived cells (BHK, CHO, etc.), monkey-derived cells (COS1, COS3, COS7, CV1, Velo, etc.), and human-derived cells (Hela, diploid fibroblast-derived cells, HEK293, myeloma, Namalwa, etc.).

An expression vector can be introduced (transformed (transduced)) into host cells by known method.

Transformation can be performed, for example, according to the method of Cohen et al. (Proc. Natl. Acad. Sci. USA, Vol.69, p.2110 (1972)), protoplast method (Mol. Gen. Genet., Vol.168, p.111 (1979)), or competent method (J. Mol. Biol., Vol.56, p.209 (1971)) when the hosts are bacteria (*E. coli, Bacillus subtilis*, etc.), the method of Hinnen et al. (Proc. Natl. Acad. Sci. USA, Vol.75, p.1927 (1978)), or lithium method (J. Bacteriol., Vol.153, p.163 (1983)) when the host is *Saccharomyces cerevisiae*, the method of Graham (Virology, Vol.52, p.456 (1973)) when the hosts are animal cells, and the method of Summers et al. (Mol. Cell. Biol., Vol.3, pp.2156–2165 (1983)) when the hosts are insect cells.

The protein of the present invention can be produced by cultivating transformants (in the following this term includes transductants) comprising an expression vector prepared as mentioned above in nutrient media.

The nutrient media preferably comprise carbon source, inorganic nitrogen source, or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meet extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, etc.).

Cultivation is performed by a method known in the art. Cultivation conditions such as temperature, pH of the media, and cultivation time are selected appropriately so that the protein of the present invention is overproduced.

Specific media and cultivation conditions used depending on host cells are illustrated below, but are not limited thereto.

When the hosts are bacteria, actinomycetes, yeasts, filamentous fungi, liquid media comprising the nutrient source mentioned above are appropriate. The media with pH 5 to 8 are preferably used.

When the host is *E. coli*, examples of preferable media are LB media, and M9 media (Miller et al. Exp. Mol. Genet., Cold Spring Harbor Laboratory, p.431 (1972)). Using these media, cultivation can be performed usually at 14 to 43° C. for about 3 to 24 hours with aeration and stirring, if necessary.

When the host is Bacillus, cultivation can be performed usually at 30 to 40° C. for about 16 to 96 hours with aeration and stirring, if necessary.

When the host is yeast, examples of media are Burkholder minimal media (Bostian, Proc. Natl. Acad. Sci. USA, Vol.77, p.4505 (1980)). The pH of the media is preferably 5 to 8. Cultivation can be performed usually at 20 to 35° C. for about 14 to 144 hours with aeration and stirring, if necessary.

When the host is an animal cell, examples of media are MEM media containing about 5 to 20% fetal bovine serum (Science, Vol.122, p.501 (1952)), DMEM media (Virology, Vol.8, p.396 (1959)), RPMI1640 media (J. Am. Med. Assoc., Vol.199, p.519 (1967)), and 199 media (Proc. Soc. Exp. Biol. Med., Vol.73, p.1 (1950)). The pH of the media is preferably about 6 to 8. Cultivation can be performed usually at about 30 to 40° C. for about 15 to 72 hours with aeration and stirring, if necessary.

When the host is an insect cell, an example of media is Grace's media containing fetal bovine serum (Proc. Natl. Acad. Sci. USA, Vol.82, p.8404 (1985)). The pH thereof is preferably about 5to 8. Cultivation can be performed usually at about 20 to 40° C. for 15 to 100 hours with aeration and stirring, if necessary.

The protein of the present invention can be produced as a transmembrane protein by cultivating transformants as mentioned above, in particular animal cells to overexpress the protein of the present invention on the surface of the cells. The protein of the present invention can be produced as a soluble protein fragment such as an extracellular region protein fragment by preparing the transformants as mentioned above using the DNA encoding the extracellular region and by cultivating the transformants to allow them to secrete the soluble polypeptide into the culture supernatant.

Namely, a culture filtrate (supernatant) is obtained by the method such as filtration or centrifugation of the obtained culture, and the protein of the present invention is purified and isolated from the culture filtrate by the usual method commonly used in order to purify and isolate a natural or synthetic protein.

Examples of the isolation and purification method are a method utilizing solubility, such as salting out and solvent precipitation method, a method utilizing the difference in molecular weight, such as dialysis, ultrafiltration, gel filtration, and sodium dodecyl sulfate-polyacrylamide gel electrophoresis, a method utilizing charges, such as ion exchange chromatography and hydroxylapatite chromatography, a method utilizing specific affinity, such as affinity chromatography, a method utilizing the difference in hydrophobicity, such as reverse phase high performance liquid chromatography, and a method utilizing the difference in isoelectric point, such as isoelectric focusing.

When the protein of the present invention exists in the periplasm or cytoplasm of cultured transformants, first, the fungus bodies or cells are harvested by the usual method such as filtration or centrifugation and suspended in appropriate buffer. After the cell wall and/or cell membrane of the cells and so on are disrupted by the method such as lysis with sonication, lysozyme, and freeze-thawing, the membrane fraction comprising the protein of the present invention is obtained by the method such as centrifugation or filtration. The membrane fraction is solubilized with a detergent such as Triton-X100 to obtain the crude extract. Finally, the polypeptide or the polypeptide fragment is isolated and purified from the crude extract by the usual method as illustrated above.

The "transgenic mouse" of the present invention is a transgenic mouse wherein the DNA (cDNA or genomic DNA) prepared as mentioned above encoding the protein of the present invention derived from animals except mice (non-self protein) have been integrated into its endogenous locus of the mouse. The transgenic mouse expresses the non-self protein and secretes the protein into its body.

The transgenic mouse can be prepared according to the method as usually used for producing a transgenic animal (for example, see "Newest Manual of Animal Cell Experiment", LIC press, Chapter 7, pp.361–408, (1990)).

Specifically, for example, embryonic stem cells (ES cells) obtained from normal mouse blastocysts are transformed with an expression vector in which the gene encoding human-derived polypeptide of the present invention (i.e. "human JTT-1 antigen") has been operably inserted. ES cells in which the gene encoding the human-derived polypeptide of the present invention has been integrated into the endogenous gene are screened by the usual method. Then, the ES cells screened are microinjected into a fertilized egg obtained from another normal mouse (blastocyst) (Proc.

Natl. Acad. Sci. USA, Vol.77, No.12, pp.7380–7384 (1980); U.S. Pat. No. 4,873,191). The blastocyst is transplanted into the uterus of another normal mouse as the foster mother. Then, founder mice (progeny mice) are born from the foster mother mouse. By mating the founder mice with normal mice, heterogeneic transgenic mice are obtained. By mating the heterogeneic transgenic mice with each other, homogeneic transgenic mice are obtained according to Mendel's laws.

"Knockout mouse" of the present invention is a mouse wherein the endogenous gene encoding the mouse-derived protein of the present invention has been knocked out (inactivated). It can be prepared, for example, by positive-negative selection method in which homologous recombination is applied (U.S. Pat. Nos. 5,464,764; 5,487,992; 5,627,059; Proc. Natl. Acad. Sci. USA, Vol.86, pp.8932–8935 (1989); Nature, Vol.342, pp.435–438 (1989); etc.).

The "antibody" of the present invention can be a polyclonal antibody (antiserum) or a monoclonal antibody, and preferably a monoclonal antibody.

Specifically, it is an antibody reactive to (against, which binds to) the above-mentioned protein or its fragment of the present invention.

The antibody of the present invention can be natural antibodies obtained by immunizing mammals such as mice, rats, hamsters, guinea pigs, and rabbits with an immunogen (antigen), such as the protein of the present invention (natural, recombinant, or synthetic ones), cells expressing the protein of the present invention, or transformants overexpressing the designed protein on the surface thereof prepared using recombinant DNA technology as described above on the cell surface. The antibody of the present invention also includes chimeric antibodies and humanized antibodies (CDR-grafted antibodies) that can be produced by recombinant DNA technology, and human antibodies that can be produced using human antibody-producing transgenic animals.

The monoclonal antibody includes those having any one isotype of IgG, IgM, IgA, IgD, or IgE. IgG or IgM is preferable.

The polyclonal antibody (antisera) or monoclonal antibody of the present invention can be produced by the known methods. Namely, a mammal, preferably, a mouse, rat, hamster, guinea pig, rabbit, cat, dog, pig, goat, horse, or cattle, or more preferably, a mouse, rat, hamster, guinea pig, or rabbit is immunized, for example, with an immunogen (antigen) mentioned above with Freund's adjuvant, if necessary. The polyclonal antibody can be obtained from the antiserum obtained from the animal so immunized. In addition, the monoclonal antibodies are produced as follows. Hybridomas are prepared from the antibody-producing cells obtaind from the animal so immunized and myeloma cells that are not capable of producing autoantibodies. The hybridomas are cloned, and clones producing the monoclonal antibodies showing the specific affinity to the antigen used for immunizing the mammal are screened.

Specifically, the monoclonal antibody can be produced as follows. Immunizations are performed by injecting or implanting once or several times the protein of the present invention, cells expressing the protein and so on as mentioned above as an immunogen, if necessary, with Freund's adjuvant, subcutaneously, intramuscularly, intravenously, through the footpad, or intraperitoneally into a mouse, rat, hamster, guinea pig, or rabbit, preferably a mouse, rat, or hamster (including a transgenic animal generated so as to produce antibodies derived from another animal such as the transgenic mouse producing human antibody). Usually, immunizations are performed once to four times every one to fourteen days after the first immunization. Antibody-producing cells are obtained from the mammal so immunized in about one to five days after the last immunization.

Hybridomas that secrete a monoclonal antibody can be prepared by the method of Köhler and Milstein (Nature, Vol.256, pp.495–497 (1975)) and by its modified method. Namely, hybridomas are prepared by fusing antibody-producing cells contained in a spleen, lymph node, bone marrow, or tonsil obtained from the mammal immunized as mentioned above, preferably a spleen, with myelomas without autoantibody-producing ability, which are derived from, preferably, a mammal such as a mouse, rat, guinea pig, hamster, rabbit, or human, or more preferably, a mouse, rat, or human.

For example, mouse-derived myeloma P3/X63-AG8.653 (653), P3/NSI/1-Ag4-1 (NS-1), P3/X63-Ag8.U1 (P3U1), SP2/0-Agl4 (Sp2/0, Sp2), PAI, F0, or BW5147, rat-derived myeloma 210RCY3-Ag.2.3., or human-derived myeloma U-266AR1, GM1500-6TG-A1-2, UC729-6, CEM-AGR, D1R11, or CEM-T15 can be used as a myeloma used for the cell fusion.

Hybridoma clones producing monoclonal antibodies can be screened by cultivating hybridomas, for example, in microtiter plates and by measuring the reactivity of the culture supernatant in the well in which hybridoma growth is observed, to the immunogen used for the immunization mentioned above, for example, by enzyme immunoassay such as RIA and ELISA.

The monoclonal antibodies can be produced from hybridomas by cultivating the hybridomas in vitro or in vivo such as in the ascites fluid of a mouse, rat, guinea pig, hamster, or rabbit, preferably a mouse or rat, more preferably mouse and isolating the antibodies from the resulting the culture supernatant or ascites fluid of a mammal.

Cultivating hybridomas in vitro can be performed depending on the property of cells to be cultured, on the object of a test study, and on the various conditions of a cultivating method, by using known nutrient media or any nutrient media derived from known basal media for growing, maintaining, and storing the hybridomas to produce monoclonal antibodies in culture supernatant.

Examples of basal media are low calcium concentration media such as Ham'F12 medium, MCDB153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Monoclonal antibodies can be isolated and purified from the culture supernatant or ascites fluid mentioned above by saturated ammonium sulfate precipitation, euglobulin precipitation method, caproic acid method, caprylic acid method, ion exchange chromatography (DEAE or DE52), affinity chromatography using anti-immunoglobulin column or protein A column.

The "chimeric antibody" of the present invention is a monoclonal antibody prepared by genetic engineering, and specifically means a chimeric antibody such as mouse/human chimeric monoclonal antibody whose variable regions or the other regions are derived from mouse immunoglobulin and whose constant regions are derived from human immunoglobulin.

The constant region derived from human immunoglobulin has the amino acid sequence inherent in each isotype such as IgG, IgM, IgA, IgD, and IgE. The constant region of the recombinant chimeric monoclonal antibody of the present invention can be that of human immunoglobulin belonging to any isotype. Preferably, it is the constant region of human IgG.

The chimeric monoclonal antibody of the present invention can be produced, for example, as follows. Needless to say, the production method is not limited thereto.

A mouse/human chimeric monoclonal antibody can be prepared, referring to Experimental Medicine: SUPPLEMENT, Vol.1.6, No.10 (1988); and examined published Japanese patent application (JP-B) No. Hei 3-73280. Namely, it can be prepared by operably inserting CH gene (C gene encoding the constant region of H chain) obtained from the DNA encoding human immunoglobulin downstream of active VH genes (rearranged VDJ gene encoding the variable region of H chain) obtained from the DNA encoding a mouse monoclonal antibody isolated from the hybridoma producing the mouse monoclonal antibody, and CL gene (C gene encoding the constant region of L chain) obtained from the DNA encoding human immunoglobulin downstream of active VL genes (rearranged VJ gene encoding the variable region of L chain) obtained from the DNA encoding the mouse monoclonal antibody isolated from the hybridoma, into the same or different vectors so as for them to be expressed, following by transforming host cells with the expression vector, and then by cultivating the transformants.

Specifically, DNAs are first extracted from mouse monoclonal antibody-producing hybridomas by the usual method, digested with appropriate restriction enzymes (for example, EcoRI and HindIII), electrophoresed (using, for example, 0.7% agarose gel), and analyzed by Southern blotting. After an electrophoresed gel is stained, for example, with ethidium bromide and photographed, the gel is given with marker positions, washed twice with water, and soaked in 0.25 M HCl for 15 minutes. Then, the gel is soaked in 0.4 N NaOH solution for 10 minutes with gently stirring. The DNAs are transferred to a filter for 4 hours by the usual method. The filter is recovered and washed twice with 2×SSC. After the filter is sufficiently dried, it is baked at 75° C. for 3 hours. After baking, the filter is treated with 0.1×SSC/0.1% SDS at 65° C. for 30 minutes. Then, it is soaked in 3×SSC/0.1% SDS. The filter obtained is treated with prehybridization solution in a plastic bag at 65° C. for 3 to 4 hours.

Next, $^{32}$P-labeled probe DNA and hybridization solution are added to the bag and reacted at 65° C. about 12 hours. After hybridization, the filter is washed under appropriate salt concentration, reaction temperature, and time (for example, 2×SSC-0.1% SDS, room temperature, 10 minutes). The filter is put into a plastic bag with a little 2×SSC, and subjected to autoradiography after the bag is sealed.

Rearranged VDJ gene and VJ gene encoding H chain and L chain of a mouse monoclonal antibody are identified by Southern blotting mentioned above. The region comprising the identified DNA fragment is fractioned by sucrose density gradient centrifugation and inserted into a phage vector (for example, Charon 4A, Charon 28, λEMBL3, λEMBL4, etc.). E. coli (for example, LE392, NM539, etc.) is transformed with the phage vector to generate a genomic library. The genomic library is screened by plaque hybridization such as Benton-Davis method (Science, Vol.196, pp.180–182 (1977)) using appropriate probes (H chain J gene, L chain (κ) J gene, etc.) to obtain positive clones comprising rearranged VDJ gene or VJ gene. By making the restriction map and determining the nucleotide sequence of the clones obtained, it is confirmed that genes comprising the desired, rearranged VH (VDJ) gene or VL (VJ) gene are obtained.

Separately, human CH gene and human CL gene used for chimerization are isolated. For example, when a chimeric antibody with human IgG1 is produced, Cγ1 gene as a CH gene, and Cκ gene as a CL gene, are isolated. These genes can be isolated from human genomic library with mouse Cγ1 gene and mouse Cκ gene, corresponding to human Cγ1 gene and human Cκ gene, respectively, as probes, taking advantage of high homology between the nucleotide sequences of mouse immunoglobulin gene and that of human immunoglobulin gene.

Specifically, DNA fragments comprising human Cκ gene and an enhancer region are isolated from human λ Charon 4A HaeIII-AluI genomic library (Cell, Vol.15, pp.1157–1174 (1978)), for example, with a 3 kb HindIII-BamHI fragment of clone Ig146 (Proc. Natl. Acad. Sci. USA, Vol.75, pp.4709–4713 (1978)) and a 6.8 kb EcoRI fragment of clone MEP10 (Proc. Natl. Acad. Sci. USA, Vol.78, pp.474–478 (1981)) as probes. In addition, for example, after human fetal hepatocyte DNA is digested with HindIII and fractioned by agarose gel electrophoresis, a 5.9 kb fragment is inserted into λ788 and then human Cγ1 gene is isolated with the probes mentioned above.

Using mouse VH gene, mouse VL gene, human CH gene, and human CL gene so obtained, and taking promoter region and enhancer region into consideration, human CH gene is inserted downstream mouse VH gene and human CL gene is inserted downstream mouse VL gene into an expression vector such as pSV2gpt or pSV2neo with appropriate restriction enzymes and DNA ligase by the usual method. In this case, chimeric genes of mouse VH gene/human CH gene and mouse VL gene/human CL gene can be respectively inserted in the same expression vector or in different expression vectors.

Chimeric gene-inserted expression vector(s) thus prepared are introduced into myelomas that do not produce antibodies, for example, P3X63.Ag8.653 cells or SP210 cells by protoplast fusion method, DEAE-dextran method, calcium phosphate method, or electroporation method. The transformants are screened by cultivating in media containing a drug corresponding to the drug resistance gene inserted into the expression vector and, then, cells producing desired chimeric monoclonal antibodies are obtained.

Desired chimeric monoclonal antibodies are obtained from the culture supernatant of antibody-producing cells thus screened.

The "humanized antibody (CDR-grafted antibody)" of the present invention is a monoclonal antibody prepared by genetic engineering and specifically means a humanized monoclonal antibody wherein a portion or the whole of the complementarity determining regions of the hypervariable region are derived from the complementarity determining regions of the hypervariable region from a mouse monoclonal antibody, the framework regions of the variable region are derived from the framework regions of the variable region from human immunoglobulin, and the constant region is derived from human a constant region from immunoglobulin.

The complementarity determining regions of the hypervariable region exists in the hypervariable region in the variable region of an antibody and means three regions which directly and complementary binds to an antigen (complementarity-determining residues, CDR1, CDR2, and CDR3). The framework regions of the variable region means four comparatively conserved regions lying upstream, downstream or between the three complementarity determining regions (framework region, FR1, FR2, FR3, and FR4).

In other words, a humanized monoclonal antibody means that in which the whole region except a portion or the whole of the complementarity determining regions of the hypervariable region of a nonhuman mammal-derived monoclonal antibody have been replaced with their corresponding regions derived from human immunoglobulin.

The constant region derived from human immunoglobulin has the amino acid sequence inherent in each isotype such as IgG (IgG1, IgG2, IgG3, IgG4), IgM, IgA, IgD, and IgE. The constant region of a humanized monoclonal antibody in the present invention can be that from human immunoglobulin belonging to any isotype. Preferably, it is the constant region of human IgG. The framework regions of the constant region derived from human immunoglobulin are not particularly limited.

The humanized monoclonal antibody of the present invention can be produced, for example, as follows. Needless to say, the production method is not limited thereto.

For example, a recombinant humanized monoclonal antibody derived from mouse monoclonal antibody can be prepared by genetic engineering, referring to unexamined Japanese patent publication (JP-WA) No. Hei 4-506458 and unexamined Japanese patent publication (JP-A) No. Sho 62-296890. Namely, at least one mouse H chain CDR gene and at least one mouse L chain CDR gene corresponding to the mouse H chain CDR gene are isolated from hybridomas producing mouse monoclonal antibody, and human H chain gene encoding the whole regions except human H chain CDR corresponding to mouse H chain CDR mentioned above and human L chain gene encoding the whole region except human L chain CDR correspond to mouse L chain CDR mentioned above are isolated from human immunoglobulin genes.

The mouse H chain CDR gene(s) and the human H chain gene(s) so isolated are operably inserted into an appropriate vector so that they can be expressed. Similarly, the mouse L chain CDR gene(s) and the human L chain gene(s) are operably inserted into another appropriate vector so that they can be expressed. Alternatively, the mouse H chain CDR gene(s)/human H chain gene(s) and mouse L chain CDR gene(s)/human L chain gene(s) can be operably inserted into the same expression vector so that they can be expressed. Host cells are transformed with the expression vector thus prepared to obtain transformants producing humanized monoclonal antibody. By cultivating the transformants, desired humanized monoclonal antibody is obtained from culture supernatant.

The "human monoclonal antibody" of the present invention is immunoglobulin in which the entire regions comprising the variable and constant region of H chain, and the variable and constant region of L chain constituting immunoglobulin are derived from the gene encoding human immunoglobulin. The human antibody can be produced in the same way as the production method of polyclonal or monoclonal antibodies mentioned above by immunizing, with an antigen, a transgenic animal which for example, at least human immunoglobulin gene(s) have been integrated into the locus of a non-human mammal such as a mouse by the usual method. For example, a transgenic mouse producing human antibodies is prepared by the methods described in Nature Genetics, Vol.15, pp.146–156 (1997); Nature Genetics, Vol.7, pp.13–21 (1994); JP-WA Nos. Hei4-504365, International patent publication No. WO94/25585; Nikkei Science, No.6, pp.40–50 (1995); Nature, Vol.368, pp.856–859 (1994); and JP-WA No. Hei 6-500233.

The "portion of an antibody" used in the present invention means a partial region of the antibody, preferably monoclonal antibody of the present invention as mentioned above, and specifically, means F(ab')$_2$, Fab', Fab, Fv (variable fragment of antbody), sFv, dsFv (disulfide stabilized Fv), or dAb (single domain antibody) (Exp. opin. Ther. Patents, Vol.6, No.5, pp.441–456 (1996)).

"F(ab')$_2$" and "Fab'" can be produced by treating immunoglobulin (monoclonal antibody) with a protease such as pepsin and papain, and means an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CH$\gamma$1 ($\gamma$1 region in the constant region of H chain) are connected at their C terminal regions through a disulfide bond. Each of such two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')$_2$.

The "pharmaceutical composition" of the present invention comprises any one of the protein, protein fragment, fusion protein antibody, or portion of an antibody of the present invention as defined above; and a pharmaceutically acceptable carrier.

The "pharmaceutically acceptable carrier" includes a excipieut, a diluent, an expander, a decomposition agent, a stabilizer, a preservative, a buffer, an emulsifier, an aromatic, a colorant, a sweetener, a viscosity increasing agent, a flavor, a solubility increasing agent, or other additives. Using one or more of such carriers, a pharmaceutical composition can be fomulated into tablets, pills, powders, granules, injections, solutions, capsules, troches, elixirs, suspensions, emulsions, or syrups. The pharmaceutical composition can be administered orally or parenterally. Other forms for parenteral administration include a solution for external application, suppository for rectal administration, and pessary, prescribed by the usual method, which comprises one or more active ingredient.

The dosage can vary depending on the age, sex, weight, and symptom of a patient, effect of treatment, administration route, period of treatment, or the kind of active ingredient (polypeptide or antibody mentioned above) contained in the pharmaceutical composition. Usually, the pharmaceutical composition can be administered to an adult in a dose of 10 $\mu$g to 1000 mg (or 10 $\mu$g to 500 mg) per one administration. Depending on various conditions, the dosage less than that mentioned above may be sufficient in some cases, and the dosage more than that mentioned above may be necessary in other cases.

In particular, the injection. can be produced by dissolving or suspending the antibody in a non-toxic, pharmaceutically acceptable carrier such as physiological saline or commercially available distilled water for injection with adjusting a concentration to 0.1 $\mu$g antibody/ml carrier to 10 mg antibody/ml carrier. The injection thus produced can be administered to a human patient in need of treatment in a dose of 1 $\mu$g to 100 mg/kg body weight, preferably 50 $\mu$g to 50 mg/kg body weight once or more times a day. Examples of administration route are medically appropriate administration routes such as intravenous injection, subcutaneous injection, intradermal injection, intramuscular injection, or intraperitoneal injection, preferably intravenous injection.

The injection can also be prepared into a non-aqueous diluent (for example, propylene glycol, polyethylene glycol, vegetable oil such as olive oil, and alcohol such as ethanol), suspension, or emulsion.

The injection can be sterilized by filtration with a bacteria-non-penetrated filter, by mixing bacteriocide, or by irradiation. The injection can be produced in the form that is prepared upon use. Namely, it is freeze-dried to be a sterile solid composition, and can be dissolved in sterile distilled water for injection or another solvent before use.

The pharmaceutical composition of the present invention can be used to treat or prevent arteriosclerosis and restenosis after the treatment of artery occlusion, such as PTCA.

The numerals indicate days from the exfoliation of the artery endothelium using a balloon catheter to the removal of the artery; thus, the figure shows the time course of the cDNA expression.

Figure 2:
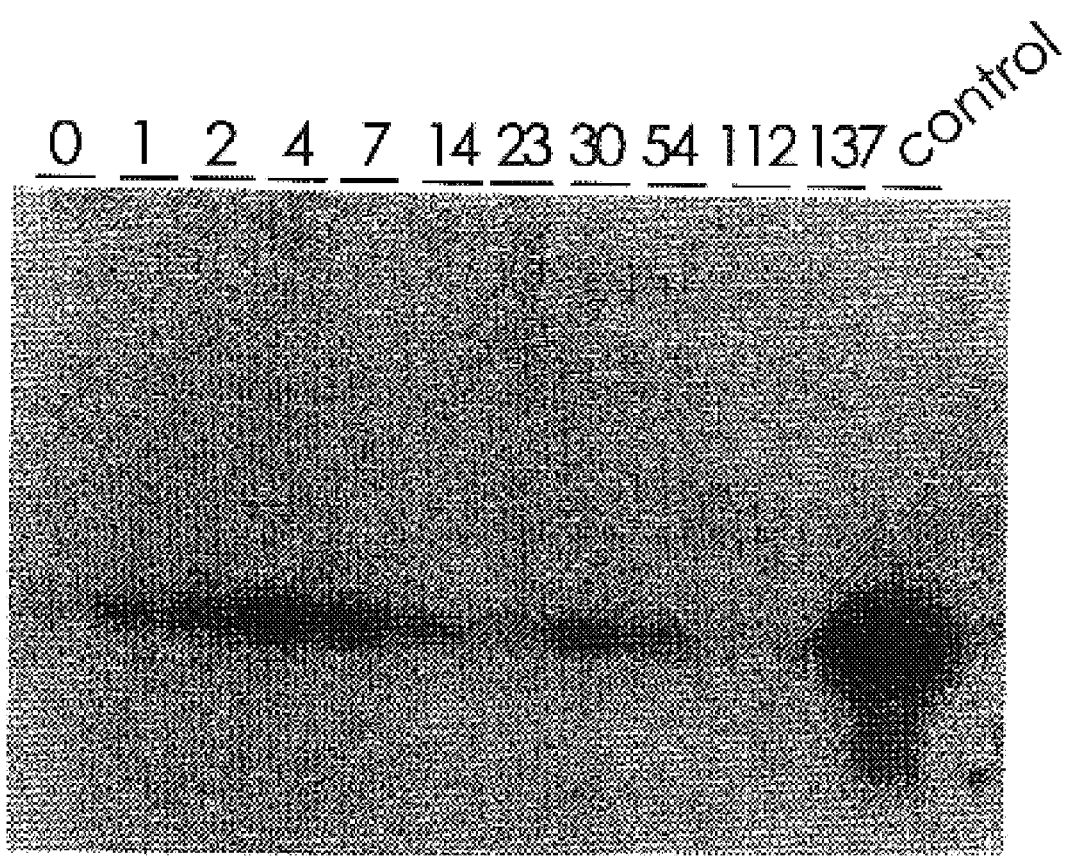

FIG. 2 is a photograph showing an electrophoresis image of rabbit BA0306 cDNA samples obtained by RT-PCR.

The numerals indicate days from the exfoliation of the artery endothelium using a balloon catheter to the removal of the artery; thus, the figure shows the time course of the cDNA expression.

Figure 3:
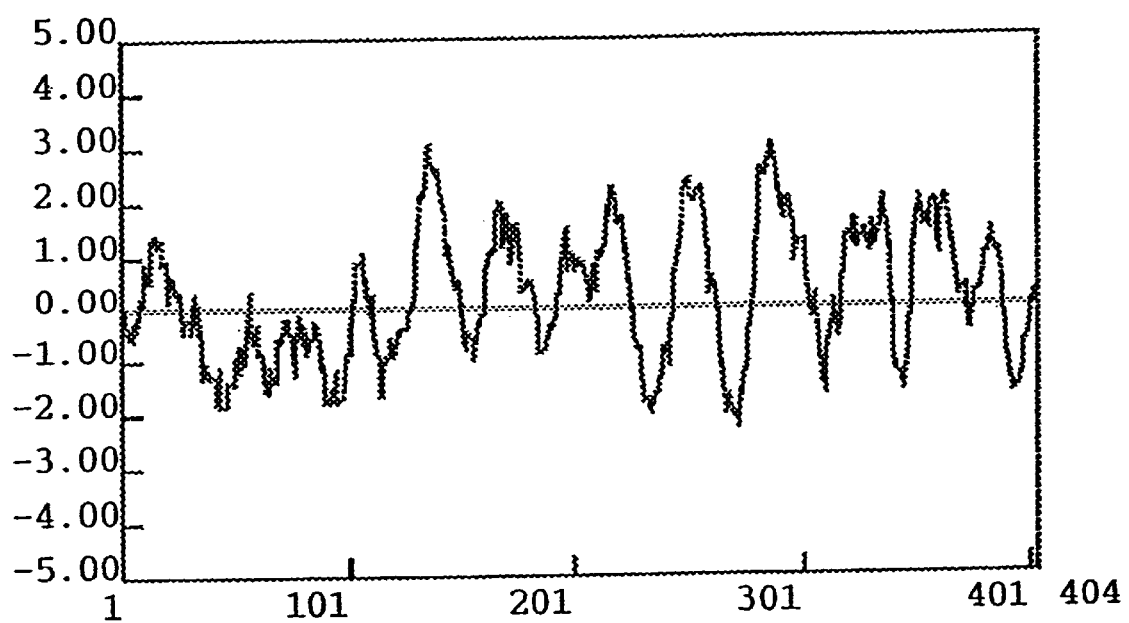

FIG. 3 shows a plot of the hydrophobicity and hydrophilicity of the amino acid residues composing rabbit BA2303 protein.

Figure 4:
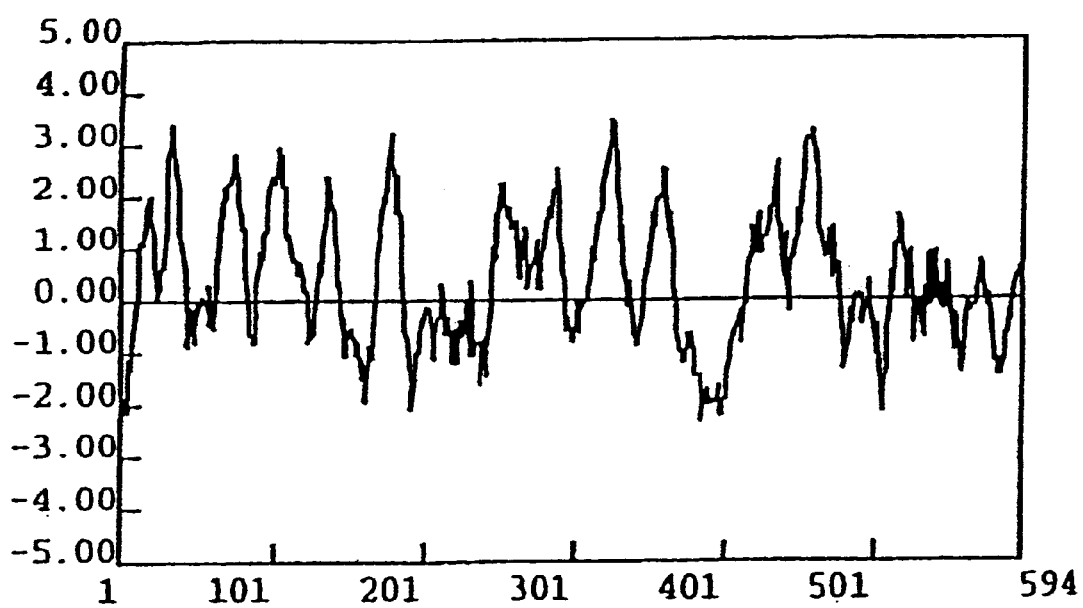

FIG. 4 shows a plot of the hydrophobicity and hydrophilicity of the amino acid residues composing human BA0306 protein.

Figure 5:
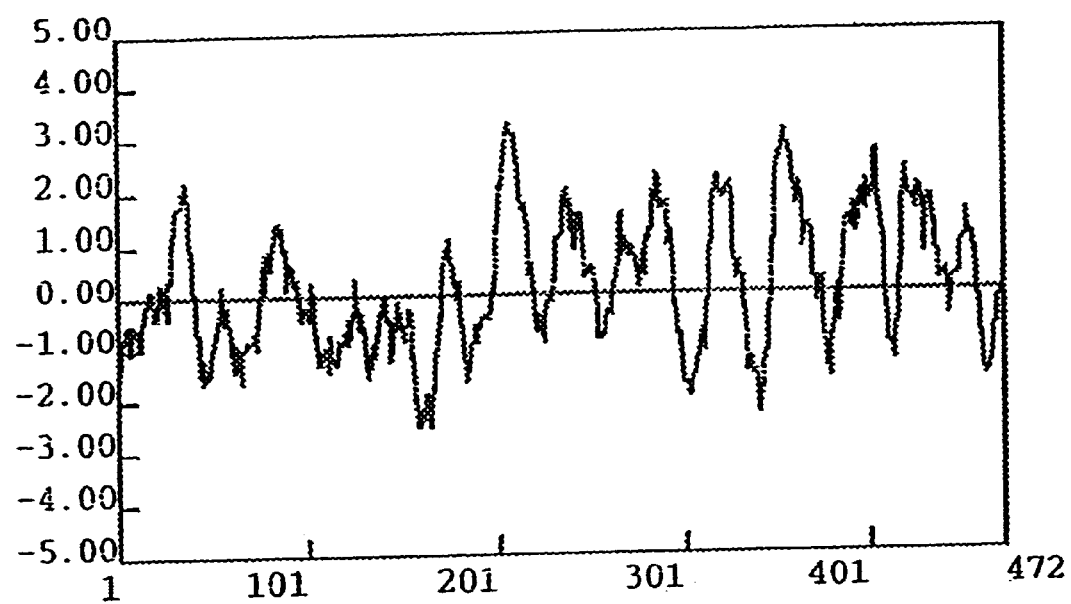

FIG. 5 shows a plot of the hydrophobicity and hydrophilicity of the amino acid residues composing human BA2303 protein.

Figure 6:
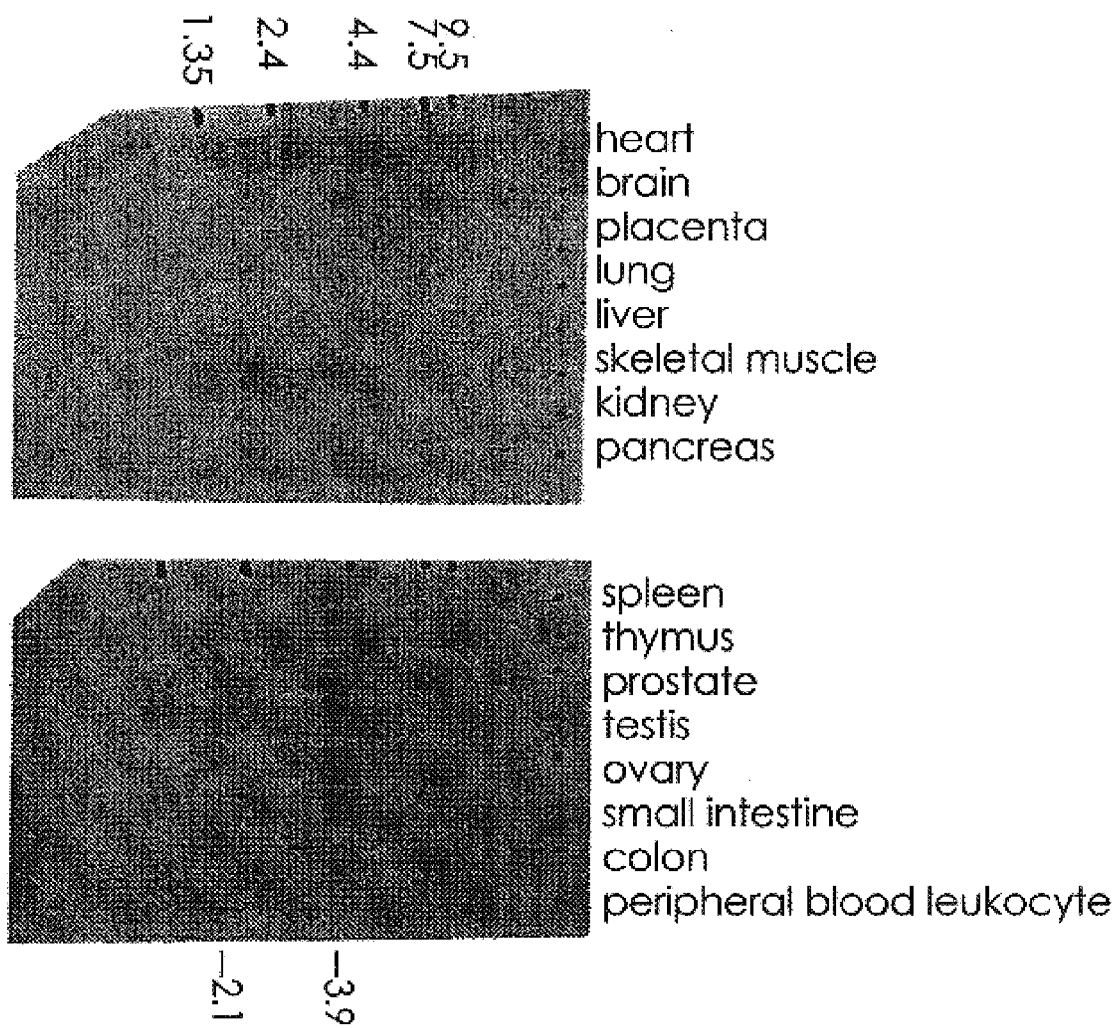

FIG. 6 is a photograph showing the result of Northern blot analysis of the expression of human BA2303 mRNA in various human tissues.

Figure 7:
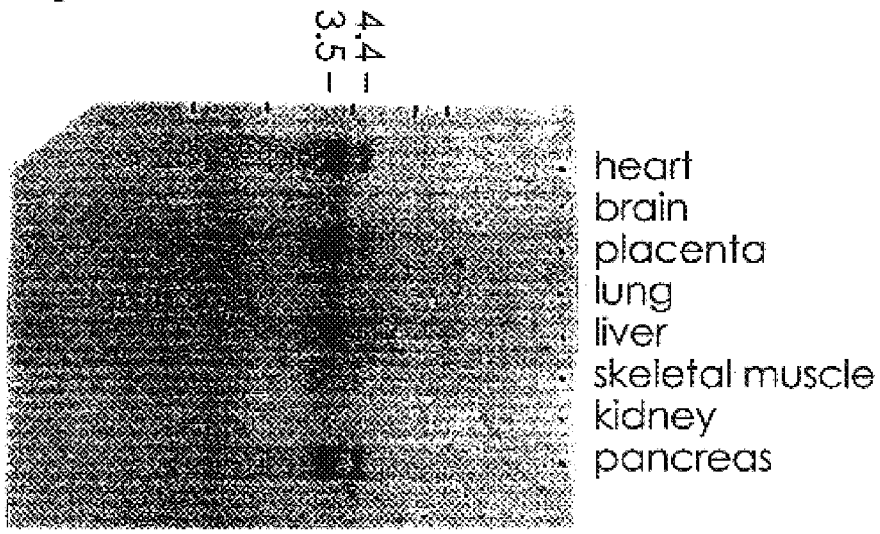
Figure 7:
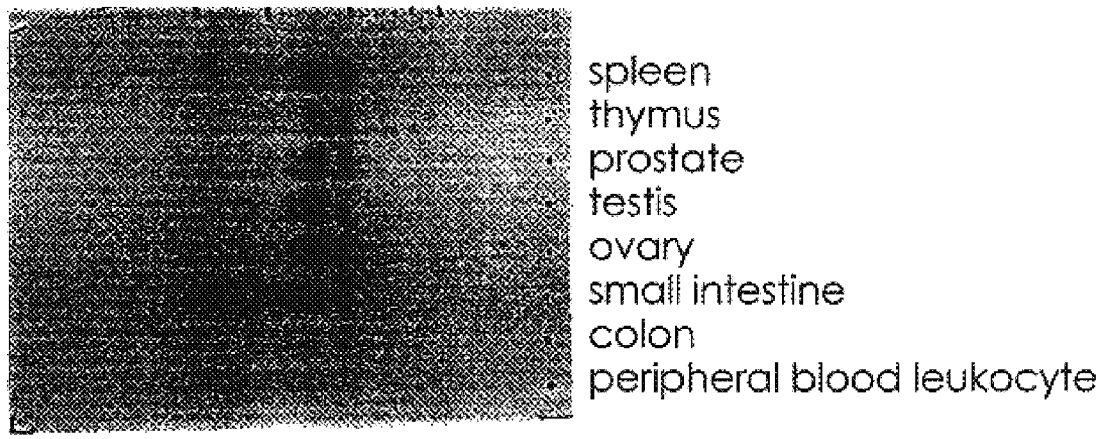

FIG. 7 is a photograph showing the result of Northern blot analysis of the expression of human BA0306 mRNA in various human tissues.

Figure 8:
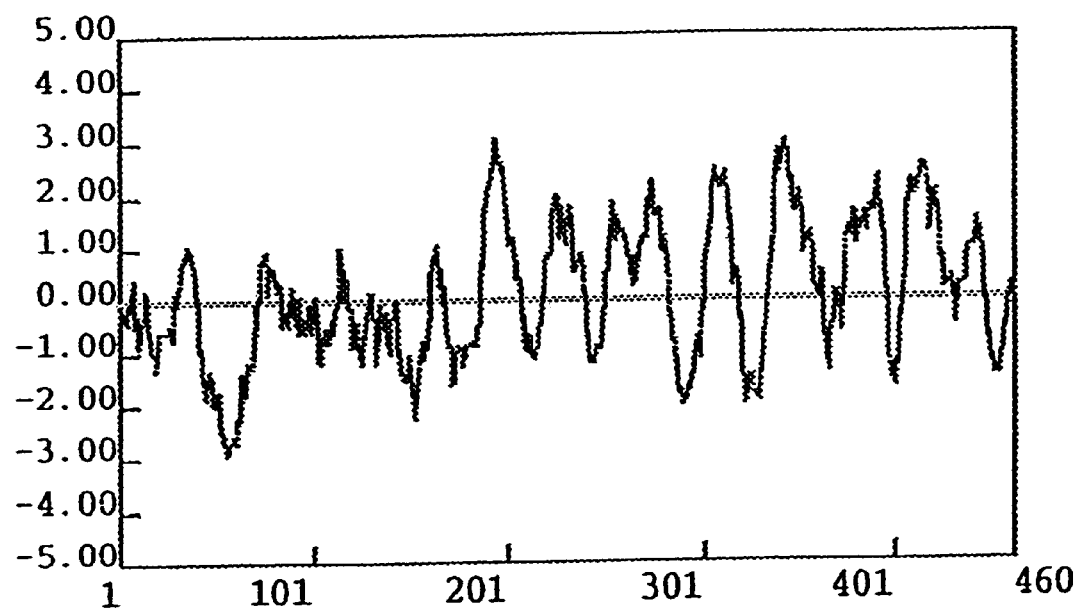

FIG. 8 shows a plot of the hydrophobicity and hydrophilicity of the amino acid residues composing mouse BA2303 protein.

Figure 9:
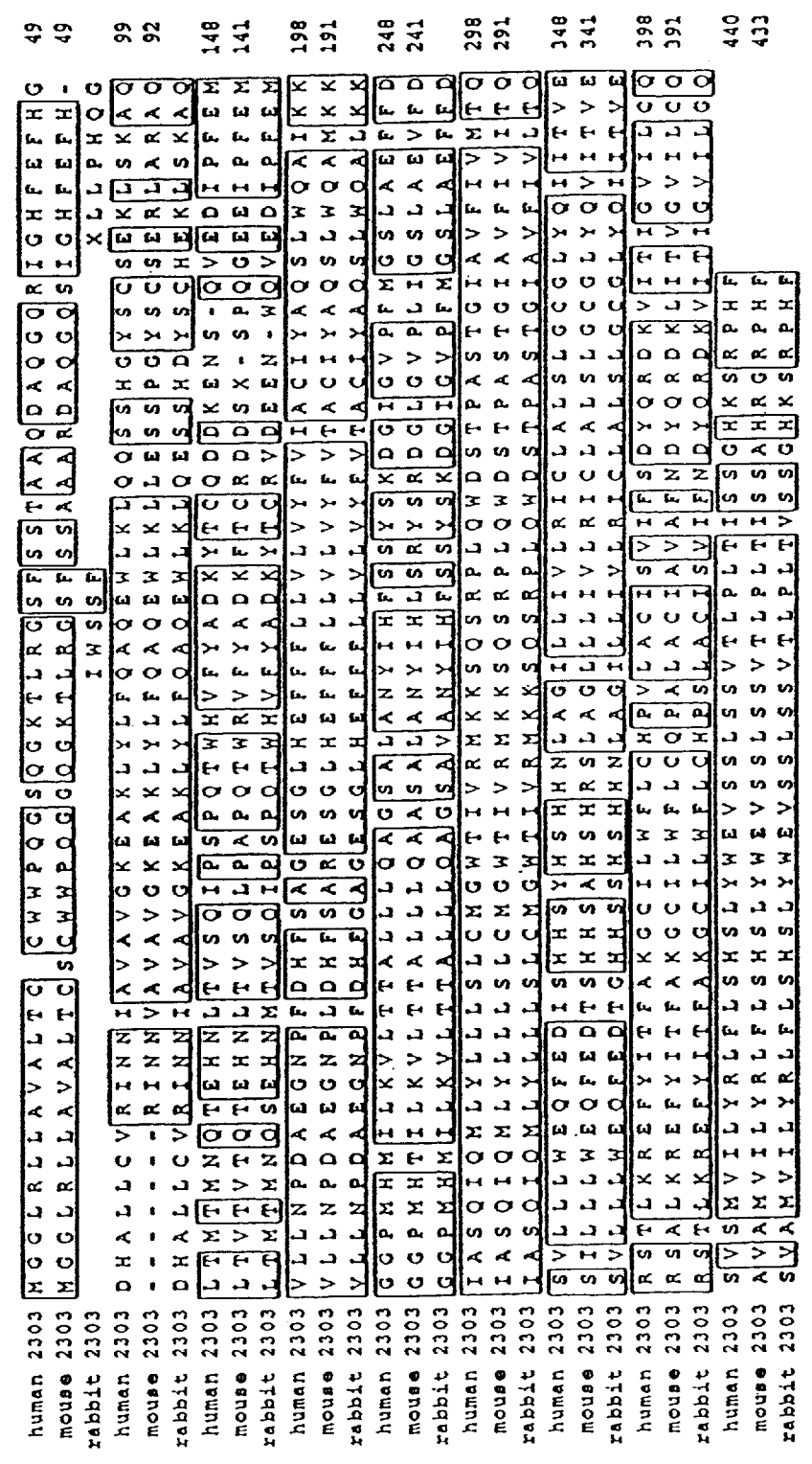

FIG. 9 shows the sequence homology at the amino acid level between BA2303 proteins from rabbit, (SEQ ID NO: 2) human, (SEQ ID NO: 40) and mouse (SEQ ID NO: 6).

Figure 10:
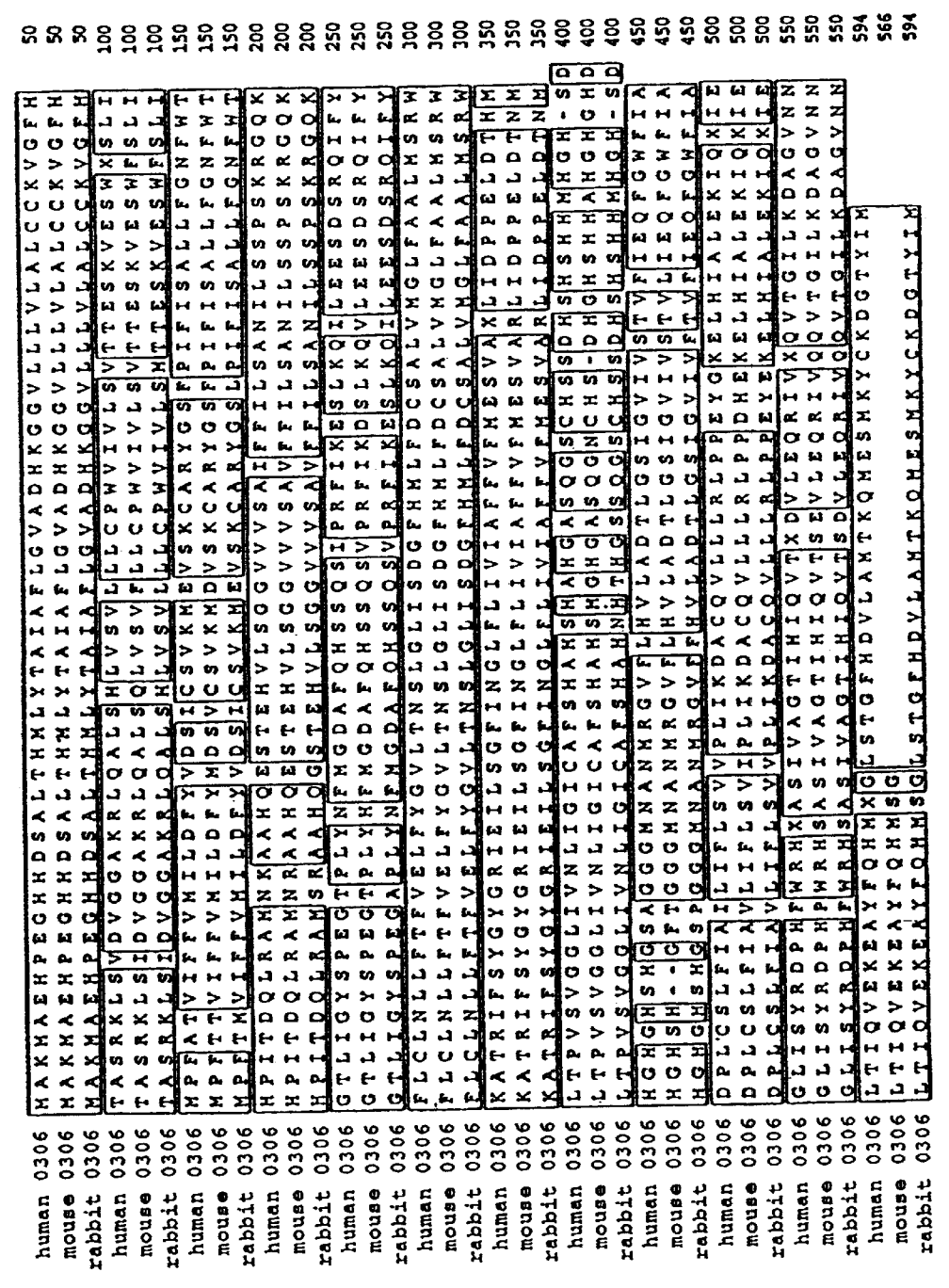

FIG. 10 shows the sequence homology at the amino acid level between BA0306 proteins from rabbit (SEQ ID NO: 8), human (SEQ ID NO: 10), and mouse (SEQ ID NO: 28).

Figure 11:
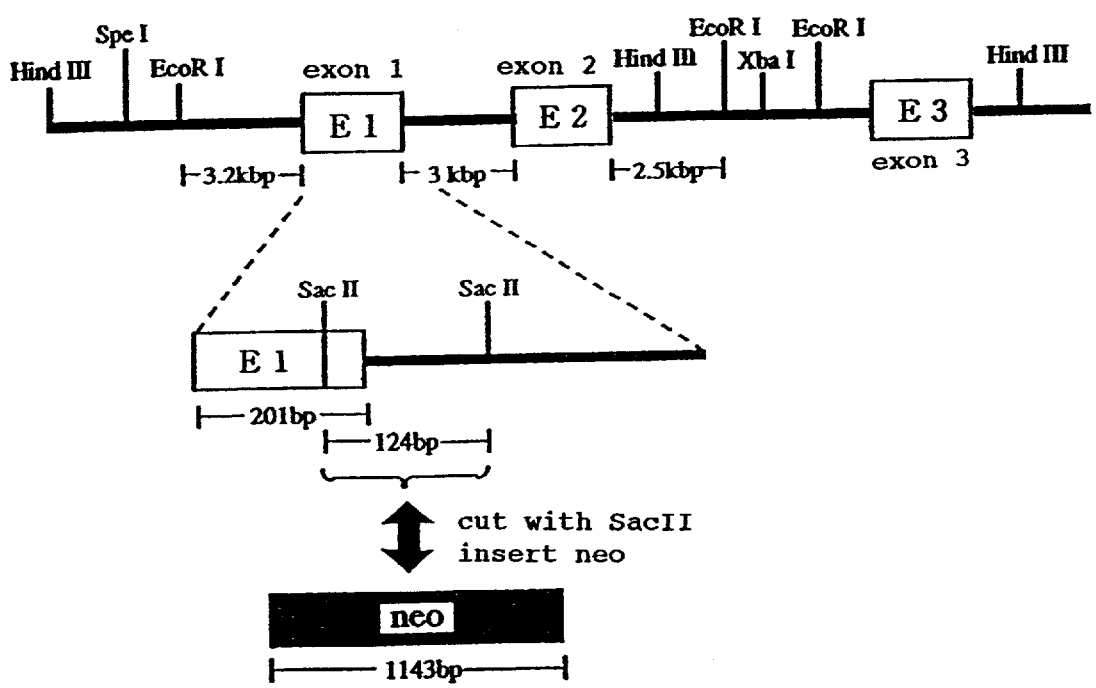

FIG. 11 schematically shows the structures of mouse genomic DNA containing exons that encode mouse BA2303 protein, and of the targeting vector for knockout mice generation.

Figure 12:
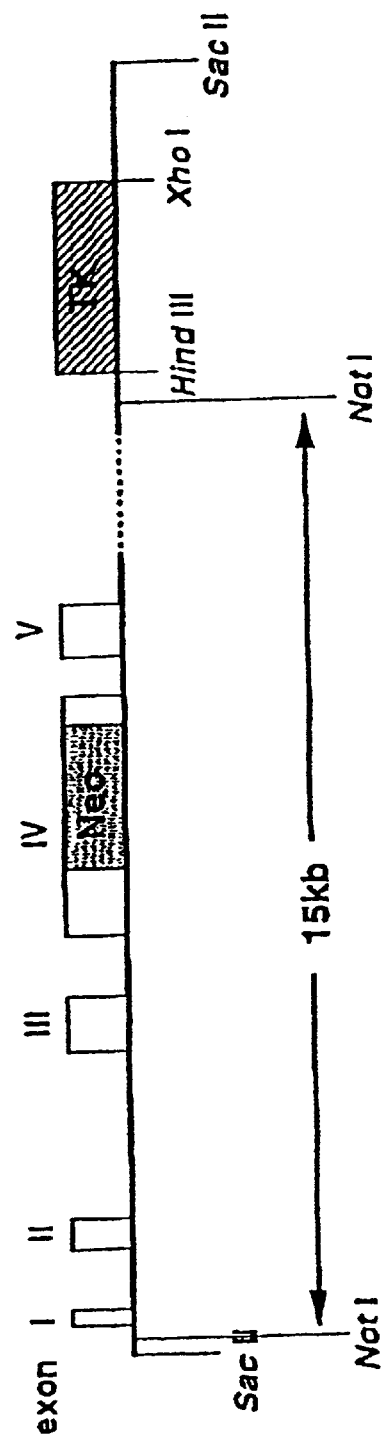

FIG. 12 schematically shows the structures of mouse genomic DNA containing exons that encode mouse BA0306 protein, and of the targeting vector for knockout mice generation.

BEST MODE FOR IMPLEMENTING THE INVENTION

The present invention is illustrated in detail below with reference to examples, but is not to be construed as being limited thereto.

EXAMPLE 1
Generation of a Rabbit Model Whose Aortal Endothelium is Detached by PTCA According to the method described in "Protocols in Circulation Research" (Jikken-Igaku Zoukan (1996) Vol.14 (12), 87), a balloon catheter was inserted into the thoracic artery of Japanese white rabbits by surgical operation and was inflated to perform PTCA. The artery including the operation site was removed at certain periods from day 1 to six months after PTCA.

EXAMPLE 2
Preparation of Total RNA from Removed Aortae

The aorta was removed at 1, 2, 4, 7, 14, 23, 30, 54, 112, and 137 days after PTCA, and total RNA was prepared from the aortae by the standard method using the TRIZOL reagent (GIBCO BRL).

Also, the aorta was removed from a normal Japanese white rabbit, which was not subjected to PTCA, and total RNA was prepared as described.

EXAMPLE 3
cDNA Synthesis

Total RNAs (each 2 µl, 1 µg/ml) sampled with the passage of time or mRNA samples (each 2 µl, 0.5 µg/ml), which were obtained in Example 2, were dissolved in diethyl pirocarbonate (DEPC)-treated distilled water (8 µl). Anchor primer (GT15MA, 1 µl, 25 pmol/µl) was added to make the total volume 10 µl, and the mixture was then incubated 5 min at 65° C. The samples were placed on ice immediately after completion of the incubation.

Then, 5×first strand buffer (4 µl, composition: 0.25 M Tris-HCl (pH 7.5), 0.375 M KCl, 0.05 M DTT, 0.015 M MgCl$_2$), 0.1 M DTT (2 µl), 250 µM dNTP (1 µl), distilled water (1 µl), and reverse transcriptase (Superscript, GIBCO BRL, 1 µl, 200 U/µl) were added to make the total volume 20 µl. cDNA was synthesized by incubating the reaction mixture for 1 hr at 42° C., and then DEPC-treated water (30 µl) was added to make the final volume 50 µl.

EXAMPLE 4
Analysis of the Time Course of Gene Expression

The time course of gene expression after PTCA was analyzed by the standard method using differential display (Nucleic Acid Research (1993) Vol. 21(18), 4272–4280; Science (1992) Vol. 257, 967–971), and RT-PCR (reverse transcription-polymerase chain reaction; "PCR and its Application" (Jikken-Igaku Zoukan (1990) Vol. 8(9); "Gene Amplification PCR Method/Principles and Novel Applications" Kyoritsu-Syuppan (1992)).

One hundred-fold dilution of the cDNA samples (each time point) which were prepared in Example 3 was used as a template for PCR in differential display. Fifty fold dilution was used for cDNA samples that were synthesized from mRNA (each time point).

The template cDNA (each 2 µl) was mixed with distilled water (10.75 µl), 10×EX Taq buffer (2 µl), 25 µM dNTP (1.5 µl), arbitrary primer (sequence: GATCAATCGC, 1 µl, 25 pmol/µl), anchor primer (1 µl, 25 pmol/µl), EX Taq DNA polymerase (0.25 µl), and α35S-dATP (1.5 µl, 10 mCi/ml, Amersham) to make the total volume 20 µl. PCR was carried out with a cycle of 95° C. for 3 min, 40° C. for 5 min, 72° C. for 5 min; 40 cycles of 95° C. for 30 sec, 40° C. for 2 min, 72° C. for 1 min; and a step of 72° C. for 5 min, and then the samples were kept at 4° C.

Each of the resulting PCR products was mixed with stop buffer (5 µl, composition: formamide (30 ml), xylenecyanol (30 mg), bromophenol blue (10 mg), 0.5 M EDTA (200 µl, (pH 8.0)), and then, 3.5 µl of each resulting mixture was subjected to sequence gel electrophoresis on a 6% acrylamide gel (composition (in 500 ml total): urea (240 g), 10×TBE (50 ml), 40% acrylamide (75 ml, a mixture of 38% monoacrylamide and 2% bisacrylamide)). The result showed that there were two bands whose expression was changed in the time course.

Both bands were excised from the gel, and two DNA fragments containing the nucleotide sequences described in SEQ ID NO: 11 (178 bp) and SEQ ID NO: 12 (167 bp) were isolated according to the standard method ("Gene Engineering Handbook" Jikken-Igaku, Yodosya (1992)). The fragments were named as BA2303 (SEQ ID NO: 11), and BA0306 (SEQ ID NO: 12), respectively. To confirm the expression of the DNAs containing the two fragments in the time course, RT-PCR was performed using cDNA samples obtained in Example 3 (each time point) as a template.

For amplification of BA2303, synthetic DNA fragments described in SEQ ID NO: 13 and SEQ ID NO: 14 were used as forward and reverse primers, respectively.

For amplification of BA0306, synthetic DNA fragments described in SEQ ID NO: 21 and SEQ ID NO: 22 were used as forward and reverse primers, respectively.

Each template cDNA (3 µl) was mixed with 10×Vogelstein buffer (2.5 µl), 2.5 mM dNTP (1.5 µl), forward primer (1 µl, pmol/µl), reverse primer (1 µl, 25 pmol/µl), β-actin primer mix (each 25 pmol/µl), and EX Taq DNA polymerase (0.2 µl), adjusting the total volume to 25 µl. RT-PCR was carried out with a step of 94° C. for 2 min; 35 cycles of 94° C. for 3 sec, 55° C. for 30 sec, 72° C. for 1 min; and a step of 72° C. for 3 min, and then the samples were kept at 4° C.

Figure 1:
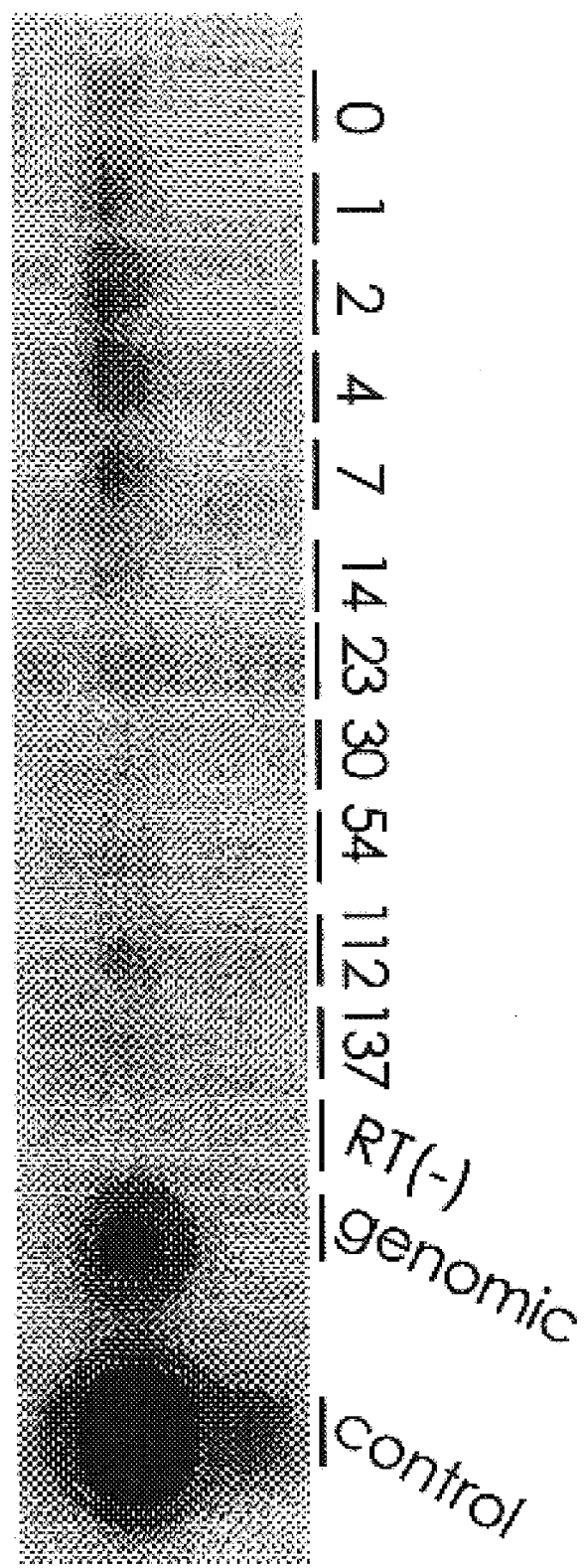
FIG. 1 is a photograph showing an electrophoresis image of rabbit BA2303 cDNA samples obtained by RT-PCR.

The obtained PCR products were separated by electrophoresis. The results were shown in FIGS. 1 (BA2303) and 2 (BA0306).

It was confirmed that the expression of BA2303 was increased from day 1 after the vascular endothelium was detached by PTCA, reached the maximal level from about day 2 to day 4, and continued until about day 7. The expression of BA0306 was detected over a period from day 1 to day 7 after PTCA, with peak expression at day 4.

EXAMPLE 5
Isolation of Long Strand cDNA

To isolate long strand cDNAs containing the two cDNA fragments (BA2303 and BA0306) obtained in Example 4, RACE (rapid amplification ends)-PCR was performed (Proc. Natl. Acad. Sci. USA (1988) Vol. 85, 8998–9002; "PCR Method for Gene Amplification/Principles and Novel Applications" Kyoritsu-Syuppan (1992)).

The PCR was performed twice using the Marathon cDNA Amplification Kit (CLONTECH) and the cDNA fragments obtained in Example 4 as a template.

BA2303 was amplified by PCR using synthetic DNA primers described in SEQ ID NO: 15 and SEQ ID NO: 19 (1), and with primers described in SEQ ID NO: 16 and SEQ ID NO: 20 (2), and subsequently using synthetic DNA primers described in SEQ ID NO: 17 and SEQ ID NO: 19 (3), and with primers described in SEQ ID NO: 18 and SEQ ID NO: 20 (4).

BA0306 was amplified by PCR using synthetic DNA primers described in SEQ ID NO: 23 and SEQ ID NO: 19 (1), and with primers described in SEQ ID NO: 24 and SEQ ID NO: 20 (2), and subsequently using synthetic DNA primers described in SEQ ID NO: 25 and SEQ ID NO: 19 (3), and with primers described in SEQ ID NO: 26 and SEQ ID NO: 20 (4). The above PCR produced DNAs described in SEQ ID NO: 1 (BA2303) and in SEQ ID NO: 7 (BA0306).

Analysis of the deduced amino acid sequence by plotting the hydrophilicity and hydrophobicity and by PSORT program suggested that BA2303 is a protein having seven transmembrane regions (FIG. 3).

EXAMPLE 6
Isolation of Human Counterpart Genes

The rabbit cDNAs (BA2303 and BA0306) obtained in Example were used as a probe to screen a human cDNA library (Fetal Brain, STRATAGENE, code:937-227) by colony hybridization according to the standard method ("Gene Engineering HandBook" Jikken-Igaku Zokan, Yodosya, (1992)). Thus, human homologues containing the nucleotide sequences described in SEQ ID NO: 3 (BA2303) and in SEQ ID NO: 9 (BA0306) were obtained.

Analysis of the deduced amino acid sequence of BA0306 protein by plotting the hydrophilicity and hydrophobicity and by PSORT program suggested that the protein has 10 transmembrane regions (FIG. 4). It is also suggested that human BA2303 is a protein having seven transmembrane regions as is the rabbit one obtained in Example 5 (FIG. 5).

Using the respective human DNA as a probe, the expression of mRNA of the two genes in various human tissues was examined using the Human Multiple Tissue Northern Blot (CLONTECH, code: #7760-1, #7759-1).

BA2303 mRNA was expressed in various human tissues as evident as two bands of about 3.9 kb and about 2.1 kb (FIG. 6).

BA0306 mRNA was also expressed in various human tissues as detected as two bands of about 3.5 kb and about 4.4 kb (FIG. 7).

Homology search between known proteins indicated that human BA0306 has sequence homology at the amino acid level with S. cerevisiae oxidative stress resistance protein, S. cerevisiae zinc/cadmium resistance protein, and heavy metal ion resistance protein, etc.

EXAMPLE 7
Isolation of Mouse BA2303 cDNA

As was described in Example 6, rabbit BA2303 gene was used as a probe for screening a mouse cDNA library (STRATAGENE, code: 936-309), and the mouse homologue containing the nucleotide sequence described in SEQ ID NO: 5 was isolated. The deduced amino acid sequence of the coding region was described in SEQ ID NO: 6.

Analysis of the deduced amino acid sequence by plotting the hydrophilicity and hydrophobicity and by PSORT program suggested that mouse BA2303 protein has seven transmembrane regions as do rabbit and human BA2303 (FIG. 8).

BA2303 proteins of the present invention, from rabbit, human and mouse, have a high sequence homology at the amino acid level between each other (FIG. 9).

EXAMPLE 8
Isolation of Mouse BA0306 cDNA

As was described in Example 6, rabbit BA0306 gene was used as a probe for screening a mouse cDNA library (STRATAGENE, code: 936-309), and the mouse homologue containing the nucleotide sequence described in SEQ ID NO: 27 was isolated. The deduced amino acid sequence of the coding region was described in SEQ ID NO: 28.

BA0306 proteins of the present invention, from rabbit, human and mouse, have a high sequence homology at the amino acid level with each other (FIG. 10).

EXAMPLE 9
Preparation of Anti-peptide Antibody Against Human BA2303

An oligopeptide (Gln-Asp-Ala-Gln-Gly-Gln-Arg-Ile-Gly-His-Phe-Glu-Phe-His-Gly) containing amino acid residues from 35 to 49 in the sequence described in SEQ ID NO: 4 was synthesized. Two rabbits were immunized three times with peptide and Freund's complete adjuvant. The rabbit sera obtained after each immunization were subjected to ELISA using horse radish peroxidase-conjugated goat anti-rabbit IgG and microplates having wells coated with the peptide (1 µg/well), and the fluorescence intensity was measured at 492 nm to determine the antibody titers. Titers were determined as dilution of sera to obtain a fluorescence intensity at 492 nm not more than 0.2. The result showed that the titers of antisera taken from a rabbit A were 50-fold or less before immunization (3 to 5 ml), 30,600-fold after the first immunization (16 ml), 40,900-fold after the second immunization (25 ml), and 41,100-fold after the third immunization (23 ml), indicating that the titer was increased with the number of immunization. The titers of antisera from the other rabbit B were not more than 50-fold before immunization (3 to 5 ml), 149,200-fold after the first immunization (25 ml), 327,500-fold after the second immunization (25 ml), and 500,000-fold or more after the third immunization (25 ml), indicating that the titer was increased and that antibody against the peptide was produced.

Next, the forth immunization was performed on both rabbits A and B. The titers after the forth immunization were 46,500-fold in rabbit A, and 500,000-fold or more in rabbit B as was after the third immunization. Then, the antisera taken from rabbit A after the forth immunization were purified by affinity chromatography using a column absorbed with the peptide that had been used as an antigen. The titer of the sera from rabbit A after purification was 69,800-fold.

EXAMPLE 10
Preparation of Recombinant Fusion Protein with Human BA2303 Protein Fusion proteins of the present invention were prepared as a fusion protein with maltose binding protein (MBP) using the expression plasmid pMAL-C2 (New England Bio Labs. (NEB)), which contains a DNA encoding MBP. Experimental procedures were performed according to the manufacturer's instructions (Catalogue number: #800, 'Protein Fusion & Purification System' Ver. 3.03, December 1994 revised) and by the standard method of recombinant DNA technology.

Using a template of the DNA encoding human BA2303 (SEQ ID NO: 3), which was cloned in the previous Example, a DNA containing the nucleotide sequence corresponding to the N-terminal amino acids (residues 22 (Gly) to 171 (His)), having EcoRI and HindIII restriction sites at 5' and 3' termini, respectively, was amplified by PCR according to the standard method. Oligonucleotides described in SEQ ID NO: 29 and SEQ ID NO: 30 were used as 5' and 3' primers, respectively. The above pMAL-C2 expression plasmid (NEB, inserted with a DNA encoding MBP) was digested with EcoRI and HindIII, and the resulting fragments were recovered. Using a commercially available DNA ligation kit, the above PCR products of human BA2303 were ligated into the pMAL-C2, and the resulting plasmid was used to transfected *E. coli* TB1 cells. The bacterial expression plasmid was prepared in a large quantitiy from the transformed colony. A culture of the transformed colony (1/100 volume) was inoculated into 1 liter of LB broth containing ampicillin and glucose, and incubated with shaking until the OD value became up to 0.5. Then, isopropanol-β-D-thiogalactopyranoside (IPTG) was added to the culture to the final concentration of 0.3 mM, and shaking culture was performed further (3 hr). The culture was then centrifuged to remove the supernatant, and the precipitated bacteria was resuspended in cold column buffer (50 ml, composition: 20 mM Tris-HCl, 200 mM NaCl, 1 mM EDTA, and 10 mM mercaptoethanol), which was supplemented with 0.1 M PMSF (50 µl, phenylmethylsulfonyl fluoride) to suppress protease digestion.

The following procedures were carried out on ice unless otherwise noted. The obtained bacteria suspension was sonicated on ice to disrupt cells. Then, the suspension was centrifuged (9000 rpm, 15 to 30 min) to recover soluble fraction. The soluble fraction was diluted with ice-cold column buffer to load on a column.

Amylose resin (15 ml, BIORAD) was packed in a disposable column (2.5 dia.×10 cm), washed, and equilibrated with 8 volumes of ice-cold column buffer. The sample was loaded onto the column using a pump to keep the flow rate 1 ml/min, and washed with ice-cold column buffer.

The fusion protein was eluted and fractionated with ice-cold column buffer containing 10 mM maltose. Each fraction was separated by SDS-PAGE, and analyzed by western blotting using antisera against MBP (NEB). Fractions producing a band detected by western blotting at the position approximately corresponding to that of the full-length fusion protein were determined to be positive. Next, the positive fractions were further purified. MBP/BA2303 fusion protein can be digested by adding 1 mg/ml factor Xa (5 µl) to the solution containing the fusion protein and incubating it for 24 hr. Digestion of the fusion protein can be determined by SDS-PAGE followed by western blotting using antisera against MBP.

EXAMPLE 11
Preparation of Antibody Against Human BA2303 Protein

Recombinant protein prepared in Example 10, containing approximately 150 N-terminal amino acids of human BA2303 protein (residues 22 (Gly) to 171 (His)), was used as an immunogen. Two rabbits were immunized with the recombinant protein and Freund's complete adjuvant. The rabbit sera was subjected to ELISA using horse radish peroxidase-conjugated goat anti-rabbit IgG and microplates having wells coated with the peptide (1 µg/well), and the fluorescence intensity was measured at 492 nm to determine the antibody titers. The titer was determined as dilution of serum to obtain a fluorescence intensity at 492 nm not more than 0.2. The result showed that the titer of sera taken from a rabbit was 50-fold or less before immunization (3to 5 ml), and 316,900-fold after immunization (18 ml), indicating that the titer was increased. The titer of the sera from the other rabbit was less than 50-fold before immunization (3 to 5 ml), and increased to 312,300-fold after immunization (23 ml), indicating that antibody against the recombinant protein was produced.

EXAMPLE 12
Construction of an Expression Vector for Recombinant Human BA2303

Using a template of the DNA encoding human BA2303 (SEQ ID NO: 3), which was cloned in the previous Example, a DNA containing the nucleotide residues 77 to 1419 (containing the entire open reading frame (ORF)), having XbaI restriction sites at both 5' and 3' termini, was amplified by PCR according to the standard method. Oligonucleotides described in SEQ ID NO: 31 and in SEQ ID NO: 32 were used as 5' and 3' primers, respectively. The resulting PCR products were ligated into the XbaI site of the pcDNA expression plasmid (Invitrogen) using a commercially available DNA ligation kit to construct an expression vector for recombinant human BA2303. Higher eukaryotic host cells such as COS cells can be transfected with the vector, and the resulting colonies are selected to obtain transfected cells. Human BA2303 proteins can be expressed abundantly on the cell surface of the transfected cells by incubating the them in appropriate medium such as DMEM containing 10% FCS.

EXAMPLE 3
Preparation of Recombinant Rabbit BA0306 Protein

Using a template of the DNA encoding rabbit BA0306 (SEQ ID NO: 7), which was cloned in the previous Example, a DNA containing the nucleotide residues 2017 (Ile) to 2196 (Met), having BamHI and SalI restriction sites at 5' and 3' termini, respectively, was amplified by PCR according to the standard method. In the amino acid sequence (60 residues) encoded by the rabbit nucleotide sequence (nucleotides 2017 (Ile) to 2196 (Met)), 58 residues are the same as those in the corresponding human BA0306 sequence (residues 535 to 594 in SEQ ID NO: 10). Oligonucleotides described in SEQ ID NO: 33 and in SEQ ID NO: 34 were used as 5' and 3' primers, respectively.

The expression plasmid pQE-32 (QIA expression type IV construct, QIAGEN) was digested with BamHI and SalI, and then blunted.

According to the instruction manual for handling pQE-32, the obtained PCR products were ligated into the blunted ends of pQE-32 digested with BamHI-SalI using a commercially available DNA ligation kit. The resulting expression vector for recombinant human BA0306 was named as pQE-32R7-15.

Next, *E. coli* cells (XL-1 blue MRF') were transformed with the pQE-32R7-15 according to the standard method, and the transformed colonies were selected ("Gene Engineering Handbook" Jikken-Igaku Bessatsu, Yodosha (1992) 46–51). A culture of the transformed cells was inoculated into LB broth containing ampicillin and glucose, and incubated at 37° C. with shaking, with measuring the OD. Then, IPTG (isopropanol-β-D-thiogalactopyranoside) was added to the culture to the final concentration of 1 mM, and shaking culturing was further performed at 37° C. for 4 hrs. The culture was centrifuged to remove the supernatant, and the precipitated bacteria was resuspended in column buffer. The suspension was sonicated on ice to disrupt cells, then centrifuged, and soluble fraction was recovered. The soluble fraction was diluted with ice-cold column buffer to load on a column.

A column was packed with Ni-NTA resin, washed, and equilibrated with column buffer. The samples were applied on the column and washed with column buffer. The eluted fractions were collected, and thus recombinant rabbit BA0306 protein was obtained.

EXAMPLE 14
Preparation of Antibody Against Human BA0306

Recombinant rabbit BA0306 protein prepared in Example 13 was used as an immunogen. The protein and Freund's complete adjuvant were used to immunize chickens. The chicken sera were subjected to ELISA using horse radish peroxidase-conjugated anti-chicken IgG and microplates having wells coated with the recombinant protein (1 μg/well), and the fluorescence intensity was measured to determine the antibody titers. The result showed that the titer was increased, indicating that antibody against the ecombinant protein was produced.

Furthermore, rabbit BA0306 protein fragment, which was used as an immunogen in this example, and the above recombinant human BA0306 protein were detected by western blotting using the chicken antisera, indicating that the antisera had a cross reactivity with human BA0306 protein.

EXAMPLE 15
Generation of Knockout Mice of Mouse BA2303 Gene

A knockout mouse, whose endogenous gene encoding mouse BA2303 protein was inactivated, was generated as follows.

(1) Construction of a targeting vector

A targeting vector for generation of a knockout mouse, in which an endogenous gene encoding mouse BA2303 protein was inactivated (knocked out) by homologous recombination (Nikkei-Science (1994) May, 52–62), was constructed as follows.

The cDNA encoding mouse BA2303 protein (SEQ ID NO: 5), which was cloned in the previous Example, was labeled with $^{32}$P by the standard method to obtain a probe used in hybridization. The probe was used to screen a cosmid mouse genomic DNA library ("Labomanual Human Genome Mapping" Hori M., and Nakamura Y. edit., Maruzen Syuppan), and thus, a mouse genomic DNA clone containing exons (E1, E2, and E3) which encode mouse BA2303 protein was isolated. The structure of the genomic DNA was schematically shown in FIG. 11. The genomic DNA was subcloned into a plasmid, and digested with SacII to remove the region of 124 bp encompassing E1 and the intron between E1 and E2, and then ligated with an insert of a neomycin resistance gene of 1143bp (neo, as a positive selection marker), which had been digested with restriction enzymes and blunted.

The plasmid pBluescript II SK(–) was digested with SacII, and ligated with an insert of a thymidine kinase gene (TK, as a negative selection marker). Then, the resulting pBluescript II SK(–) was digested with XbaI, and ligated with an insert of the above mouse BA2303 genomic DNA having a neo gene insertion.

(2) Transfection of the targeting vector into ES cells

Mouse embryonic stem cells (ES cells) (Nature (1993) 362, 255–258; Nature (1987) 326, 292–295), which were cultured in DMEM containing 15% fetal bovine serum, were trypsinized to obtain single isolated cells, washed three times in phosphate buffer, and prepared as a cell suspension of 1×10⁷ cells/ml. The targeting vector was added to the cells (25 μg/1 ml cell suspension), and electroporation was performed with a single pulse of 350 V/cm (25 μF). Then, the ES cells were seeded into cm dishes (1×10⁷ cells/dish), cultured for one day in maintenance medium, and then the medium was replaced with selection medium (containing G418 (250 μg/ml) and 2 μM gancyclovir). The culture was continued with replacing the medium every two days. On the tenth day after transfection of targeting vector, 540 neomycin resistant ES clones were isolated using a micropipet under microscopic observation. The clones were cultured separately in 24 well plates layered with feeder cells, and replica of 540 neomycin resistant ES cells were obtained.

(3) Screening of knockout ES cells

Each neomycin resistant ES clone was examined by PCR whether its endogenous gene encoding mouse BA2303 protein was inactivated (knocked out) by homologous recombination.

PCR was performed using genomic DNA extracted from each neomycin resistant ES clone as a template, with two primers designed based on the sequence of the neo gene (SEQ ID NO: 36 and SEQ ID NO: 37) (1) and on the mouse BA2303 genomic DNA sequence which locates on the flanking region of the BA2303 DNA which was inserted in the targeting vector (SEQ ID NO: 35 and SEQ ID NO: 38) (2). DNA was purified using an automated DNA purification robot (Kubota). The result showed that desired PCR products were obtained in several clones among the ES clones examined. Further selection of these clones can be performed by genomic Southern blotting. Genomic DNA was extracted from each clone, digested with restriction enzymes, and separated by electrophoresis on an agarose gel. Then, the DNA was transferred onto a nylon membrane, and subjected to hybridization using a probe designed based on the genomic sequence of mouse BA2303. The probe was designed based on the sequence which locates in the flanking region of the site of homologous recombination, and thus enabled to distinguish mutated genome from normal one by size. The knockout ES clone selected in this way was used for generation of knockout mice as described below.

(4) Generation of knock out mice

The above obtained ES cells, having inactivation in the endogenous gene encoding mouse BA2303 protein as a result of homologous recombination, were injected into blastocysts obtained by crossing C57BL6 mice (Japan Charles River) (15 cells/embryo, microinjection). Immediately after microinjection, the blastocysts were implanted into uterines of ICR mice (Clea Japan), which had undergone pseudopregnancy treatment two days and half before (10 blastocysts/one side of the uterine). Thus, desired chimera mice were obtained. The chimera were crossed with normal C57BL6 mice to obtain agouti mice, whose color is attributed to a gene determining hair color, originating from ES cells.

EXAMPLE 16
Generation of Knockout Mice of Mouse BA0306 Gene
(1) Construction of a targeting vector A targeting vector for generation of a knockout mouse, in which the endogenous gene encoding mouse BA0306 protein was inactivated (knocked out) by homologous recombination (Nikkei-Science (1994) May, 52–62), was constructed as follows. The cDNA encoding mouse BA0306 protein (SEQ ID NO: 27), which was cloned in the previous Example, was labeled with $^{32}$p by the standard method to obtain a probe used in hybridization. The probe was used to screen a 129SVJ mouse genomic DNA library (STRATAGENE), and a mouse genomic DNA clone containing exons (exon I, II, III, IV, and V) that encode mouse BA0306 protein was isolated.

The plasmid pBluescript II SK(-) was digested with XhoI and HindIII, and ligated with XhoI-HindIII-digested thymidine kinase gene (TK, as a negative selection marker). Next, NotI-digested pBluescript II SK(-) was ligated with an insert of the above mouse BA0306 genomic DNA (exons I to V). Then, the neomycin resistance gene (neo, as a positive selection marker) was digested with BamHI and XhoI, blunted, and ligated into the Aor51HI site of the exon V in the mouse BA0306 genomic DNA. Finally, the resulting pBluescript II SK(-) was digested with SacII and linealized to use as a targeting vector.

(2) Transfection of the targeting vector into ES cells

Mouse embryonic stem cells (ES cells, 1×10$^8$ cells) (Nature (1993) 362, 255–258; Nature (1987) 326, 292–295), which were cultured in DMEM containing 15% fetal bovine serum, were trypsinized to obtain single isolated cells, washed three times in phosphate buffer, and then prepared as a cell suspension of 1×10$^7$ cells/ml. The targeting vector was added to the (25 μg/1 ml cell suspension), and electroporation was performed with a single pulse of 350 V/cm (25 μF). Then, the ES cells were seeded into 10 cm dishes (1×10$^7$ cells/dish), cultured 1 day in maintenance medium, and then the medium was replaced with selection medium (containing G418 (250 μg/ml) and 2 μM gancyclovir). The culture was continued with replacing the medium every two days. On the tenth day after transfection, 573 neomycin resistant ES clones were isolated using a micropipet under microscopic observation. The clones were cultured separately in 24 well plates layered with feeder cells, and replica of 573 neomycin resistant ES cells were obtained.

(3) Screening of knockout ES cells

Each neomycin resistant ES clone was examined by genomic Southern blotting whether its endogenous gene encoding mouse BA0306 protein was inactivated (knocked out) through homologous recombination.

Genomic DNA was extracted from each neomycin resistant ES clone, and genomic Southern blotting was performed on EcoRI digested genomic DNA fragments according to the standard method using the following probes.
(Probe 1)
5' flanking DNA which was amplified using two primers described in SEQ ID NO: 39 and SEQ ID NO: 40.
(Probe 2)
3' flanking DNA which was amplified using two primers described in SEQ ID NO: 41 and SEQ ID NO: 42.

DNA was purified using an automated DNA purification robot (Kubota).

If the endogenous gene encoding BA0306 is normally targeted by the targeting vector, the 5' and 3' flanking genes encompassing the integrated neo gene can be detected as 7 kb and 5 kb bands, respectively.

The result showed that desired knockout of the gene was occurred in three ES clones (named as 0-16-9, 0-22-11, and 0-22-18), which were used for generation of knockout mice as described below.

(4) Generation of knock out mice

The ES clones obtained above, having inactivation in the endogenous gene encoding mouse BA0306 protein as a result of homologous recombination, were microinjected into blastocysts obtained by crossing C57BL6 mice (Japan Charles River) (15 cells/embryo). Immediately after microinjection, the blastocysts were transferred to uterines of ICR mice (Clea Japan) (10 blastocysts/one side of the uterine), which had undergone pseudopregnancy treatment two days and half before. As a result, desired knockout chimera mice were obtained from each ES clone as followings.

(Clone 0-16-9)
Total number of injected cells: 83
Littermates: 13
Chimera mice: 7
Chimera where contribution to hair color is 80% or more: 2

(Clone 0-22-11)
Total number of injected cells: 202
Littermates: 12
Chimera mice: 3
Chimera where contribution to hair color is 80% or more: 3

(Clone 0-22-18)
Total number of injected cells: 148
Littermates: 9
Chimera mice: 5

The chimera were crossed with normal C57BL6 mice to obtain agouti mice whose color is attributed to a gene determining hair color, originating from ES cells.

INDUSTRIAL APPLICABILITY

The present invention provides two novel physiologically active protein molecules (BA0306, and BA2303) having characteristics described below, which are specifically expressed in arteriosclerosis or coronary restenosis, and are predicted to relate closely to the onset and progress of these diseases; their fragments; a gene (DNA) encoding the protein molecules; an antibody reactive with the molecule, and its fragment; and pharmaceutical compositions comprising the above protein molecule or the antibody.

[BA0306]

A molecule having the following characteristics, and presumed to have inhibitory effects on active oxygen species such as nitrogen monoxide (NO), which has been identified to be involved in the progress of arteriosclerosis and restenosis.

(1) Its expression is increased from day 1 to day 7 after PTCA of the coronary aorta (peak at day 4).
(2) Its mRNA is expressed in various human tissues as detected by Northern blotting as approximately 3.5 kb and 4.4 kb bands.
(3) Its 10 predicted transmembrane regions.
(4) Its sequence homology at the amino acid level with *S. cerevisiae* oxidative stress resistance protein, *S. cerevisiae* zinc/cadmium resistance protein, and heavy metal ion resistance protein, etc.

[BA2303]

A molecule having the following characteristics, and presumed to be a G protein(GTP binding protein)-coupled receptor that transduces a specific signal through intracellular G protein to an effector on the plasma membrane or in the cytoplasm by binding to an in vivo ligand which is involved in the onset and progress of arteriosclerosis and restenosis.

(1) Its expression is increased day 1 after PTCA of the coronary aorta, reaches the maximum on day 2 to day 4, and continued until day 7.
(2) Its mRNA is expressed in various human tissues as detected by Northern blotting as approximately 3.9 kb and 2.1 kb bands.
(3) having seven predicted transmembrane regions.

Therefore, a gene (DNA) or protein of the present invention or its part, and an antibody reactive with the protein, or a part of the antibody are extremely useful in developing the drugs targeting the gene or the protein molecule for treatment and prevention of arteriosclerosis as well as restenosis after PTCA of arterial embolism. Also, the DNA itself is very useful as an antisense medicine, the extracellular domain fragment of the protein is useful as a soluble receptor medicine, and the antibody or its part is useful as an antibody medicine.

Furthermore, the gene (DNA), protein, and antibody of the present invention are useful as a reagent for screening a protein (ligand) interacting with the protein of the invention, identification of the function of the ligand, and developing a drug which targets the ligand.

In addition, based on the nucleotide sequence originating from rabbit or mouse, as an embodiment of the DNA of the present invention, model animals (knockout animals) can be generated by disrupting (inactivating) a corresponding endogenous gene. Similarly, transgenic animals can be generated as a model animal by introducing human DNA, as an embodiment of the DNA of the present invention, into mammals such as mice except human. It is possible to identify the functions of the gene and protein of the invention by analyzing the physical, biological, pathological, and genetical characteristics of the model animals.

Moreover, it is possible to generate model animals having a human gene of the invention alone by crossing the model animals, whose endogenous gene is disrupted, with the transgenic animals. Thus, it is possible to estimate the therapeutic effects of a drug which targets the introduced human gene (compounds, and antibodies, etc.) by administrating the drug into the model animals.

---

What is claimed is:

1. An isolated DNA encoding a protein having the amino acid sequence of SEQ ID NO: 4.

2. An isolated DNA encoding a protein fragment comprising an extracellular region of a protein having the amino acid sequence of SEQ ID NO: 4.

3. An isolated DNA comprising a nucleotide sequence comprising nucleotide residues 97 to 1419 of the nucleotide sequence of SEQ ID NO: 3.

4. An expression vector comprising the DNA of any one of claims 1 to 3.

5. A transformant carrying the expression vector of claim 4.

* * * * *

UNITED STATES PATENT AND TRADEMARK OFFICE
CERTIFICATE OF CORRECTION

PATENT NO. : 6,710,171 B1
DATED : March 23, 2004
INVENTOR(S) : Yusuke Nakamura et al.

It is certified that error appears in the above-identified patent and that said Letters Patent is hereby corrected as shown below:

<u>Title page,</u>
Item [75], Inventors, "Shuichi Tsukuda" has been replaced by -- Shuichi Tsukada --.

Signed and Sealed this

Twenty-seventh Day of July, 2004

JON W. DUDAS
*Acting Director of the United States Patent and Trademark Office*